United States Patent
Alsina-Fernandez et al.

(10) Patent No.: US 12,295,987 B2
(45) Date of Patent: May 13, 2025

(54) METHOD OF USING A GIP/GLP1 CO-AGONIST FOR DIABETES

(71) Applicant: Eli Lilly and Company, Indianapolis, IN (US)

(72) Inventors: Jorge Alsina-Fernandez, Indianapolis, IN (US); Over Cabrera, Carmel, IN (US); Tamer Coskun, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 892 days.

(21) Appl. No.: 17/260,279

(22) PCT Filed: Jul. 22, 2019

(86) PCT No.: PCT/US2019/042824
§ 371 (c)(1),
(2) Date: Jan. 14, 2021

(87) PCT Pub. No.: WO2020/023388
PCT Pub. Date: Jan. 30, 2020

(65) Prior Publication Data
US 2023/0293638 A1    Sep. 21, 2023

Related U.S. Application Data

(60) Provisional application No. 62/740,640, filed on Oct. 3, 2018, provisional application No. 62/730,562, filed on Sep. 13, 2018, provisional application No. 62/702,180, filed on Jul. 23, 2018.

(51) Int. Cl.
*A61K 38/26* (2006.01)
*A61P 3/10* (2006.01)

(52) U.S. Cl.
CPC ............... *A61K 38/26* (2013.01); *A61P 3/10* (2018.01)

(58) Field of Classification Search
CPC .................... A61K 38/26; A61P 3/10
See application file for complete search history.

(56) References Cited

U.S. PATENT DOCUMENTS

2013/0065828 A1*  3/2013  Ruus ................. A61K 31/155
                                                      514/7.2

FOREIGN PATENT DOCUMENTS

WO    2015022420    2/2015
WO    2016111971    7/2016

OTHER PUBLICATIONS

International Search Report of the International Searching Authority pertaining to International Application No. PCT/US2019/042824; Date of Mailing: Oct. 14, 2019; 6 pages.
Written Opinion of the International Searching Authority pertaining to International Application No. PCT/US2019/042824; Date of Mailing: Oct. 14, 2019; 10 pages.
Nathan, D. M., Buse, J. B., Davidson, M. B., Ferrannini, E., Holman, R. R., Sherwin, R., & Zinman, B. (2009). Medical management of hyperglycemia in type 2 diabetes: a consensus algorithm for the initiation and adjustment of therapy: a consensus statement of the American Diabetes Association and the European Association for the Study of Diabetes. *Diabetes care*, 32(1), 193-203.
Frias, J. P., Nauck, M. A., Van, J., Kutner, M. E., Cui, X., Benson, C., . . . & Haupt, A. (2018). Efficacy and safety of LY3298176, a novel dual GIP and GLP-1 receptor agonist, in patients with type 2 diabetes: a randomised, placebo-controlled and active comparator-controlled phase 2 trial. *The Lancet*, 392(10160), 2180-2193.
Coskun, T., Sloop, K. W., Loghin, C., Alsina-Fernandez, J., Urva, S., Bokvist, K. B., . . . & Kuchibhotla, U. (2018). LY3298176, a novel dual GIP and GLP-1 receptor agonist for the treatment of type 2 diabetes mellitus: from discovery to clinical proof of concept. *Molecular metabolism*, 18, 3-14.
Chaplin, S., & Bain, S. (2016). Properties of GLP-1 agonists and their use in type 2 diabetes. *Prescriber*, 27(1), 43-46.

\* cited by examiner

*Primary Examiner* — Julie Ha
(74) *Attorney, Agent, or Firm* — Parker D. McCrary; Macharri A. Vorndran-Jones

(57) ABSTRACT

Provided herein are methods of treating type 2 diabetes (T2D) using a novel dosing regimen of a GIP:GLP-1 Peptide having a GIP:GLP-1 receptor agonist potency ratio that is about 2.5:1 to about 10:1 GIP to GLP-1. Also provided herein are methods of treating T2D using a novel dosing regimen of a GIP:GLP-1 Peptide having a GIP:GLP-1 receptor agonist potency ratio that is about 2.5:1 to about 5:1 GIP to GLP-1.

2 Claims, No Drawings

Specification includes a Sequence Listing.

METHOD OF USING A GIP/GLP1 CO-AGONIST FOR DIABETES

The present invention provides methods of treating type 2 diabetes (T2D) using a novel dosing regimen of a GIP/GLP-1 co-agonist compound (hereafter GIP:GLP-1 Peptide) having a GIP:GLP-1 receptor agonist potency ratio that is about 2.5 to about 10:1 GIP to GLP-1. Furthermore, the present invention provides methods of treating T2D using a novel dosing regimen of a GIP:GLP-1 Peptide having a GIP:GLP-1 receptor agonist potency ratio that is about 2.5:1 to about 5:1 GIP to GLP-1. Also, the present invention provides methods of inducing T2D remission using a novel dosing regimen of a GIP:GLP-1 Peptide. The present invention also provides methods of treating obesity using a novel dosing regimen of a GIP:GLP-1 Peptide.

Over the past several decades, the prevalence of diabetes has continued to rise. T2DM is the most common form of diabetes accounting for approximately 90% of all diabetes. T2DM is characterized by high blood glucose levels associated mainly with insulin resistance. T2D is epidemic. Long-term consequences of T2D translate into enormous human suffering and economic costs; however, much of the morbidity associated with long-term microvascular and neuropathic complications can be substantially reduced by interventions that achieve glucose levels close to the non-diabetic range. Although new classes of medications and numerous combinations have been demonstrated to lower glycemia, it is reported that current-day management generally fails to achieve and maintain the glycemic levels most likely to provide optimal healthcare status for people with diabetes. *The Medical Management of Hyperglycemia in Type* 2 *Diabetes: A Consensus Algorithm for the Initiation and Adjustment of Therapy*, DIABETES CARE, VOLUME 32:193-203; NUMBER 1, January 2009. The American Diabetes Association guidelines recommend to use HbA1c in the range of 5.7 to 6.1% (39-47 mmol/mol) as the prediabetes level. (39-47 mmol/mol). *American Diabetes Association*, Diabetes Care. 2018 January; 41 (Supplement 1): S55-S64. There is a significant need for a treatment method to enable patients with T2D to reach their glycemic treatment goals.

It is well-known that GLP1 treatments are associated with nausea, vomiting, and/or diarrhea. For example, one study reported that all GLP-1 receptor agonist dosing regimens significantly increased the incidence of gastrointestinal adverse events. Diabetes Technol Ther. 2015 January; 17 (1): 35-42.

Although endogenous GIP exerts strong insulinotropic effects in healthy subjects, the severe reduction in insulinotropic effect of GIP and the GIP-dependent enhancement of postprandial glucagon response have discouraged development of GIP-based therapies for T2D. Seino, et. al., *GIP and GLP-*1, *the two incretin hormones: Similarities and differences*; Journal of Diabetes Investigation, Volume 1 Issue 1/2 (February/April 2010) (8-23) p 16.

Also, previous clinical trials of a GIP/GLP1 co-agonist compound having a balanced GIP/GLP1 potency have been performed and found that tolerability at high doses was limited by gastrointestinal adverse events. Portron, A. et al. "Pharmacodynamics, pharmacokinetics, safety and tolerability of the novel dual glucose-dependent insulinotropic polypeptide/glucagon-like peptide-1 agonist RG7697 after single subcutaneous administration in healthy subjects." Diabetes Obes. Metab. 2017; 19:1446-1453. Finan, B. et al. "Unimolecular dual incretins maximize metabolic benefits in rodents, monkeys, and humans." Sci Trans Med. 2013; 5 (209): 209ra151. The dose limitation associated with gastrointestinal adverse events may prevent dosing to the desired effective dose, may compromise patient compliance with treatment, and may limit the effectiveness of the treatment regimen.

While treatments for T2D include GLP-1 receptor agonists, there are currently no approved T2D treatments reporting GIP/GLP receptor co-agonism. Furthermore, there are no available treatments having a ratio that is about 2.5:1 to about 10:1 GIP to GLP-1 receptor agonist potency to treat T2D.

One GIP/GLP-1 receptor co-agonist having a potency ratio of about 3.6:1 GIP:GLP-1 is known as tirzepatide. In a Phase II clinical trial, tirzepatide treatment using once weekly subcutaneous doses including a 15 mg dose provided dramatic reduction of HbA1c, remission of diabetes for many patients after 26 weeks, and dramatic improvement in weight control.

Obesity is a complex medical disorder resulting in excessive accumulation of adipose tissue mass. Today obesity is a global public health concern that is associated with undesired health outcomes and morbidities. Desired treatments for patients with obesity strive to reduce excess body weight, improve obesity-related co-morbidities, and maintain long-term weight reduction. Available treatments for obesity are particularly unsatisfactory for patients with severe obesity. Successful treatment of obesity is associated with alleviation or prevention of T2D. There is a need for alternative treatment options to induce therapeutic weight loss in patients in need of such treatment. Compounds having a ratio that is about 2.5:1 to about 10:1 GIP receptor agonist potency to GLP-1 receptor agonist potency are useful for significantly improving weight management, and can prevent the manifestation of T2D in formerly obese patients susceptible to T2D.

WO2016/111971 describes peptides stated to have GLP-1 and GIP activity. WO2013/164483 also discloses compounds stated to have GLP-1 and GIP activity. U.S. Pat. No. 9,474,780 generally describes compositions containing a GIP/GLP1 co-agonist, administered by parenteral routes, and generally discloses a wide dosage range up to about 30 mg per person per week. U.S. Pat. No. 9,474,780 discloses the use of GIP/GLP1 co-agonists for treating diabetes, obesity, and other conditions. U.S. Pat. No. 9,474,780 describes and claims tirzepatide.

The present invention provides novel dosing regimens of a GIP:GLP-1 Peptide for use in the aforementioned therapies (glycemic control/diabetes, obesity) that include one or more titration doses and a maintenance dose. More specifically, the present invention provides novel dosing regimens that include a titration dose and a maintenance dose wherein the titration dose is about 50% of the maintenance dose and is administered about once weekly for a minimum of about 2 weeks before administration of the maintenance dose. In another aspect, the dosing regimen comprises three titration doses: the first being about 25% of the maintenance dose, the second being about 50% of the maintenance dose and the third being about 75% of the maintenance dose, and a maintenance dose wherein each titration dose is administered about once weekly for a minimum of about 2 weeks before the administration of the next higher dose. In yet a third embodiment, the dosing regimen comprises five titration doses: the first being about 17% of the maintenance dose, the second being about 33% of the maintenance dose, the third being about 50% of the maintenance dose, the fourth being about 66% of the maintenance dose and the fifth being about 83% of the maintenance dose wherein each titration dose is administered about once weekly for a minimum of about 2 weeks before the administration of the next higher dose. Further embodiments are dosing regimens as above where each titration dose is administered about once weekly for about 4 weeks before the administration of the next higher dose begins.

In an embodiment, GIP:GLP-1 Peptides of the present invention have a receptor agonist potency ratio as measured after a 60 minute incubation using a casein cAMP assay normalized against GIP and GLP-1 of about 2.5:1 to about 10:1 GIP to GLP-1. In an embodiment, GIP:GLP-1 Peptides of the present invention have a receptor agonist potency ratio as measured after a 60 minute incubation using a casein cAMP assay normalized against GIP and GLP-1 of about 2.5:1 to about 5:1 GIP to GLP-1. In an embodiment, GIP:GLP-1 Peptides of the present invention have a receptor agonist potency ratio as measured after a 60 minute incubation using a casein cAMP assay normalized against GIP and GLP-1 of about 2.5:1 to about 3.5:1 GIP to GLP-1 . . . . In an embodiment, GIP:GLP-1 Peptides of the present invention have a receptor agonist potency ratio as measured after a 60 minute incubation using a casein cAMP assay normalized against GIP and GLP-1 of about 2.5:1 to about 10:1 GIP to GLP-1. In an embodiment, GIP:GLP-1 Peptides of the present invention have a receptor agonist potency ratio as measured after a 60 minute incubation at 37 C using a casein cAMP assay normalized against GIP and GLP-1 of about 2.5:1 to about 10:1 GIP to GLP-1.

Accordingly, the present invention provides a method of treating type 2 diabetes in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

The present invention further provides a method of improving glycemic control in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

Furthermore, the present invention provides a method of improving weight management in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

Furthermore, the present invention provides a method of treating chronic kidney disease in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

Furthermore, the present invention provides a method of treating atherosclerosis in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

Furthermore, the present invention provides a method of treating NAFLD in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

Furthermore, the present invention provides a method of treating NASH in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

Furthermore, the present invention provides a method of curing diabetes, inducing remission or regression of diabetes or preventing diabetes in a patient in need thereof, comprising: administering a titration dose of a GIP:GLP-1 Peptide for about two weeks and thereafter administering a maintenance dose of that GIP:GLP-1 Peptide wherein the titration dose is about 50% of the maintenance dose and wherein the GIP:GLP-1 Peptide has a receptor agonist potency ratio as measured after a 60 minute incubation using a casein cAMP assay normalized against GIP and GLP-1 that is about 2.5:1 to about 10:1 GIP to GLP-1.

A further embodiment of the present invention are the methods above wherein three titration doses (about 25%, about 50% and about 75% of the maintenance dose) are administered starting with the 25% dose and wherein each titration dose is administered for about two weeks before the administration of the next higher dose begins. A further embodiment of the present invention are the methods above wherein five titration doses (about 17%, about 33%, about 50%, about 66% and about 83% of the maintenance dose) are administered starting with the 17% dose and wherein each titration dose is administered for about two weeks before the administration of the next higher dose. A further embodiment of the present invention are the methods above where the titration dose or doses are administered for about four weeks before the administration of the next higher dose begins.

Another aspect of the present invention are methods described above for treating type 2 diabetes, improving glycemic control, improving weight management, treating chronic kidney disease, treating NAFLD, treating NASH and to cure diabetes, induce remission or regression of diabetes, or prevent diabetes wherein the GIP:GLP-1 Peptide has a GIP:GLP-1 receptor agonist potency ratio that is about 2.5:1 to about 5:1 as measured after a 60 minute incubation using a casein cAMP assay normalized against GIP and GLP-1. A further aspect of the present invention are methods described above for treating type 2 diabetes, improving glycemic control, improving weight management, treating chronic kidney disease, treating NAFLD, treating NASH or to cure diabetes, induce remission or regression of diabetes, or prevent diabetes wherein the GIP:GLP-1 Peptide has a GIP:GLP-1 receptor agonist potency ratio that is about 2.5:1 to about 3.5:1 as measured after a 60 minute incubation using a casein cAMP assay normalized against GIP and GLP-1.

A further aspect of the present invention are the methods described above for treating type 2 diabetes, improving glycemic control, improving weight management, treating chronic kidney disease, treating NAFLD, treating NASH or to cure diabetes, induce remission or regression of diabetes, or prevent diabetes wherein the GIP:GLP-1 Peptide is a compound of SEQ ID NO: 3, or a pharmaceutically acceptable salt thereof. Another aspect of the present invention are the methods described above for treating type 2 diabetes, improving glycemic control, improving weight management, treating chronic kidney disease, treating NAFLD, treating NASH or to cure diabetes, induce remission or regression of diabetes, or prevent diabetes wherein the GIP:GLP-1 Peptide is a compound of SEQ ID NO: 3, or a pharmaceutically acceptable salt thereof, and wherein the compound of SEQ ID NO: 3, or a pharmaceutically acceptable salt thereof, has a GIP:GLP-1 receptor agonist potency ratio that is about 2.5:1 to about 5:1 as measured after a 60 minute incubation using a casein cAMP assay normalized against GIP and GLP-1. Another aspect of the present invention are the methods described above for treating type 2 diabetes, improving glycemic control, improving weight management, treating chronic kidney disease, treating NAFLD, treating NASH or to cure diabetes, induce remission or regression of diabetes, or prevent diabetes wherein the GIP:GLP-1 Peptide is a compound of SEQ ID NO: 3, or a pharmaceutically acceptable salt thereof, and wherein the compound of SEQ ID NO: 3, or a pharmaceutically acceptable salt thereof, has a GIP:GLP-1 receptor agonist potency ratio that is about 2.5:1 to about 3.5:1 as measured after a 60 minute incubation using a casein cAMP assay normalized against GIP and GLP-1.

In an embodiment 1 (a), the present invention provides a method of treating type 2 diabetes in a patient in need thereof, comprising:
  a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a maintenance dose of that GIP:GLP-1 Peptide;
wherein the titration dose is about 50% of the maintenance dose.

In embodiment 1 (b), the present invention provides a method of treating type 2 diabetes in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a maintenance dose of that GIP:GLP-1 Peptide;
wherein the first titration dose is about 25% of the maintenance dose, the second titration dose is about 50% of the maintenance dose and the third titration dose is about 75% of the maintenance dose.

In embodiment 1 (c), the present invention provides a method of treating type 2 diabetes in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a fourth titration dose of that GIP:GLP-1 Peptide for a minimum of about two weeks; and thereafter
  e) administering to said patient a fifth titration dose of that GIP:GLP-1 Peptide for a minimum of about two weeks; and thereafter
  f) administering to said patient a maintenance dose of that GIP:GLP-1 Peptide;
wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 1 (a1), the present invention provides a method of treating type 2 diabetes in a patient in need thereof, comprising:
  a) subcutaneiously administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 about once weekly for a minimum of about two weeks; and thereafter
  b) administering to said patient a maintenance dose of that GIP:GLP-1 Peptide;
wherein the titration dose is about 50% of the maintenance dose.

In embodiment 1 (b1), the present invention provides a method of treating type 2 diabetes in a patient in need thereof, comprising:
  a) subcutaneously administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 about once weekly for a minimum of about two weeks; and thereafter b) subcutaneously administering to said patient a second titration dose of that GIP:GLP-1 Peptide about once weekly for a minimum of about two weeks; and thereafter c) subcutaneously administering to said patient a third titration dose of that GIP:GLP-1 Peptide about once weekly for a minimum of about two weeks; and thereafter d) subcutaneously administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In embodiment 1 (c1), the present invention provides a method of treating type 2 diabetes in a patient in need thereof, comprising:

a) subcutaneously administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 about once weekly for a minimum of about two weeks; and thereafter b) subcutaneously administering to said patient a second titration dose of that GIP:GLP-1 Peptide about once weekly for a minimum of about two weeks; and thereafter c) subcutaneously administering to said patient a third titration dose of that GIP:GLP-1 Peptide about once weekly for a minimum of about two weeks; and thereafter d) subcutaneously administering to said patient a fourth titration dose of that GIP:GLP-1 Peptide about once weekly for a minimum of about two weeks; and thereafter e) subcutaneously administering to said patient a fifth titration dose of that GIP:GLP-1 Peptide about once weekly for a minimum of about two weeks; and thereafter f) subcutaneously administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 2 (a), the present invention provides a method of improving glycemic control in a patient in need thereof, comprising:

a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a maintenance dose of that GIP:GLP-1 Peptide;

wherein the titration dose is about 50% of the maintenance dose.

In an embodiment 2 (a), the present invention provides a method of improving glycemic control in a patient in need thereof, comprising:

a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a maintenance dose of that GIP:GLP-1 Peptide;

wherein the titration dose is about 50% of the maintenance dose.

In embodiment 2 (b), the present invention provides a method of improving glycemic control in a patient in need thereof, comprising:

a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a second titration dose of that GIP:GLP-1 Peptide for a minimum of about two weeks; and thereafter c) administering to said patient a third titration dose of that GIP:GLP-1 Peptide for a minimum of about two weeks; and thereafter d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In embodiment 2 (c), the present invention provides a method of improving glycemic control in a patient in need thereof, comprising:

a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a second titration dose of that GIP:GLP-1 Peptide for a minimum of about two weeks; and thereafter c) administering to said patient a third titration dose of that GIP:GLP-1 Peptide for a minimum of about two weeks; and thereafter d) administering to said patient a fourth titration dose of that GIP:GLP-1 Peptide for a minimum of about two weeks; and thereafter e) administering to said patient a fifth titration dose of that GIP:GLP-1 Peptide for a minimum of about two weeks; and thereafter f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 3 (a), the present invention provides a method of improving weight management in a patient in need thereof, comprising:

a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a maintenance dose of that GIP:GLP-1 Peptide;

wherein the titration dose is about 50% of the maintenance dose.

In embodiment 3 (b), the present invention provides a method of improving weight management in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In embodiment 3 (c), the present invention provides a method of improving weight management in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a fourth titration dose of that GIP:GLP-1 Peptide for a minimum of about two weeks; and thereafter
- e) administering to said patient a fifth titration dose of that GIP:GLP-1 Peptide for a minimum of about two weeks; and thereafter
- f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 4 (a), the present invention provides a method of treating chronic kidney disease in a patient in need thereof, comprising:
- a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a maintenance dose of that GIP:GLP-1 Peptide;

wherein the titration dose is about 50% of the maintenance dose.

In embodiment 4 (b), the present invention provides a method of treating chronic kidney disease in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In embodiment 4 (c), the present invention provides a method of treating chronic kidney disease in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a fourth titration dose of that GIP:GLP-1 Peptide for a minimum of about two weeks; and thereafter
- e) administering to said patient a fifth titration dose of that GIP:GLP-1 Peptide for a minimum of about two weeks; and thereafter
- f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 5 (a), the present invention provides a method of treating NAFLD in a patient in need thereof, comprising:
- a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a maintenance dose of that GIP:GLP-1 Peptide;

wherein the titration dose is about 50% of the maintenance dose.

In embodiment 5 (b), the present invention provides a method of treating NAFLD in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a maintenance dose of that GIP:GLP-1 Peptide;
wherein the first titration dose is about 25% of the maintenance dose, the second titration dose is about 50% of the maintenance dose and the third titration dose is about 75% of the maintenance dose.

In embodiment 5 (c), the present invention provides a method of treating NAFLD in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a fourth titration dose of that GIP:GLP-1 Peptide for a minimum of about two weeks; and thereafter
  e) administering to said patient a fifth titration dose of that GIP:GLP-1 Peptide for a minimum of about two weeks; and thereafter
  f) administering to said patient a maintenance dose of that GIP:GLP-1 Peptide;
wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 6 (a), the present invention provides a method of treating NASH in a patient in need thereof, comprising:
  a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a maintenance dose of that GIP:GLP-1 Peptide;
wherein the titration dose is about 50% of the maintenance dose.

In embodiment 6 (b), the present invention provides a method of treating NASH in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a maintenance dose of that GIP:GLP-1 Peptide;
wherein the first titration dose is about 25% of the maintenance dose, the second titration dose is about 50% of the maintenance dose and the third titration dose is about 75% of the maintenance dose.

In embodiment 6 (c), the present invention provides a method of treating NASH in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a fourth titration dose of that GIP:GLP-1 Peptide for a minimum of about two weeks; and thereafter
  e) administering to said patient a fifth titration dose of that GIP:GLP-1 Peptide for a minimum of about two weeks; and thereafter
  f) administering to said patient a maintenance dose of that GIP:GLP-1 Peptide;
wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 7 (a), the present invention provides a method of curing diabetes, inducing remission or regression of diabetes, or preventing diabetes in a patient in need thereof, comprising: to cure diabetes, induce remission or regression of diabetes, or prevent diabetes
  a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a maintenance dose of that GIP:GLP-1 Peptide;
wherein the titration dose is about 50% of the maintenance dose.

In embodiment 7 (b), the present invention provides a method of curing diabetes, inducing remission or regression of diabetes, or preventing diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In embodiment 7 (c), the present invention provides a method of curing diabetes, inducing remission or regression of diabetes, or preventing diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a fourth titration dose of that GIP:GLP-1 Peptide for a minimum of about two weeks; and thereafter
- e) administering to said patient a fifth titration dose of that GIP:GLP-1 Peptide for a minimum of about two weeks; and thereafter
- f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In embodiment 8, the titration doses of embodiments 1 (a)-(c), 2 (a)-(c), 3 (a)-(c), 4 (a)-(c), 5 (a)-(c), 6 (a)-(c) or 7 (a)-(c) are each administered for about four weeks before the administration of the next higher dose begins. Thus, for example, the present invention provides in embodiment 1 (d) a method of treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for about four weeks; and thereafter
- b) administering to said patient a maintenance dose of that GIP:GLP-1 Peptide;

wherein the titration dose is about 50% of the maintenance dose.

The present invention thus further provides in embodiment 1 (e), a method of treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for about four weeks; and thereafter
- b) administering to said patient a second titration dose of that GIP:GLP-1 Peptide for about four weeks; and thereafter
- c) administering to said patient a third titration dose of that GIP:GLP-1 Peptide for about four weeks; and thereafter
- d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

The present invention thus further provides in embodiment 1 (f), a method of treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for about four weeks; and thereafter
- b) administering to said patient a second titration dose of that GIP:GLP-1 Peptide for about four weeks; and thereafter
- c) administering to said patient a third titration dose of that GIP:GLP-1 Peptide for about four weeks; and thereafter
- d) administering to said patient a fourth titration dose of that GIP:GLP-1 Peptide for about four weeks; and thereafter
- e) administering to said patient a fifth titration dose of that GIP:GLP-1 Peptide for about four weeks; and thereafter
- f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In embodiment 9, the GIP:GLP-1 Peptide of embodiments 1 (a)-(c), 2 (a)-(c), 3 (a)-(c), 4 (a)-(c), 5 (a)-(c), 6 (a)-(c), 7 (a)-(c) or 8 is a compound of SEQ ID NO: 3, or a pharmaceutically acceptable salt thereof. Thus, for example, the present invention provides in embodiment 1 (g) a method of treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 wherein the GIP:GLP-1 Peptide is a compound of SEQ ID NO: 3 for about four weeks; and thereafter b) administering to said patient a maintenance dose of that GIP:GLP-1 Peptide;

wherein the titration dose is about 50% of the maintenance dose.

The present invention thus further provides in embodiment 1 (h), a method of treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 wherein the GIP:GLP-1 Peptide is a compound of SEQ ID NO: 3 for about four weeks; and thereafter
- b) administering to said patient a second titration dose of that GIP:GLP-1 Peptide for about four weeks; and thereafter
- c) administering to said patient a third titration dose of that GIP:GLP-1 Peptide for about four weeks; and thereafter
- d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

The present invention thus further provides in embodiment 1 (i), a method of treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 wherein the GIP:GLP-1 Peptide is a compound of SEQ ID NO: 3 for about four weeks; and thereafter
- b) administering to said patient a second titration dose of that GIP:GLP-1 Peptide for about four weeks; and thereafter
- c) administering to said patient a third titration dose of that GIP:GLP-1 Peptide for about four weeks; and thereafter
- d) administering to said patient a fourth titration dose of that GIP:GLP-1 Peptide for about four weeks; and thereafter
- e) administering to said patient a fifth titration dose of that GIP:GLP-1 Peptide for about four weeks; and thereafter
- f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In embodiment 10, the GIP:GLP-1 Peptide of embodiments 1 (a)-(c), 2 (a)-(c), 3 (a)-(c), 4 (a)-(c), 5 (a)-(c), 6 (a)-(c), 7 (a)-(c), 8 or 9 has a receptor agonist potency ratio that is 2.5:1 to about 5:1 GIP to GLP-1.

In embodiment 11, the GIP:GLP-1 Peptide of embodiments 1 (a)-(c), 2 (a)-(c), 3 (a)-(c), 4 (a)-(c), 5 (a)-(c), 6 (a)-(c), 7 (a)-(c), 8, 9 or 10 has a receptor agonist potency ratio that is 2.5:1 to about 3.5:1 GIP to GLP-1.

In an embodiment 12 (a), the present invention provides the use of a GIP:GLP-1 Peptide, or a pharmaceutically acceptable salt thereof, in the manufacture of a medicament for treating type 2 diabetes in a patient in need thereof, comprising:
- a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a maintenance dose of that GIP:GLP-1 Peptide;

wherein the titration dose is about 50% of the maintenance dose.

In an embodiment 12 (b), the present invention provides the use of a GIP:GLP-1 Peptide, or a pharmaceutically acceptable salt thereof, in the manufacture of a medicament for treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In an embodiment 12 (c), the present invention provides the use of a GIP:GLP-1 Peptide, or a pharmaceutically acceptable salt thereof, in the manufacture of a medicament for treating type 2 diabetes in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a fourth titration dose of that GIP:GLP-1 Peptide for a minimum of about two weeks; and thereafter
- e) administering to said patient a fifth titration dose of that GIP:GLP-1 Peptide for a minimum of about two weeks; and thereafter
- f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 13 (a), the present invention provides the use of a GIP:GLP-1 Peptide, or a pharmaceutically acceptable salt thereof, in the manufacture of a medicament for improving glycemic control in a patient in need thereof, comprising:
- a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a maintenance dose of that GIP:GLP-1 Peptide;
  - wherein the titration dose is about 50% of the maintenance dose.

In an embodiment 13 (b), the present invention provides the use of a GIP:GLP-1 Peptide, or a pharmaceutically acceptable salt thereof, in the manufacture of a medicament for improving glycemic control in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a maintenance dose of that GIP:GLP-1 Peptide;
  - wherein the first titration dose is about 25% of the maintenance dose, the second titration dose is about 50% of the maintenance dose and the third titration dose is about 75% of the maintenance dose.

In an embodiment 13 (c), the present invention provides the use of a GIP:GLP-1 Peptide, or a pharmaceutically acceptable salt thereof, in the manufacture of a medicament for improving glycemic control in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a fourth titration dose of that GIP:GLP-1 Peptide for a minimum of about two weeks; and thereafter
- e) administering to said patient a fifth titration dose of that GIP:GLP-1 Peptide for a minimum of about two weeks; and thereafter
- f) administering to said patient a maintenance dose of that GIP:GLP-1 Peptide;
  - wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 14 (a), the present invention provides the use of a GIP:GLP-1 Peptide, or a pharmaceutically acceptable salt thereof, in the manufacture of a medicament for improving weight management in a patient in need thereof, comprising:
- a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a maintenance dose of that GIP:GLP-1 Peptide;
  - wherein the titration dose is about 50% of the maintenance dose.

In an embodiment 14 (b), the present invention provides the use of a GIP:GLP-1 Peptide, or a pharmaceutically acceptable salt thereof, in the manufacture of a medicament for improving weight management in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a maintenance dose of that GIP:GLP-1 Peptide;
  - wherein the first titration dose is about 25% of the maintenance dose, the second titration dose is about 50% of the maintenance dose and the third titration dose is about 75% of the maintenance dose.

In an embodiment 14 (c), the present invention provides the use of a GIP:GLP-1 Peptide, or a pharmaceutically acceptable salt thereof, in the manufacture of a medicament for improving weight management in a patient in need thereof, comprising:
- a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administering to said patient a second titration dose of that GIP:GLP-1 Peptide for a minimum of about two weeks; and thereafter
- c) administering to said patient a third titration dose of that GIP:GLP-1 Peptide for a minimum of about two weeks; and thereafter
- d) administering to said patient a fourth titration dose of that GIP:GLP-1 Peptide for a minimum of about two weeks; and thereafter
- e) administering to said patient a fifth titration dose of that GIP:GLP-1 Peptide for a minimum of about two weeks; and thereafter
- f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 15 (a), the present invention provides the use of a GIP:GLP-1 Peptide, or a pharmaceutically acceptable salt thereof, in the manufacture of a medicament for treating chronic kidney disease in a patient in need thereof, comprising:
  a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a maintenance dose of that GIP:GLP-1 Peptide;
    wherein the titration dose is about 50% of the maintenance dose.

In an embodiment 15 (b), the present invention provides the use of a GIP:GLP-1 Peptide, or a pharmaceutically acceptable salt thereof, in the manufacture of a medicament for treating chronic kidney disease in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a maintenance dose of that GIP:GLP-1 Peptide;
    wherein the first titration dose is about 25% of the maintenance dose, the second titration dose is about 50% of the maintenance dose and the third titration dose is about 75% of the maintenance dose.

In an embodiment 15 (c), the present invention provides the use of a GIP:GLP-1 Peptide, or a pharmaceutically acceptable salt thereof, in the manufacture of a medicament for treating chronic kidney disease in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a fourth titration dose of that GIP:GLP-1 Peptide for a minimum of about two weeks; and thereafter
  e) administering to said patient a fifth titration dose of that GIP:GLP-1 Peptide for a minimum of about two weeks; and thereafter
  f) administering to said patient a maintenance dose of that GIP:GLP-1 Peptide;
    wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 16 (a), the present invention provides the use of a GIP:GLP-1 Peptide, or a pharmaceutically acceptable salt thereof, in the manufacture of a medicament for treating NAFLD in a patient in need thereof, comprising:
  a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a maintenance dose of that GIP:GLP-1 Peptide;
    wherein the titration dose is about 50% of the maintenance dose.

In an embodiment 16 (b), the present invention provides the use of a GIP:GLP-1 Peptide, or a pharmaceutically acceptable salt thereof, in the manufacture of a medicament for treating NAFLD in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a maintenance dose of that GIP:GLP-1 Peptide;
    wherein the first titration dose is about 25% of the maintenance dose, the second titration dose is about 50% of the maintenance dose and the third titration dose is about 75% of the maintenance dose.

In an embodiment 16 (c), the present invention provides the use of a GIP:GLP-1 Peptide, or a pharmaceutically acceptable salt thereof, in the manufacture of a medicament for treating NAFLD in a patient in need thereof, comprising:
  a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
  b) administering to said patient a second titration dose of that GIP:GLP-1 Peptide for a minimum of about two weeks; and thereafter
  c) administering to said patient a third titration dose of that GIP:GLP-1 Peptide for a minimum of about two weeks; and thereafter
  d) administering to said patient a fourth titration dose of that GIP:GLP-1 Peptide for a minimum of about two weeks; and thereafter e) administering to said patient a fifth titration dose of that GIP:GLP-1 Peptide for a minimum of about two weeks; and thereafter f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 17 (a), the present invention provides the use of a GIP:GLP-1 Peptide, or a pharmaceutically acceptable salt thereof, in the manufacture of a medicament for treating NASH in a patient in need thereof, comprising:

a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a maintenance dose of that GIP:GLP-1 Peptide;

wherein the titration dose is about 50% of the maintenance dose.

In an embodiment 17 (b), the present invention provides the use of a GIP:GLP-1 Peptide, or a pharmaceutically acceptable salt thereof, in the manufacture of a medicament for treating NASH in a patient in need thereof, comprising:

a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a second titration dose of that GIP:GLP-1 Peptide for a minimum of about two weeks; and thereafter c) administering to said patient a third titration dose of that GIP:GLP-1 Peptide for a minimum of about two weeks; and thereafter d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In an embodiment 17 (c), the present invention provides the use of a GIP:GLP-1 Peptide, or a pharmaceutically acceptable salt thereof, in the manufacture of a medicament for treating NASH in a patient in need thereof, comprising:

a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a second titration dose of that GIP:GLP-1 Peptide for a minimum of about two weeks; and thereafter c) administering to said patient a third titration dose of that GIP:GLP-1 Peptide for a minimum of about two weeks; and thereafter d) administering to said patient a fourth titration dose of that GIP:GLP-1 Peptide for a minimum of about two weeks; and thereafter e) administering to said patient a fifth titration dose of that GIP:GLP-1 Peptide for a minimum of about two weeks; and thereafter f) administering to said patient a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 18 (a), the present invention provides the use of a GIP:GLP-1 Peptide, or a pharmaceutically acceptable salt thereof, in the manufacture of a medicament for inducing remission or regression of diabetes, or preventing diabetes in a patient in need thereof, comprising:

a) administering to said patient a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a maintenance dose of that GIP:GLP-1 Peptide;

wherein the titration dose is about 50% of the maintenance dose.

In an embodiment 18 (b), the present invention provides the use of a GIP:GLP-1 Peptide, or a pharmaceutically acceptable salt thereof, in the manufacture of a medicament for inducing remission or regression of diabetes, or preventing diabetes in a patient in need thereof, comprising:

a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a second titration dose of that GIP:GLP-1 Peptide for a minimum of about two weeks; and thereafter c) administering to said patient a third titration dose of that GIP:GLP-1 Peptide for a minimum of about two weeks; and thereafter d) administering to said patient a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In an embodiment 18 (c), the present invention provides the use of a GIP:GLP-1 Peptide, or a pharmaceutically acceptable salt thereof, in the manufacture of a medicament for inducing remission or regression of diabetes, or preventing diabetes in a patient in need thereof, comprising:

a) administering to said patient a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter b) administering to said patient a second titration dose of that GIP:GLP-1 Peptide for a minimum of about two weeks; and thereafter c) administering to said patient a third titration dose of that GIP:GLP-1 Peptide for a minimum of about two weeks; and thereafter d) administering to said patient a fourth titration dose of that GIP:GLP-1 Peptide for a minimum of about two weeks; and thereafter
e) administering to said patient a fifth titration dose of that GIP:GLP-1 Peptide for a minimum of about two weeks; and thereafter
f) administering to said patient a maintenance dose of that GIP:GLP-1 Peptide;
wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In embodiment 19, the titration doses of any of embodiments 12 (a)-(c), 13 (a)-(c), 14 (a)-(c), 15 (a)-(c), 16 (a)-(c), 17 (a)-(c), or 18 (a)-(c) are each administered for about four weeks before the administration of the next higher dose begins.

In embodiment 20, the GIP:GLP-1 Peptide of any of embodiments 12 (a)-(c), 13 (a)-(c), 14 (a)-(c), 15 (a)-(c), 16 (a)-(c), 17 (a)-(c), 18 (a)-(c), or 19 is a peptide of SEQ ID NO: 3, or a pharmaceutically acceptable salt thereof.

In embodiment 21, the GIP:GLP-1 Peptide of any of embodiments 12 (a)-(c), 13 (a)-(c), 14 (a)-(c), 15 (a)-(c), 16 (a)-(c), 17 (a)-(c), 18 (a)-(c), 19 or 20 has a receptor agonist potency ratio that is 2.5:1 to about 5:1 GIP to GLP-1.

In embodiment 22, the GIP:GLP-1 Peptide of any of embodiments 12 (a)-(c), 13 (a)-(c), 14 (a)-(c), 15 (a)-(c), 16 (a)-(c), 17 (a)-(c), 18 (a)-(c), 19, or 20 has a receptor agonist potency ratio that is 2.5:1 to about 3.5:1 GIP to GLP-1.

In an embodiment 23 (a), the present invention provides a GIP:GLP-1 Peptide, or a pharmaceutically acceptable salt thereof, for use in treating type 2 diabetes in a patient in need thereof wherein the use comprises:
a) administration of a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a maintenance dose of that GIP:GLP-1 Peptide;
wherein the titration dose is about 50% of the maintenance dose.

In an embodiment 23 (b), the present invention provides a GIP:GLP-1 Peptide, or a pharmaceutically acceptable salt thereof, for use in treating type 2 diabetes in a patient in need thereof wherein the use comprises:
a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a second titration dose of that GIP:GLP-1 Peptide for a minimum of about two weeks; and thereafter
c) administration of a third titration dose of that GIP:GLP-1 Peptide for a minimum of about two weeks; and thereafter
d) administration of a maintenance dose of that GIP:GLP-1 Peptide;
wherein the first titration dose is about 25% of the maintenance dose, the second titration dose is about 50% of the maintenance dose and the third titration dose is about 75% of the maintenance dose.

In an embodiment 23 (c), the present invention provides a GIP:GLP-1 Peptide, or a pharmaceutically acceptable salt thereof, for use in treating type 2 diabetes in a patient in need thereof wherein the use comprises:
a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a second titration dose of that GIP:GLP-1 Peptide for a minimum of about two weeks; and thereafter
c) administration of a third titration dose of that GIP:GLP-1 Peptide for a minimum of about two weeks; and thereafter
d) administration of a fourth titration dose of that GIP:GLP-1 Peptide for a minimum of about two weeks; and thereafter
e) administration of a fifth titration dose of that GIP:GLP-1 Peptide for a minimum of about two weeks; and thereafter
f) administration of a maintenance dose of that GIP:GLP-1 Peptide;
wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 24 (a), the present invention provides a GIP:GLP-1 Peptide, or a pharmaceutically acceptable salt thereof, for use in improving glycemic control in a patient in need thereof wherein the use comprises:
a) administration of a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a maintenance dose of that GIP:GLP-1 Peptide;
wherein the titration dose is about 50% of the maintenance dose.

In an embodiment 24 (b), the present invention provides a GIP:GLP-1 Peptide, or a pharmaceutically acceptable salt thereof, for use in improving glycemic control in a patient in need thereof wherein the use comprises:
a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a second titration dose of that GIP:GLP-1 Peptide for a minimum of about two weeks; and thereafter
c) administration of a third titration dose of that GIP:GLP-1 Peptide for a minimum of about two weeks; and thereafter
d) administration of a maintenance dose of that GIP:GLP-1 Peptide;
wherein the first titration dose is about 25% of the maintenance dose, the second titration dose is about 50% of the maintenance dose and the third titration dose is about 75% of the maintenance dose.

In an embodiment 24 (c), the present invention provides a GIP:GLP-1 Peptide, or a pharmaceutically acceptable salt thereof, for use in improving glycemic control in a patient in need thereof wherein the use comprises:
- a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administration of a second titration dose of that GIP:GLP-1 Peptide for a minimum of about two weeks; and thereafter
- c) administration of a third titration dose of that GIP:GLP-1 Peptide for a minimum of about two weeks; and thereafter
- d) administration of a fourth titration dose of that GIP:GLP-1 Peptide for a minimum of about two weeks; and thereafter
- e) administration of a fifth titration dose of that GIP:GLP-1 Peptide for a minimum of about two weeks; and thereafter
- f) administration of a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 25 (a), the present invention provides a GIP:GLP-1 Peptide, or a pharmaceutically acceptable salt thereof, for use in improving weight management in a patient in need thereof wherein the use comprises:
- a) administration of a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administration of a maintenance dose of that GIP:GLP-1 Peptide;

wherein the titration dose is about 50% of the maintenance dose.

In an embodiment 25 (b), the present invention provides a GIP:GLP-1 Peptide, or a pharmaceutically acceptable salt thereof, for use in improving weight management in a patient in need thereof wherein the use comprises:
- a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administration of a second titration dose of that GIP:GLP-1 Peptide for a minimum of about two weeks; and thereafter
- c) administration of a third titration dose of that GIP:GLP-1 Peptide for a minimum of about two weeks; and thereafter
- d) administration of a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In an embodiment 25 (c), the present invention provides a GIP:GLP-1 Peptide, or a pharmaceutically acceptable salt thereof, for use in improving weight management in a patient in need thereof wherein the use comprises:
- a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administration of a second titration dose of that GIP:GLP-1 Peptide for a minimum of about two weeks; and thereafter
- c) administration of a third titration dose of that GIP:GLP-1 Peptide for a minimum of about two weeks; and thereafter
- d) administration of a fourth titration dose of that GIP:GLP-1 Peptide for a minimum of about two weeks; and thereafter
- e) administration of a fifth titration dose of that GIP:GLP-1 Peptide for a minimum of about two weeks; and thereafter
- f) administration of a maintenance dose of that GIP:GLP-1 Peptide;

wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 26 (a), the present invention provides a GIP:GLP-1 Peptide, or a pharmaceutically acceptable salt thereof, for use in treating chronic kidney disease in a patient in need thereof wherein the use comprises:
- a) administration of a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administration of a maintenance dose of that GIP:GLP-1 Peptide;

wherein the titration dose is about 50% of the maintenance dose.

In an embodiment 26 (b), the present invention provides a GIP:GLP-1 Peptide, or a pharmaceutically acceptable salt thereof, for use in treating chronic kidney disease in a patient in need thereof wherein the use comprises:
- a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
- b) administration of a second titration dose of that GIP:GLP-1 Peptide for a minimum of about two weeks; and thereafter
- c) administration of a third titration dose of that GIP:GLP-1 Peptide for a minimum of about two weeks; and thereafter
- d) administration of a maintenance dose of that GIP:GLP-1 Peptide;

wherein the first titration dose is about 25% of the maintenance dose, the second titration dose is about 50% of the maintenance dose and the third titration dose is about 75% of the maintenance dose.

In an embodiment 26 (c), the present invention provides a GIP:GLP-1 Peptide, or a pharmaceutically acceptable salt thereof, for use in treating chronic kidney disease in a patient in need thereof wherein the use comprises:
a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a second titration dose of that GIP:GLP-1 Peptide for a minimum of about two weeks; and thereafter
c) administration of a third titration dose of that GIP:GLP-1 Peptide for a minimum of about two weeks; and thereafter
d) administration of a fourth titration dose of that GIP:GLP-1 Peptide for a minimum of about two weeks; and thereafter
e) administration of a fifth titration dose of that GIP:GLP-1 Peptide for a minimum of about two weeks; and thereafter
f) administration of a maintenance dose of that GIP:GLP-1 Peptide;
wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 27 (a), the present invention provides a GIP:GLP-1 Peptide, or a pharmaceutically acceptable salt thereof, for use in treating NAFLD in a patient in need thereof wherein the use comprises:
a) administration of a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a maintenance dose of that GIP:GLP-1 Peptide;
wherein the titration dose is about 50% of the maintenance dose.

In an embodiment 27 (b), the present invention provides a GIP:GLP-1 Peptide, or a pharmaceutically acceptable salt thereof, for use in treating NAFLD in a patient in need thereof wherein the use comprises:
a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a second titration dose of that GIP:GLP-1 Peptide for a minimum of about two weeks; and thereafter
c) administration of a third titration dose of that GIP:GLP-1 Peptide for a minimum of about two weeks; and thereafter
d) administration of a maintenance dose of that GIP:GLP-1 Peptide;
wherein the first titration dose is about 25% of the maintenance dose, the second titration dose is about 50% of the maintenance dose and the third titration dose is about 75% of the maintenance dose.

In an embodiment 27 (c), the present invention provides a GIP:GLP-1 Peptide, or a pharmaceutically acceptable salt thereof, for use in treating NAFLD in a patient in need thereof wherein the use comprises:
a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a second titration dose of that GIP:GLP-1 Peptide for a minimum of about two weeks; and thereafter
c) administration of a third titration dose of that GIP:GLP-1 Peptide for a minimum of about two weeks; and thereafter
d) administration of a fourth titration dose of that GIP:GLP-1 Peptide for a minimum of about two weeks; and thereafter
e) administration of a fifth titration dose of that GIP:GLP-1 Peptide for a minimum of about two weeks; and thereafter
f) administration of a maintenance dose of that GIP:GLP-1 Peptide;
wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 28 (a), the present invention provides a GIP:GLP-1 Peptide, or a pharmaceutically acceptable salt thereof, for use in treating NASH in a patient in need thereof wherein the use comprises:
a) administration of a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a maintenance dose of that GIP:GLP-1 Peptide;
wherein the titration dose is about 50% of the maintenance dose.

In an embodiment 28 (b), the present invention provides a GIP:GLP-1 Peptide, or a pharmaceutically acceptable salt thereof, for use in treating NASH in a patient in need thereof wherein the use comprises:
a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
b) administration of a second titration dose of that GIP:GLP-1 Peptide for a minimum of about two weeks; and thereafter
c) administration of a third titration dose of that GIP:GLP-1 Peptide for a minimum of about two weeks; and thereafter
d) administration of a maintenance dose of that GIP:GLP-1 Peptide;
wherein the first titration dose is about 25% of the maintenance dose, the second titration dose is about 50% of the maintenance dose and the third titration dose is about 75% of the maintenance dose.

In an embodiment 28 (c), the present invention provides a GIP:GLP-1 Peptide, or a pharmaceutically acceptable salt thereof, for use in treating NASH in a patient in need thereof wherein the use comprises:
 a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
 b) administration of a second titration dose of that GIP:GLP-1 Peptide for a minimum of about two weeks; and thereafter
 c) administration of a third titration dose of that GIP:GLP-1 Peptide for a minimum of about two weeks; and thereafter
 d) administration of a fourth titration dose of that GIP:GLP-1 Peptide for a minimum of about two weeks; and thereafter
 e) administration of a fifth titration dose of that GIP:GLP-1 Peptide for a minimum of about two weeks; and thereafter
 f) administration of a maintenance dose of that GIP:GLP-1 Peptide;
 wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In an embodiment 29 (a), the present invention provides a GIP:GLP-1 Peptide, or a pharmaceutically acceptable salt thereof, for use in inducing remission or regression of diabetes, or preventing diabetes in a patient in need thereof wherein the use comprises:
 a) administration of a titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
 b) administration of a maintenance dose of that GIP:GLP-1 Peptide:
 wherein the titration dose is about 50% of the maintenance dose.

In an embodiment 29 (b), the present invention provides a GIP:GLP-1 Peptide, or a pharmaceutically acceptable salt thereof, for use in inducing remission or regression of diabetes, or preventing diabetes in a patient in need thereof wherein the use comprises:
 a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
 b) administration of a second titration dose of that GIP:GLP-1 Peptide for a minimum of about two weeks; and thereafter
 c) administration of a third titration dose of that GIP:GLP-1 Peptide for a minimum of about two weeks; and thereafter
 d) administration of a maintenance dose of that GIP:GLP-1 Peptide;
 wherein the first titration dose is about 25% of the maintenance dose, the second titration dose is about 50% of the maintenance dose and the third titration dose is about 75% of the maintenance dose.

In an embodiment 29 (c), the present invention provides a GIP:GLP-1 Peptide, or a pharmaceutically acceptable salt thereof, for use in inducing remission or regression of diabetes, or preventing diabetes in a patient in need thereof wherein the use comprises:
 a) administration of a first titration dose of a GIP:GLP-1 Peptide having a GIP:GLP-1 receptor agonist potency ratio as measured after a 60 minute incubation using a casein cAMP assay normalized against GIP and GLP-1 that is about 2.5:1 to about 10:1 for a minimum of about two weeks; and thereafter
 b) administration of a second titration dose of that GIP:GLP-1 Peptide for a minimum of about two weeks; and thereafter
 c) administration of a third titration dose of that GIP:GLP-1 Peptide for a minimum of about two weeks; and thereafter
 d) administration of a fourth titration dose of that GIP:GLP-1 Peptide for a minimum of about two weeks; and thereafter
 e) administration of a fifth titration dose of that GIP:GLP-1 Peptide for a minimum of about two weeks; and thereafter
 f) administration of a maintenance dose of that GIP:GLP-1 Peptide;
 wherein the first titration dose is about 17% of the maintenance dose, the second titration dose is about 33% of the maintenance dose, the third titration dose is about 50% of the maintenance dose, the fourth titration is about 66% of the maintenance dose and the fifth titration dose is about 83% of the maintenance dose.

In embodiment 30, the titration doses of any of embodiments 23 (a)-(c), 24 (a)-(c), 25 (a)-(c), 26 (a)-(c), 27 (a)-(c), 28 (a)-(c), or 29 (a)-(c) are each administered for about four weeks before the administration of the next higher dose begins.

In embodiment 31, the GIP:GLP-1 Peptide of any of embodiments 23 (a)-(c), 24 (a)-(c), 25 (a)-(c), 26 (a)-(c), 27 (a)-(c), 28 (a)-(c), 29 (a)-(c) or 30 is a peptide of SEQ ID NO: 3, or a pharmaceutically acceptable salt thereof.

In embodiment 32, the GIP:GLP-1 Peptide of any of embodiments 23 (a)-(c), 24 (a)-(c), 25 (a)-(c), 26 (a)-(c), 27 (a)-(c), 28 (a)-(c), 29 (a)-(c), 30, or 31 has a receptor agonist potency ratio that is 2.5:1 to about 5:1 GIP to GLP-1.

In embodiment 33, the GIP:GLP-1 Peptide of any of embodiments 23 (a)-(c), 24 (a)-(c), 25 (a)-(c), 26 (a)-(c), 27 (a)-(c), 28 (a)-(c), 29 (a)-(c), 30, or 31 has a receptor agonist potency ratio that is 2.5:1 to about 3.5:1 GIP to GLP-1.

In embodiment 34, is a composition comprising a GIP-GLP-1 Peptide having a GIP:GLP-1 receptor agonist potency ratio as measured after a 60 minute incubation using casein cAMP assay normalized against GIP and GLP-1 that is about 2.5:1 to about 10:1; and a pharmaceutically acceptable excipient.

In embodiment 34 (a) is a composition administered at least two weeks as an escalation dose.

In embodiment 34 (a1) is a composition administered at least two weeks as an escalation dose.

In embodiment 34 (b) is a composition administered as a maintenance dose for at least two weeks.

In embodiment 35, is a GIP-GLP-1 Peptide for use to treat diabetes in a patient in need thereof, wherein the GIP:GLP-1 receptor potency ratio of the GIP-GLP-1 Peptide, as measured after a 60 minute incubation using a casein cAMP assay normalized against GIP and GLP-1, is about 2.5:1 to about 10:1.

In embodiment 35 (a) is a GIP-GLP-1 Peptide of embodiment 35 wherein the Peptide is administred for a minimum of about 2 weeks.

In embodiment 35 (b) is a GIP-GLP-1 Peptide of embodiment 35 or 35 (a) wherein the Peptide is administered as at least one escalation dose for a minimum of about 2 weeks.

Also provided herein are methods of using a GIP:GLP-1 Peptide in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, a growth differentiation factor 15 modulator ("GDF15"), a peptide tyrosine tyrosine modulator ("PYY"), a modified insulin, amylin, a dual amylin calcitonin receptor agonist, and oxyntomodulin agonist ("OXM") in the treatment of a condition selected from the group consisting of type 2 diabetes, chronic kidney disease, atherosclerosis, NALFD and NASH. Further provided herein are methods of using a GIP:GLP-1 Peptide in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, GDF15, PYY, a modified insulin, amylin, a dual amylin calcitonin receptor agonist, and OXM in the improvement of glycemic control and/or weight management. Also provided herein are methods of using a GIP:GLP-1 Peptide in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, GDF15, PYY, a modified insulin, amylin, a dual amylin calcitonin receptor agonist, and OXM to cure diabetes, induce remission or regression of diabetes, or prevent diabetes. In an embodiment, a compound of the present invention is provided in a fixed dose combination with one or more agents selected from metformin, a thiazolidinedione, a sulfonylurea, a dipeptidyl peptidase 4 inhibitor, a sodium glucose co-transporter, a SGLT-2 inhibitor, GDF15, PYY, a modified insulin, amylin, a dual amylin calcitonin receptor agonist, and OXM.

The present invention provides novel dosing regimens that include administering a titration dose about once weekly for a minimum of about two weeks and thereafter administering a maintenance dose wherein the titration dose is about 50% of the maintenance dose. In certain embodiment, the titration dose may be administered for about four weeks. In certain embodiments, the titration dose may be administered for more than about four weeks as determined by the nurse, patient and/or health care provider.

As used herein, the term "treating" or "to treat" includes restraining, slowing, stopping, or reversing the progression or severity of a symptom, condition, or disorder.

As used herein, "normalized against GIP and GLP-1" means that the native peptides, as provided herein as SEQ ID NO:1 and SEQ ID NO:2, are tested in the casein CAMP assay as a control for the test compound, and Raw CPM data for concentration curves of peptides, GLP-1, or GIP are converted to percent inhibition by subtracting nonspecific binding (binding in the presence of excess unlabeled GLP-1, or GIP, respectively) from the individual CPM values and dividing by the total binding signal, also corrected by subtracting nonspecific binding. Data are analyzed using four-parameter (curve maximum, curve minimum, $IC_{50}$, Hill slope) nonlinear regression routines (Genedata Screener, version 12.0.4, Genedata AG, Basal, Switzerland).

GIP is a 42 amino acid peptide (SEQ ID NO:1), which, like GLP-1, is also known as an incretin, and plays a physiological role in glucose homeostasis by stimulating insulin secretion from pancreatic beta cells in the presence of glucose. GLP-1 is a 36 amino acid peptide, the major biologically active fragment of which ($GLP-1_{7-36}$) is produced as a 30-amino acid, C-terminal amidated peptide (SEQ ID NO:2).

The compounds of SEQ ID NO: 3 provide desired potency at each of the GIP and GLP-1 receptors. In an embodiment, compounds of SEQ ID NO: 3 have desirable GIP and GLP receptor activity wherein the GIP agonist potency is from about 2.5:1 to about 10 times the GLP1 receptor potency as measured by the casein cAMP assay, wherein the potency is normalized against native GIP and GLP on the day the assay is run. In an embodiment, compounds of SEQ ID NO: 3 have desirable GIP and GLP receptor activity wherein the GIP agonist potency is from about 2.5:1 to about 5 times the GLP1 receptor potency as measured by the casein cAMP assay, described herein below, wherein the potency is normalized against native GIP and GLP on the day the assay is run.

As used herein "maintenance dose" means an effective dose to treat the patient with a side-effect profile that supports chronic dosing. The term "effective dose" refers to the amount or dose of a GIP:GLP-1 Peptide, which, upon single or multiple dose administration to the patient, provides the desired effect in the patient under diagnosis or treatment. An effective doe can be determined by a person of skill in the art using the clinical trial descriptions set forth herein together with known techniques and by observing results obtained under analogous circumstances. In determining the effective amount for a subject, a number of factors are considered, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, the term "titration" or "titration dose(s)" also means and can be interchangable with an escalation or escalation dose(s).

As used herein, the term GIP to GLP-1 also means and can be interchangeable with GIP:GLP-1. Thus, when "about 2.5 to about 10:1 GIP to GLP-1" or "about 2.5:1 to about 10:1 GIP to GLP-1" is used, it also means about 2.5 to about 10 GIP activity to 1 GLP-1 activity or about 2.5 to about 10 GIP activity: 1 GLP-1 activity.

When used herein in reference to one or more of the GIP or GLP-1 receptors, the terms "activity," "activate[s]" "activat[ing]" and the like refers to the capacity of a compound to bind to and induce a response at the receptor(s), as measured using assays known in the art, such as the in vitro assays described below. Such activity may be measured in vivo using serum. The receptor agonist potency ratio of a GIP:GLP-1 Peptide is measured using the casein cAMP assay, as described herein below.

The affinity of a particular GIP:GLP-1 co-agonist compound for each of the GIP and GLP-1 receptors may be measured using techniques known for measuring receptor binding levels in the art, including, for example those described in the examples below, and is commonly expressed as a Ki value; however, the GIP potency ratio that is about 2.5 to about 10 times the receptor potentcy at the GLP-1 receptor determined using the casein cAMP assay, below.

In an embodiment, a pharmaceutical composition of a GIP:GLP-1 Peptide is suitable for administration by a parenteral route (e.g., subcutaneous, intravenous, intraperitoneal, intramuscular, or transdermal). In an embodiment, a pharmaceutical composition of a GIP:GLP-1 Peptide is suitable for oral administration (e.g., tablet, capsule). Such pharmaceutical compositions and processes for preparing same are generally well known in the art. (See, e.g., Remington: The Science and Practice of Pharmacy (D. B. Troy, Editor, 21st Edition, Lippincott, Williams & Wilkins, 2006). In an embodiment of the present invention, the route of administration is subcutaneous. In an embodiment of the present invention, the route of administration is oral.

As used herein "glycemic control" refers to the maintenance or reduction of a patient's HbA1c levels; "improving" glycemic control refers to reductions in HbA1c.

As used herein "weight management" refers to the management of obesity in an individual; "improving" weight management refers to a reduction in body weight.

As used herein "HbA1c" refers to glycated hemoglobin levels, which develop when hemoglobin joins with glucose in the blood. HbA1c levels are a commonly used measure of glycemic control in patients with diabetes, with decreased HbA1c levels generally indicating improved glycemic control. In the context of the methods of the present invention, the methods of the present invention result in a decrease in HbA1c. In certain embodiments, the decrease in HbA1c is decreased relative to the HbA1c levels resulting from treatment with a lower dose of a GIP:GLP-1 Peptide.

As used herein, the term "administering" means the administration by a nurse, health care provider, patient or any other individual including self-administration as directed by the doctor. This includes not only delivering into the body but also prescribing, dispensing or assisting in any way with delivery.

As used herein, the terms "treatment," "treat," "treating," and the like, mean to include slowing or attenuating the progression of a disease or disorder. The terms mean to alleviate, ameliorate, or reduce one or more symptoms of a disorder or condition, even if the disorder or condition is not eliminated. The term includes preventing the manifestation.

As used herein "diabetes remission" means that a patient, using a GIP:GLP-1 Peptide for the treatment of diabetes reaches their glycemic control treatment goal.

As used herein, the term GIP:GLP-1 Peptide is a compound, or a pharmaceutically acceptable salt thereof, with a GIP:GLP agonist potency ratio of from about 2.5:1 to about 10:1. The GIP:GLP-1 Peptide treatment to cure diabetes can prevent, reduce the severity of, or induce remission of diabetes in such patient. In an embodiment, a patient using a GIP:GLP-1 Peptide for treatment of diabetes, reaches their glycemic control treatment goal, and requires no concomitant diabetes medicine to maintain the glycemic control goal. In an embodiment, a patient using a GIP:GLP-1 Peptide in the treatment of diabetes reaches at least their glycemic control treatment goal, and the treatment goal is maintained with cessation of treatment using a GIP:GLP-1 Peptide and all other diabetes medication. In an embodiment, a patient using a GIP:GLP-1 Peptide in the treatment of diabetes reaches at least their glycemic control treatment goal, and the treatment goal is maintained for at least a about a month with cessation of treatment using a GIP:GLP-1 Peptide and all other diabetes medications. In an embodiment, a patient using a GIP:GLP-1 Peptide in the treatment of diabetes reaches at least their glycemic control treatment goal, and the treatment goal is maintained for at least about six months with cessation of treatment using a GIP:GLP-1 Peptide and all other diabetes medications. In an embodiment the patient is unable to reach their glycemic goals prior to a GIP:GLP-1 Peptide treatment. In an embodiment, the patient has failed to reach their glycemic goal using oral diabetes medication. In an embodiment, the patient has failed to reach their glycemic goal using metformin treatment. In an embodiment, the patient glycemic goal is less than about 5.7%.

As used herein "patient" or "patients" refers to a mammal in need of treatment for a condition or disorder. In an embodiment, the patient is a human with a disease or condition that would benefit from treatment with a GIP:GLP-1 Peptide having a GIP:GLP-1 receptor agonist potency ratio of from about 2.5:1 to about 10:1.

As used herein "EDTA" means ethylenediaminetetraacetic acid. As used herein "DMSO" means dimethyl sulfoxide. As used herein "CPM" means counts per minute. As used herein "IBMX" means 3-isobutyl-1-methylxanthine. As used herein "LC/MS" means liquid chromatography/mass spectrometry. As used herein "HTRF" means homogeneous time-resolved fluorescence. As used herein "BSA" mean bovine serum albumin.

Cure Diabetes, Induce Remission or Regression of Diabetes, or Prevent Diabetes

Despite advances in the treatment of diabetes, many patients receiving such treatment are unable to reach their glycemic control goal or HbA1c goal. This invention provides a cure for diabetes wherein a patient receiving treatment for diabetes using a GIP:GLP1 Peptide, is able to reach their HbA1c goal, and wherein such patient maintains their HbA1c goal after cessation of GIP:GLP1 Peptide treatment. In an embodiment, the patient receiving GIP:GLP1 Peptide treatment for diabetes maintains their HbA1c goal after cessation of all medications approved for use in the treatment of glycemic control or diabetes. As used herein, the term "diabetes medication," "diabetes medicine" and the like, means a medication approved by the pertinent regulatory agency for use in the treatment of glycemic control or Type II diabetes. In an embodiment, the HbA1c measurement in the patient treated for diabetes is less than or equal to about 5.9%. In an embodiment, the patient maintains their HbA1c goal level for at least one month without further GIP:GLP1 Peptide administration. In an embodiment, the patient previously treated for diabetes using GIP:GLP1 Peptide maintains their HbA1 goal level for at least one month without administration of further GIP:GLP1 Peptide or any other diabetes medication. In an embodiment, the patient maintains their HbA1c goal level for at least 6 months without administration of further GIP:GLP1 Peptide or any other diabetes medication.

As used herein the term "amino acid" means both naturally occurring amino acids and unnatural amino acids. The amino acids are typically depicted using standard one letter codes (e.g., L=leucine), as well as alpha-methyl substituted residues of natural amino acids (e.g., α-methyl leucine, or αMeL and α-methyl lysine, or αMeK) and certain other unnatural amino acids, such as alpha amino isobutyric acid, or "Aib," "4Pal," "Orn," and the like. The structures of these amino acids appear below:

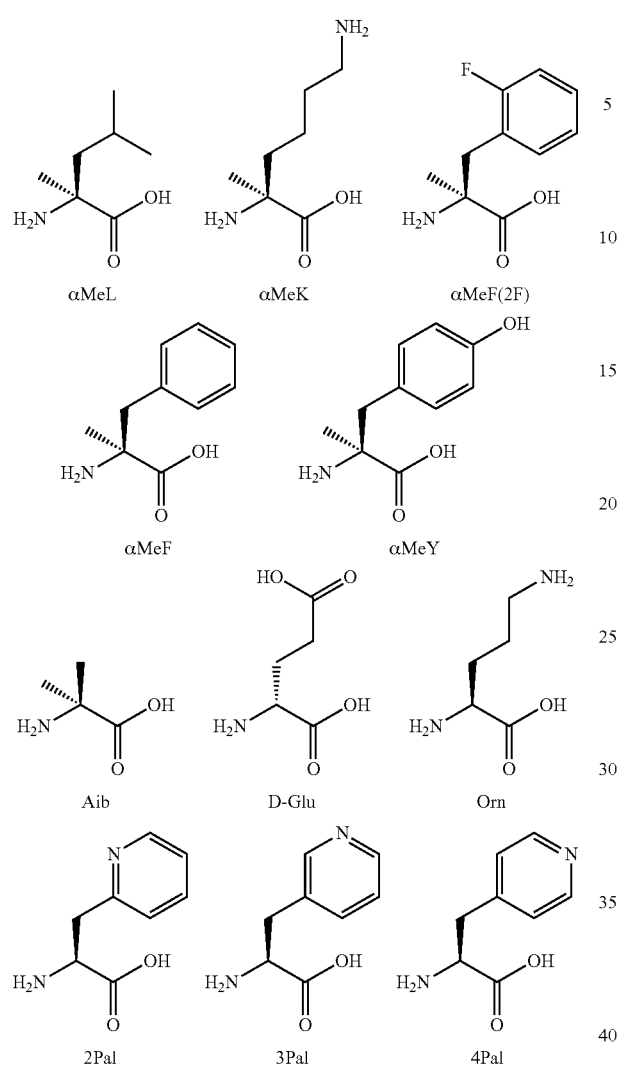

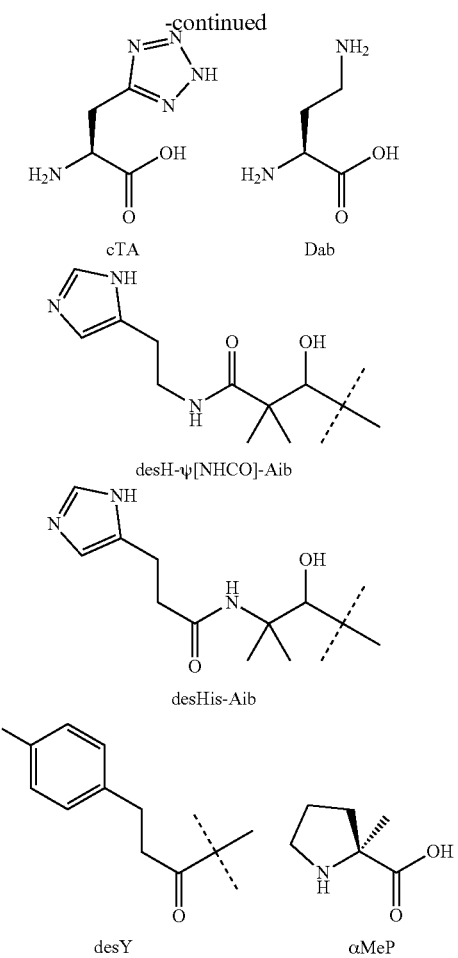

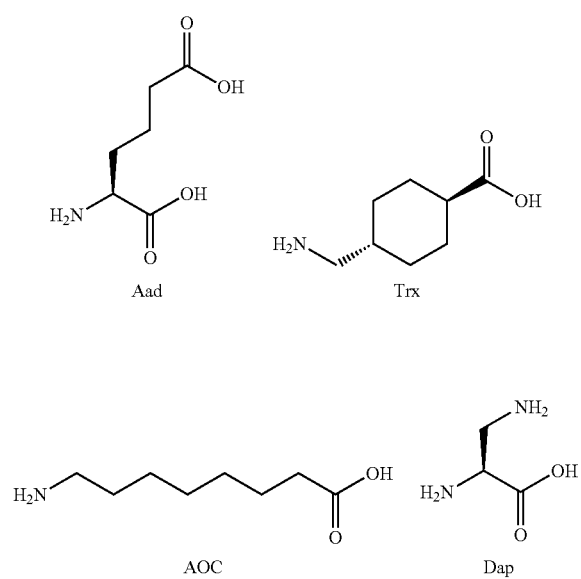

As used herein "Orn" means ornithine. As used herein "4Pal" means 3-(4-Pyridyl)-L-alanine. As used herein "αMeF(2F)" means alpha-methyl 2-Fl-phenylalanine. As used herein "αMeY," "αMeK," and "αMeL" mean alpha methyl tyrosine, alpha methyl lysine, and alpha methyl leucine, respectively. As used herein, "e" and "D-Glu" mean D-glutamic acid.

When used herein, the term "amino acid conjugated to a $C_{16}$-$C_{22}$ fatty acid" refers to any natural or unnatural amino acid with a functional group that has been chemically modified to conjugate to a fatty acid by way of a direct bond to the fatty acid or, preferably, by way of a linker. Examples of such functional groups include amino, carboxyl, chloro, bromo, iodo, azido, alkynyl, alkenyl, and thiol groups. Examples of natural amino acids which include such functional groups include K (amino), C (thiol), E (carboxyl) and D (carboxyl). In an embodiment the conjugated amino acid is K.

The term "$C_{16}$-$C_{22}$ fatty acid" as used herein means a carboxylic acid with between 16 and 22 carbon atoms. In an embodiment, the $C_{16}$-$C_{22}$ fatty acid suitable for use herein can be a saturated diacid. In an embodiment, the fatty acid is $C_{20}$-$C_{22}$. In an embodiment q is selected from the group consisting of 14, 16, 18, and 20. In an embodiment q is selected from 18 and 20. In an embodiment q is 18. In an embodiment q is 20.

In an embodiment, specific saturated $C_{16}$-$C_{22}$ fatty acids that are suitable for the compounds and uses thereof disclosed herein include, but are not limited to, hexadecanedioic acid (C$_{16}$ diacid), heptadecanedioic acid (C$_{17}$ diacid), octadecanedioic acid (C$_{18}$ diacid), nonadecanedioic acid (C$_{19}$ diacid), eicosanedioic acid (C$_{20}$ diacid), heneicosanedioic acid (C$_{21}$ diacid), docosanedioic acid (C$_{22}$ diacid), including branched and substituted derivatives thereof.

In an embodiment, the C$_{16}$-C$_{22}$ fatty acid is selected from the group consisting of a saturated C$_{18}$ diacid, a saturated C$_{19}$ diacid, a saturated C$_{20}$ diacid, and branched and substituted derivatives thereof. In an embodiment, the C$_{16}$-C$_{22}$ fatty acid is selected from the group consisting of stearic acid, arachadic acid and eicosanedioic acid. In an embodiment, the C$_{16}$-C$_{22}$ fatty acid is arachadic acid.

As used herein "time-extension technology" means a peptide time-extension technology for example, recombinant human serum albumin ("rHSA"), peptide conjugation to a pharmaceutically acceptable polymer, such as polymeric sequence of amino acids ("XTEN"), unsulfated heparin-like carbohydrate polymer ("HEP"), hydroxyl ethyl starch ("HES"), llama heavy-chain antibody fragments ("VHH"), pegylation, Fc conjugation, bovine serum albumin ("BSA") (Sleep, D. *Epert Opin Drug Del* (2015) 12, 793-812; Podust V N et. al. J Control. Release, 2015; ePUB; Hey, T. et. al. in: R. Kontermann (Ed.), Therapeutic Proteins: Strategies to Modulate their Plasma Half-Lives, Wiley-VCH Verlag Gmbh & Co. KGaA, Weinheim, Germany, 2012, pp 117-140; DeAngelis, P L, *Drug Dev Delivery* (2013) January, Dec. 31, 2012. In an embodiment time-extension technology is applied using a linker group. In an embodiment, the time-extension technology is applied using 0, 1, 2, or 3 amino acid as linker.

A compound having a GIP potency ratio that is about 2.5 to about 10 times the receptor potentcy at the GLP-1 receptor may be further modified using a peptide time-extension technology for example, recombinant human serum albumin ("rHSA"), peptide conjugation to a pharmaceutically acceptable polymer, such as polymeric sequence of amino acids ("XTEN"), unsulfated heparin-like carbohydrate polymer ("HEP"), and hydroxyl ethyl starch ("HES").

In an embodiment is a GIP:GLP-1 Peptide of the formula:

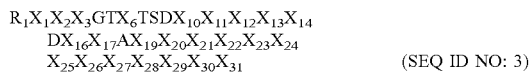

(SEQ ID NO: 3)

wherein:

R$_1$ is a modification of the N-terminal amino group wherein the modification is selected from the group consisting of Ac and absent;

X$_1$ is selected from the group consisting of Y, H, D-Tyr, F, desH, and desY,

X$_2$ is selected from the group consisting of Aib, αMeP, A, P, and D-Ala;

or X$_1$ and X$_2$ combine to form desH-ψ[NHCO]-Aib;

X$_3$ is selected from the group consisting of E, N, Aad, and cTA;

X$_6$ is selected from the group consisting of F, αMeF, and αMeF(2F);

X$_{10}$ is selected from the group consisting of A, L, H, 3Pal, 4Pal, V, Y, E, αMeF, αMeF(2F), I, αMeY, Q, D-His, D-Tyr, cTA, and K (2-[2-(2-amino-ethoxy)-ethoxy]-acetyl)$_2$-(γ-Glu)-CO—(CH$_2$)qCO$_2$H;

X$_{11}$ is selected from the group consisting of S, αMeS, and D-Ser;

X$_{12}$ is selected from the group consisting of I, S, D-Ile, and K (2-[2-(2-amino-ethoxy)-ethoxy]-acetyl)$_2$-(γ-Glu)-CO—(CH$_2$)qCO$_2$H;

X$_{13}$ is selected from the group consisting of Nle, Aib, L, αMeL, and K (2-[2-(2-amino-ethoxy)-ethoxy]-acetyl)$_2$-(γ-Glu)-CO—(CH$_2$)qCO$_2$H;

X$_{14}$ is selected from the group consisting of L and K, wherein K is conjugated to a C$_{16}$-C$_{22}$ fatty acid wherein said fatty acid is optionally conjugated to said K via a linker;

X$_{16}$ is selected from the group consisting of K, E, Orn, Dab, Dap, S, T, H, Aib, αMeK, R, and K (2-[2-(2-amino-ethoxy)-ethoxy]-acetyl)$_2$-(γ-Glu)-CO—(CH$_2$)qCO$_2$H;

X$_{17}$ is selected from the group consisting of K, Q, I, and an amino acid conjugated to a C$_{16}$-C$_{22}$ fatty acid wherein said fatty acid is optionally conjugated to said amino acid via a linker;

X$_{19}$ is selected from the group consisting of Q, A, and K (2-[2-(2-amino-ethoxy)-ethoxy]-acetyl)$_2$-(γ-Glu)-CO—(CH$_2$)qCO$_2$H;

X$_{20}$ is selected from the group consisting of Aib, Q, H, R, K, αMeK, and K (2-[2-(2-amino-ethoxy)-ethoxy]-acetyl)$_2$-(γ-Glu)-CO—(CH$_2$)qCO$_2$H;

X$_{21}$ is selected from the group consisting of H, Aad, D, Aib, T, A, E, I, and K (2-[2-(2-amino-ethoxy)-ethoxy]-acetyl)$_2$-(γ-Glu)-CO—(CH$_2$)qCO$_2$H;

X$_{22}$ is selected from the group consisting of F and αMeF;

X$_{23}$ is selected from the group consisting of I, L, A, G, F, H, E, V, and K (2-[2-(2-amino-ethoxy)-ethoxy]-acetyl)$_2$-(γ-Glu)-CO—(CH$_2$)qCO$_2$H;

X$_{24}$ is selected from the group consisting of S, Aad, D-Glu, E, Aib, H, V, A, Q, D, P, and K (2-[2-(2-amino-ethoxy)-ethoxy]-acetyl)$_2$-(γ-Glu)-CO—(CH$_2$)qCO$_2$H;

X$_{25}$ is selected from the group consisting of Y and αMeY;

X$_{26}$ is selected from the group consisting of L, αMeL, and K (2-[2-(2-amino-ethoxy)-ethoxy]-acetyl)$_2$-(γ-Glu)-CO—(CH$_2$)qCO$_2$H;

X$_{27}$ is selected from the group consisting of L, I, and K (2-[2-(2-amino-ethoxy)-ethoxy]-acetyl)$_2$-(γ-Glu)-CO—(CH$_2$)qCO$_2$H;

X$_{28}$ is selected from the group consisting of E, A, S, D-Glu, and K (2-[2-(2-amino-ethoxy)-ethoxy]-acetyl)$_2$-(γ-Glu)-CO—(CH$_2$)qCO$_2$H;

X$_{29}$ is selected from the group consisting of Aib, G, A, and K (2-[2-(2-amino-ethoxy)-ethoxy]-acetyl)$_2$-(γ-Glu)-CO—(CH$_2$)qCO$_2$H;

X$_{30}$ is selected from the group consisting of C, G, G-R$_2$ and K (2-[2-(2-amino-ethoxy)-ethoxy]-acetyl)$_2$-(γ-Glu)-CO—(CH$_2$)$_q$—CO$_2$H;

X$_{31}$ is absent or is selected from the group consisting of PX$_{32}$X$_{33}$X$_{34}$—R$_2$ (SEQ ID NO: 4), PX$_{32}$X$_{33}$X$_{34}$X$_{35}$X$_{36}$X$_{37}$X$_{38}$X$_{39}$—R$_2$ (SEQ ID NO:5), PX$_{32}$X$_{33}$X$_{34}$X$_{35}$X$_{36}$X$_{37}$X$_{38}$X$_{39}$X$_{40}$—R$_2$ (SEQ ID NO:6), K [(2-[2-(2-amino-ethoxy)-ethoxy]-acetyl)$_2$-(γ-Glu)-CO—(CH$_2$)$_q$CO$_2$H] X$_{32}$X$_{33}$X$_{34}$—R$_2$ (SEQ ID NO:7), K [(2-[2-(2-amino-ethoxy)-ethoxy]-acetyl)$_2$-(γ-Glu)-CO—(CH$_2$)$_q$—CO$_2$H] X$_{32}$X$_{33}$X$_{34}$X$_{35}$X$_{36}$X$_{37}$X$_{38}$X$_{39}$—R$_2$ (SEQ ID NO:8), and K [(2-[2-(2-amino-ethoxy)-ethoxy]-acetyl)$_2$-(γ-Glu)-CO—(CH$_2$)$_q$—CO$_2$H] X$_{32}$X$_{33}$X$_{34}$X$_{35}$X$_{36}$X$_{37}$X$_{38}$X$_{39}$X$_{40}$—R$_2$ (SEQ ID NO:9);

wherein:

X$_{32}$ is S or K [(2-[2-(2-amino-ethoxy)-ethoxy]-acetyl)$_2$-(γ-Glu)-CO—(CH$_2$)$_q$—CO$_2$H];

X$_{33}$ is S or K [(2-[2-(2-amino-ethoxy)-ethoxy]-acetyl)$_2$-(γ-Glu)-CO—(CH$_2$)$_q$—CO$_2$H];

$X_{34}$ is selected from the group consisting of G, C, and K [(2-[2-(2-amino-ethoxy)-ethoxy]-acetyl)$_2$-(γ-Glu)-CO—(CH$_2$)$_q$—CO$_2$H];

$X_{35}$ is A or K [(2-[2-(2-amino-ethoxy)-ethoxy]-acetyl)$_2$-(γ-Glu)-CO—(CH$_2$)$_q$—CO$_2$H];

$X_{36}$ is P or K [(2-[2-(2-amino-ethoxy)-ethoxy]-acetyl)$_2$-(γ-Glu)-CO—(CH$_2$)$_q$—CO$_2$H];

$X_{37}$ is P or K [(2-[2-(2-amino-ethoxy)-ethoxy]-acetyl)$_2$-(γ-Glu)-CO—(CH$_2$)$_q$—CO$_2$H];

$X_{38}$ is P or K [(2-[2-(2-amino-ethoxy)-ethoxy]-acetyl)$_2$-(γ-Glu)-CO—(CH$_2$)$_q$—CO$_2$H];

$X_{39}$ is selected from the group consisting of C, S, and K [(2-[2-(2-amino-ethoxy)-ethoxy]-acetyl)$_2$-(γ-Glu)-CO—(CH$_2$)$_q$—CO$_2$H];

$X_{40}$ is selected from the group consisting of C and K [(2-[2-(2-amino-ethoxy)-ethoxy]-acetyl)$_2$-(γ-Glu)-CO—(CH$_2$)$_q$—CO$_2$H];

q is selected from the group consisting of 14, 15, 16, 17, 18, 19, and 20; and $R_2$ is a modification of the C-terminal group, wherein the modification is NH$_2$ or absent;

or a pharmaceutically acceptable salt thereof;

wherein if $X_{30}$ is G-$R_2$, then $X_{31}$ is absent;

wherein no more than one of $X_{10}$, $X_{12}$, $X_{13}$, $X_{14}$, $X_{16}$, $X_{17}$, $X_{19}$, $X_{20}$, $X_{21}$, $X_{23}$, $X_{24}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$, $X_{37}$, $X_{38}$, $X_{39}$, and $X_{40}$ may be a substituent that contains a fatty acid; and wherein no more than one of $X_{30}$, $X_{34}$, $X_{39}$, and $X_{40}$ may be C; and wherein if one of $X_{30}$, $X_{34}$, $X_{39}$, and $X_{40}$ is C, then none of $X_{10}$, $X_{12}$, $X_{13}$, $X_{14}$, $X_{16}$, $X_{17}$, $X_{19}$, $X_{20}$, $X_{21}$, $X_{23}$, $X_{24}$, $X_{26}$, $X_{27}$, $X_{28}$, $X_{29}$, $X_{30}$, $X_{31}$, $X_{32}$, $X_{33}$, $X_{34}$, $X_{35}$, $X_{36}$, $X_{37}$, $X_{38}$, $X_{39}$, and $X_{40}$ is a substituent that contains a fatty acid;

wherein the GIP:GLP-1 Peptide has a receptor agonist potency ratio that is about 2.5:1 to about 10:1.

A further embodiment provides a novel GIP:GLP-1 Peptide of SEQ ID NO:3, wherein the GIP:GLP-1 Peptide has a GIP:GLP-1 receptor agonist potency ratio that is about 2.5:1 to about 5:1. A further embodiment of the present invention is a novel GIP:GLP-1 Peptide of SEQ ID NO:3, wherein the GIP:GLP-1 Peptide has a GIP:GLP-1 receptor agonist potency ratio that is about 2.5:1 to about 3.5:1.

The invention is further illustrated by the following compounds demonstrating the desired GIP potency ratio that is about 2.5:1 to about 10 times greater than the receptor potentcy at the GLP-1 receptor using the CAMP casein assay, however, these example peptides are not to be construed as limiting.

Peptide Synthesis—Peptide 1

Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ (SEQ ID NO:10).

The structure of SEQ ID NO: 10 is depicted below using the standard single letter amino acid codes with the exception of residues Aib2, αMeF(2F) 6, αMeL13, K17, Aib20, D-Glu24, and Ser39 where the structures of these amino acid residues have been expanded:

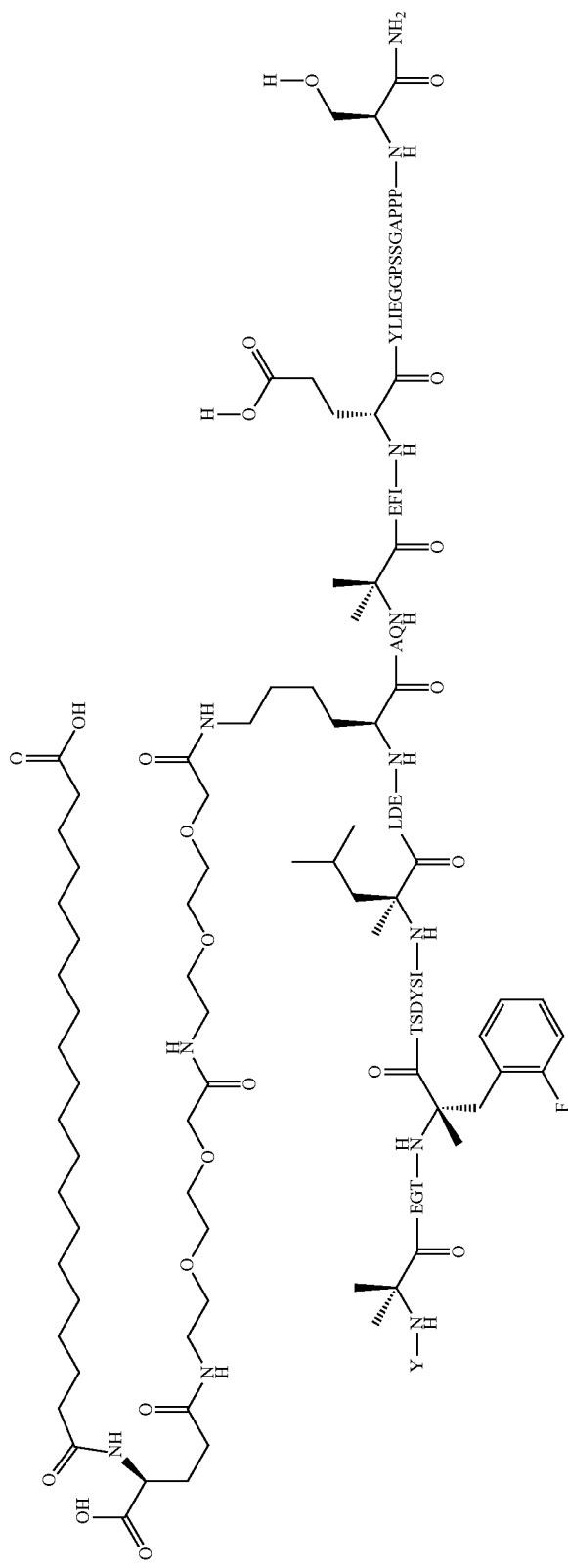

The peptide backbone of Peptide 1 is synthesized using Fluorenylmethyloxycarbonyl (Fmoc)/tert-Butyl (t-Bu) chemistry on a Symphony X peptide synthesizer (Gyros Protein Technologies. Tucson, AZ).

The resin consists of 1% DVB cross-linked polystyrene (Fmoc-Rink-MBHA Low Loading resin, 100-200 mesh, EMD Millipore) at a substitution of 0.3-0.4 meq/g. Standard side-chain protecting groups were used. Fmoc-Lys (Mtt)-OH is used for the lysine at position 17 and Boc-Tyr (tBu)-OH was used for the tyrosine at position 1 Fmoc groups are removed prior to each coupling step (2×7 minutes) using 20% piperidine in DMF. All standard amino acid couplings are performed for 1 hour to a primary amine and 3 hour to a secondary amine, using an equal molar ratio of Fmoc amino acid (0.3 mM), diisopropylcarbodiimide (0.9 mM) and Oxyma (0.9 mM), at a 9-fold molar excess over the theoretical peptide loading. Exceptions are couplings to Ca-methylated amino acids, which are coupled for 3 hours. After completion of the synthesis of the peptide backbone, the resin is thoroughly washed with DCM for 6 times to remove residual DMF. The Mtt protecting group on the lysine at position 17 is selectively removed from the peptide resin using two treatments of 30% hexafluoroisopropanol (Oakwood Chemicals) in DCM (2×40-minute treatment).

Subsequent attachment of the fatty acid-linker moiety is accomplished by coupling of 2-[2-(2-Fmoc-amino-ethoxy)-ethoxy]-acetic acid (Fmoc-AEEA-OH, ChemPep, Inc.), Fmoc-glutamic acid α-t-butyl ester (Fmoc-Glu-OtBu, Ark Pharm, Inc.), eicosanedioic acid (WuXi AppTec, Shanghai, China). 3-Fold excess of reagents (AA:PyAOP:DIPEA=1:1:1 mol/mol) are used for each coupling that is 1-hour long.

After the synthesis is complete, the peptide resin is washed with DCM, and then thoroughly air-dried. The dry resin is treated with 10 mL of cleavage cocktail (trifluoroacetic acid:water:triisopropylsilane, 95:2.5:2.5 v/v) for 2 hours at room temperature. The resin is filtered off, washed twice each with 2 mL of neat TFA, and the combined filtrates are treated with 5-fold excess volume of cold diethyl ether (−20° C.) to precipitate the crude peptide. The peptide/ether suspension is then centrifuged at 3500 rpm for 2 min to form a solid pellet, the supernatant is decanted, and the solid pellet is triturated with ether two additional times and dried in vacuo. The crude peptide is solubilized in 20% acetonitrile/20% Acetic acid/60% water and purified by RP-HPLC on a Luna 5 μm Phenyl-Hexyl preparative column (21×250 mm, Phenomenex) with linear gradients of 100% acetonitrile and 0.1% TFA/water buffer system (30-50% acetonitrile in 60 min). The purity of peptide is assessed using analytical RP-HPLC and pooling criteria is >95%. The main pool purity of compound 1 is found to be 98.0%. Subsequent lyophilization of the final main product pool yielded the lyophilized peptide TFA salt. The molecular weight is determined by LC-MS (obsd: M+3=1657.2; Calc M+3=1657.0).

Peptides 2 Through Peptide 265

The compounds according to Peptide 2 (SEQ ID NO:11) through Peptide 265 (SEQ ID NO:145), shown in Table 1 below, are prepared substantially as described by the procedures of Peptide 1.

Binding Assays

Glucagon (referred to as Gcg) is a Reference Standard prepared at Eli Lilly and Company. GLP-1, 7-36-NH$_2$ (referred to as GLP-1) is obtained from CPC Scientific (Sunnyvale, CA, 97.2% purity, 100 μM aliquots in 100% DMSO). GIP 1-42 (referred to as GIP) is prepared at Lilly Research Laboratories using peptide synthesis and HPLC chromatography as described above (>80% purity, 100 μM aliquots in 100% DMSO). [$^{125}$I]-radiolabeled Gcg, GLP-1, or GIP is prepared using [125]-lactoperoxidase and obtained from Perkin Elmer (Boston, MA).

Stably transfected cell lines are prepared by subcloning receptor cDNA into a pcDNA3 expression plasmid and transfected into human embryonic kidney (HEK) 293 (hGcgR and hGLP-1R) or Chinese Hamster Ovary (CHO) (hGIPR) cells followed by selection with Geneticin (hGLP-1R and hGIPR) or hygromycin B (hGcgR).

Two methods are used for the preparation of crude cell membranes.

Method 1: Frozen cell pellets are lysed on ice in hypotonic buffer containing 50 mM Tris HCl, pH 7.5, and Roche Complete™ Protease Inhibitors with EDTA. The cell suspension is disrupted using a glass Potter-Elvehjem homogenizer fitted with a Teflon® pestle for 25 strokes. The homogenate is centrifuged at 4° C. at 1100×g for 10 minutes. The supernatant is collected and stored on ice while the pellets are resuspended in homogenization buffer and rehomogenized as described above. The homogenate is centrifuged at 1100×g for 10 minutes. The second supernatant is combined with the first supernatant and centrifuged at 35000×g for 1 hour at 4° C. The resulting membrane pellet is resuspended in homogenization buffer containing protease inhibitors at approximately 1 to 3 mg/mL, quick frozen in liquid nitrogen and stored as aliquots in a −80° C. freezer until use.

Method 2: Frozen cell pellets are lysed on ice in hypotonic buffer containing 50 mM Tris HCl, pH 7.5, 1 mM MgCl$_2$, Roche Complete™ EDTA-free Protease Inhibitors and 25 units/ml DNAse I (Invitrogen). The cell suspension is disrupted using a glass Potter-Elvehjem homogenizer fitted with a Teflon® pestle for 20 to 25 strokes. The homogenate is centrifuged at 4° C. at 1800×g for 15 minutes. The supernatant is collected and stored on ice while the pellets are resuspended in homogenization buffer (without DNAse I) and rehomogenized as described above. The homogenate is centrifuged at 1800×g for 15 minutes. The second supernatant is combined with the first supernatant and centrifuged an additional time at 1800×g for 15 minutes. The overall supernatant is then centrifuged at 25000×g for 30 minutes at 4° C. The resulting membrane pellet is resuspended in homogenization buffer (without DNAse I) containing protease inhibitors at approximately 1 to 3 mg/mL and stored as aliquots in a −80° C. freezer until use.

Binding Determination Methods

The equilibrium binding dissociation constants ($K_d$) for the various receptor/radioligand interactions are determined from homologous competition binding analysis instead of saturation binding due to high propanol content in the [$^{125}$I] stock material. The $K_d$ values determined for the receptor preparations were as follows: hGcgR (3.9 nM), hGLP-1R (1.2 nM) and hGIPR (0.14 nM).

[$^{125}$I]-Glucagon Binding

The human Geg receptor binding assays are performed using a Scintillation Proximity Assay (SPA) format with wheat germ agglutinin (WGA) beads (Perkin Elmer). The binding buffer contains 25 mM 4-(2-hydroxyethyl)-1-piperazineethanesulfonic acid (HEPES), pH 7.4, 2.5 mM CaCl$_2$), 1 mM MgCl$_2$, 0.1% (w/v) bacitracin (Research Products), 0.003% (w/v) Polyoxyethylenesorbitan monolaurate (TWEEN®-20), and Roche Complete™ Protease Inhibitors without EDTA. Peptides and Geg are thawed and 3-fold serially diluted in 100% DMSO (10 point concentration response curves). Next, 5 μL serially diluted compound or DMSO is transferred into Corning® 3632 clear bottom assay plates containing 45 μL assay binding buffer or unlabeled Gcg control (non-specific binding or NSB, at 1 µM final). Then, 50 µL [$^{125}$I]-Gcg (0.15 nM final), 50 µL human GcgR membranes (1.5 µg/well) and 50 µL of WGA SPA beads (80 to 150 µg/well) are added with a Biotek Multiflo dispenser. Plates are sealed and mixed on a plate shaker (setting 6) for 1 minute and read with a PerkinElmer Trilux MicroBeta® scintillation counter after 12 hours of incubation/settling time at room temperature. Final assay concentration ranges for peptides tested in response curves is typically 1150 nM to 0.058 nM and for the control Gcg from 1000 nM to 0.05 nM.

[$^{125}$I]-GLP-1 Binding

The human GLP-1 receptor binding assay is performed using an SPA format with WGA beads. The binding buffer contains 25 mM HEPES, pH 7.4, 2.5 mM CaCl$_2$, 1 mM MgCl$_2$, 0.1% (w/v) bacitracin, 0.003% (w/v) TWEEN®-20, and Roche Complete™ Protease Inhibitors without EDTA. Peptides and GLP-1 are thawed and 3-fold serially diluted in 100% DMSO (10 point concentration response curves). Next, 5 µL serially diluted compound or DMSO is transferred into Corning® 3632 clear bottom assay plates containing 45 µL assay binding buffer or unlabeled GLP-1 control (non-specific binding or NSB, at 0.25 µM final). Then, 50 µL [$^{125}$I]-GLP-1 (0.15 nM final), 50 µL human GLP-1R membranes (0.5 µg/well and 50 µL of WGA SPA beads (100 to 150 µg/well) are added with a Biotek Multiflo dispenser. Plates are sealed and mixed on a plate shaker (setting 6) for 1 minute and read with a PerkinElmer Trilux MicroBeta® scintillation counter after 5 to 12 hours of incubation/settling time at room temperature. Final assay concentration ranges for peptides tested in response curves are typically 1150 nM to 0.058 nM and for the control GLP-1, 250 nM to 0.013 nM.

[125I]-GIP Binding

The human GIP receptor binding assay is performed using an SPA format with WGA beads. The binding buffer contains 25 mM HEPES, pH 7.4, 2.5 mM CaCl$_2$, 1 mM MgCl$_2$, 0.1% (w/v) bacitracin, 0.003% (w/v) TWEEN®-20, and Roche Complete™ Protease Inhibitors without EDTA. Peptides and GIP are thawed and 3 fold serially diluted in 100% DMSO (10 point concentration response curves). Next, 5 µL serially diluted compound or DMSO is transferred into Corning® 3632 clear bottom assay plates containing 45 µL assay binding buffer or unlabeled GIP control (non-specific binding or NSB, at 0.25 µM final). Then, 50 µL [$^{125}$I]-GIP (0.075-0.15 nM final), 50 µL human GIPR membranes (3 µg/well) and 50 µL of WGA SPA beads (100 to 150 µg/well) are added with a Biotek Multiflo dispenser. Plates are sealed and mixed on a plate shaker (setting 6) for 1 minute and read with a PerkinElmer Trilux MicroBeta® scintillation counter after 2.5 to 12 hours of incubation/settling time at room temperature. Final assay concentration ranges for peptides tested in response curves is typically 1150 to 0.058 nM or 115 nM to 0.0058 nM and for the control GIP, 250 nM to 0.013 nM.

Binding Assay Data Normalization

Raw CPM data for concentration curves of peptides, Gcg, GLP-1, or GIP are converted to percent inhibition by subtracting nonspecific binding (binding in the presence of excess unlabeled Gcg, GLP-1, or GIP, respectively) from the individual CPM values and dividing by the total binding signal, also corrected by subtracting nonspecific binding. Data are analyzed using four-parameter (curve maximum, curve minimum, IC$_{50}$, Hill slope) nonlinear regression routines (Genedata Screener, version 12.0.4, Genedata AG, Basal, Switzerland). The affinity constant (K$_i$) is calculated from the absolute IC$_{50}$ value based upon the equation K$_i$=IC$_{50}$/(1+D/K$_d$) where D=the concentration of radioligand used in the experiment, IC$_{50}$ is the concentration causing 50% inhibition of binding and K$_d$ is the equilibrium binding dissociation constant of the radioligand (described above). Values for K$_i$ are reported as the geometric mean, with error expressed as the standard error of the mean (SEM) and n is equal to the number of independent replicates (determined in assays performed on different days). Geometric Means are calculated as follows:

$$\text{Geometric Mean} = 10^{(\text{Arithmetic Mean of Log } K_i \text{ Values})}$$

The Ki Ratio (Ki for native control peptide/Ki for test compound) at each receptor and each species is calculated. The Ki Ratio is a rapid indication of the apparent affinity of a peptide compared to the native control peptide. A Ki Ratio<1 indicates that the test peptide has a lower affinity (higher Ki value) for the receptor than the native peptide, whereas a Ki Ratio>1 indicates that the test peptide has a higher affinity (lower Ki value) for the receptor than the native peptide.

EXAMPLE 1

CAMP Pharmacological Functional Assay in Presence of Casein

An additional set of cAMP assays are conducted in HEK293 cells expressing the human GLP-1 receptor (GLP-1R), gastric inhibitory peptide receptor (GIPR), Glucagon receptor (GcgR). Pharmacological activity of the hGLP1R/GIPR peptides are determined in HEK293 cells stably expressing the human GLP-1 receptor (GLP-1R), gastric inhibitory peptide receptor (GIPR), or GLP-2 receptor (GLP-2R). Each receptor over-expressing cell line (20 µl) is treated with the test peptide in DMEM (Gibco Cat #31053) supplemented with 0.1% Casein (Sigma Cat #C4765), 250 µM IBMX, 1× GlutaMAX™ (Gibco Cat #35050), and 20 mM HEPES (HyClone Cat #SH30237.01) in a 20 µl assay volume. After 60 minute incubation at room temperature, the resulting increase in intracellular CAMP is quantitatively determined using the CisBio CAMP Dynamic 2 HTRF Assay Kit (62AM4PEJ). The Lysis buffer containing cAMP-d2 conjugate (20 µl) and the antibody anti-cAMP-Eu3+-Cryptate (20 µl) are then added to determine the CAMP level. After 1 hour-incubation at room temperature, HTRF signal is detected with an Envision 2104 plate reader (PerkinElmer). Each of the two incubation steps (60 minutes and 1 hour) may be conducted at about room temperature or about 37 C, so long as both the 60 minute and 1 hour incubations are completed at about the same temperature for each run of the assay. Fluorescent emission at 620 nm and at 665 nm is measured and the ratio between 620 nm and at 665 nm is calculated and then are converted to nM CAMP per well using a cAMP standard curve. Dose response curves of compounds are plotted as the percentage of stimulation normalized to minimum (buffer only) and maximum (maximum concentration of each control ligand) values and analyzed using a four parameter non-liner regression fit with a variable slope (Genedata Screener 13). EC50 is the concentration of compound causing half-maximal simulation in a dose response curve. A relative EC$_{50}$ value is derived by non-linear regression analysis using the percent maximal response vs. the concentration of peptide added, fitted to a four-parameter logistic equation.

Using Homogeneous Time Resolved Fluorescence methods, assays are conducted to determine the intrinsic potency of Example and comparator molecules performed in the presence of casein (instead of serum albumin) as a nonspecific blocker, which does not interact with the fatty acid moieties of the analyzed molecules.

Intracellular cAMP levels are determined by extrapolation using a standard curve. Dose response curves of compounds are plotted as the percentage of stimulation normalized to minimum (buffer only) and maximum (maximum concentration of each control ligand) values and analyzed using a four parameter non-linear regression fit with a variable slope (Genedata Screener 13). $EC_{50}$ is the concentration of compound causing half-maximal simulation in a dose response curve. Each relative EC50 value for the Geometric mean calculation is determined from a curve fitting.

Concentration response curves of compounds are plotted as the percentage of stimulation normalized to minimum (buffer only) and maximum (maximum concentration of each control ligand) values and analyzed using a four parameter non-liner regression fit with a variable slope (Genedata Screener 13). EC50 is the concentration of compound causing half-maximal simulation in a dose response curve. The $EC_{50}$ summary statistics are computed as follows:

Geometric Mean:

GM=10^(arithmetic mean of $\log_{10}$ transformed EC50 values).

The standard error of the mean is reported:

SEM=geometric mean×(standard deviation of $\log_{10}$ transformed EC50 values/square root of the # of runs)×$\log_e$ of 10.

The log transform accounts for the $EC_{50}$ values falling on a multiplicative, rather than an arithmetic scale.

Each day the assay is run, the test peptides are run plus the native ligands GIP and GLP-1 and buffer only as baseline (minimum), and the highest concentration of the respective GIP and GLP-1 standard that day is used as a maximum for the calculation.

TABLE 1

Functional activation of hGLP-1R and hGIPR in the presence of 0.1% Casein.

| Peptide Number | Compound Name | SEQ ID NO | hGIPR cAMP $EC_{50}$ ratio | hGLP1R cAMP $EC_{50}$ ratio | [hGIPR/ hGLP1R] $EC_{50}$ Ratio |
|---|---|---|---|---|---|
| 1 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 10 | 4.65 | 1.12 | 4.15 |
| 2 | Y-Aib-EGT-αMeF(2F)-TSDYSI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 11 | 5.89 | 0.888 | 6.63 |
| 3 | Y-Aib-EGT-αMeF(2F)-TSDYSI-αMeL-LD-Orn-K((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 12 | 4.51 | 1.25 | 3.61 |
| 4 | Y-Aib-EGT-αMeF(2F)-TSD-4Pal-SI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-αMeY-LIEGGPSSGAPPPS-NH$_2$ | 13 | 5.95 | 1.41 | 4.22 |
| 8 | Y-Aib-EGTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 14 | 1.97 | 0.419 | 4.70 |
| 9 | Y-Aib-EGTFTSDYSILLDSK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 15 | 0.768 | 0.314 | 2.45 |
| 20 | Y-Aib-EGTFTSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 16 | 2.81 | 0.577 | 4.87 |
| 21 | Y-Aib-EGTFTSDYSI-αMeL-LDEK((2-[2-(2-Amino-ethoxy)-ethoxy]-acetyl)$_2$-(γGlu)-CO—(CH$_2$)$_{18}$—CO$_2$H)AQ-αMeK-AFIEYLLEGGPSSGAPPPS-NH$_2$ | 17 | 1.95 | 0.402 | 4.85 |
| 22 | Y-Aib-EGTFTSDYSI-αMeL-LDEK((2-[2-(2-Amino-ethoxy)-ethoxy]-acetyl)$_2$-(γGlu)-CO—(CH$_2$)$_{18}$—CO$_2$H)AQ-αMeK-AFIEYLLE-Aib-GPSSGAPPPS-NH$_2$ | 18 | 1.86 | 0.29 | 6.41 |
| 25 | Y-Aib-EGTFTSDYSK((2-[2-(2-Amino-ethoxy)-ethoxy]-acetyl)$_2$-(γGlu)-CO—(CH$_2$)$_{18}$—CO$_2$H)LLDKIAQ-Aib-AFIEYLIEGGPSSGAPPPS-NH$_2$ | 19 | 0.636 | 0.197 | 3.23 |
| 26 | Y-Aib-EGTFTSDYSIK((2-[2-(2-Amino-ethoxy)-ethoxy]-acetyl)$_2$-(γGlu)-CO—(CH$_2$)$_{18}$—CO$_2$H)LDKIAQ-Aib-AFIEYLIEGGPSSGAPPPS-NH$_2$ | 20 | 0.585 | 0.238 | 2.46 |

TABLE 1-continued

Functional activation of hGLP-1R and hGIPR in the presence of 0.1% Casein.

| Peptide Number | Compound Name | SEQ ID NO | hGIPR CAMP $EC_{50}$ ratio | hGLP1R CAMP $EC_{50}$ ratio | [hGIPR/ hGLP1R] $EC_{50}$ Ratio |
|---|---|---|---|---|---|
| 29 | Y-Aib-EGTFTSDYSILLDK((2-[2-(2-Amino-ethoxy)-ethoxy]-acetyl)$_2$-(γGlu)-CO—(CH$_2$)$_{18}$—CO$_2$H)IAQ-Aib-AFIEYLIEGGPSSGAPPPS-NH$_2$ | 21 | 0.536 | 0.0671 | 7.99 |
| 31 | Y-Aib-EGTFTSDYSILLDKIAK((2-[2-(2-Amino-ethoxy)-ethoxy]-acetyl)$_2$-(γGlu)-CO—(CH$_2$)$_{18}$—CO$_2$H)-Aib-AFIEYLIEGGPSSGAPPPS-NH$_2$ | 22 | 0.456 | 0.0708 | 6.44 |
| 32 | Y-Aib-EGTFTSDYSILLDKIAQ-Aib-K((2-[2-(2-Amino-ethoxy)-ethoxy]-acetyl)$_2$-(γGlu)-CO—(CH$_2$)$_{18}$—CO$_2$H)FIEYLIEGGPSSGAPPPS-NH$_2$ | 23 | 0.84 | 0.136 | 6.18 |
| 33 | Y-Aib-EGTFTSDYSILLDKIAQ-Aib-AFK((2-[2-(2-Amino-ethoxy)-ethoxy]-acetyl)$_2$-(γGlu)-CO—(CH$_2$)$_{18}$—CO$_2$H)EYLIEGGPSSGAPPPS-NH$_2$ | 24 | 0.00222 | 0.000256 | 8.67 |
| 34 | Y-Aib-EGTFTSDYSILLDKIAQ-Aib-AFIK((2-[2-(2-Amino-ethoxy)-ethoxy]-acetyl)$_2$-(γGlu)-CO—(CH$_2$)$_{18}$—CO$_2$H)YLIEGGPSSGAPPPS-NH$_2$ | 25 | 0.393 | 0.0392 | 10.03 |
| 37 | Y-Aib-EGTFTSDYSILLDKIAQ-Aib-AFIEYLIK((2-[2-(2-Amino-ethoxy)-ethoxy]-acetyl)$_2$-(γGlu)-CO—(CH$_2$)$_{18}$—CO$_2$H)GGPSSGAPPPS-NH$_2$ | 26 | 0.532 | 0.0533 | 9.98 |
| 41 | Y-Aib-EGTFTSDYSILLDKIAQ-Aib-AFIEYLIEGGPK((2-[2-(2-Amino-ethoxy)-ethoxy]-acetyl)$_2$-(γGlu)-CO—(CH$_2$)$_{18}$—CO$_2$H)SGAPPPS-NH$_2$ | 27 | 0.637 | 0.0637 | 10.00 |
| 46 | Y-Aib-EGTFTSDYSILLDKIAQ-Aib-AFIEYLIEGGPSSGAPK((2-[2-(2-Amino-ethoxy)-ethoxy]-acetyl)$_2$-(γGlu)-CO—(CH$_2$)$_{18}$—CO$_2$H)PS-NH$_2$ | 28 | 0.828 | 0.0969 | 8.54 |
| 47 | Y-Aib-EGTFTSDYSILLDKIAQ-Aib-AFIEYLIEGGPSSGAPPK((2-[2-(2-Amino-ethoxy)-ethoxy]-acetyl)$_2$-(γGlu)-CO—(CH$_2$)$_{18}$—CO$_2$H)S-NH$_2$ | 29 | 0.654 | 0.089 | 7.35 |
| 48 | Y-Aib-EGTFTSDYSILLDKIAQ-Aib-AFIEYLIEGGPSSGAPPPK((2-[2-(2-Amino-ethoxy)-ethoxy]-acetyl)$_2$-(γGlu)-CO—(CH$_2$)$_{18}$—CO$_2$H)—NH$_2$ | 30 | 0.863 | 0.0966 | 8.93 |
| 50 | Y-Aib-EGTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSG-NH$_2$ | 31 | 1.96 | 0.675 | 2.90 |
| 51 | Y-Aib-EGTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGG-NH$_2$ | 32 | 1.69 | 0.426 | 3.97 |
| 52 | Y-Aib-EGTFTSDYSI-αMeL-LDSK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 33 | 1.4 | 0.514 | 2.72 |
| 60 | Y-Aib-EGTFTSDYSI-αMeL-LD-Aib-K((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 34 | 1.06 | 0.237 | 4.47 |
| 62 | Y-Aib-EGTFTSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGG-NH$_2$ | 35 | 2.33 | 0.463 | 5.03 |
| 63 | Y-Aib-EGTFTSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-AFIEYLIEGG-NH$_2$ | 36 | 1.58 | 0.386 | 4.09 |
| 64 | Y-Aib-EGTFTSDYSI-αMeL-LDSK((2-[2-(2-Amino-ethoxy)-ethoxy]-acetyl)$_2$-(γGlu)-CO—(CH$_2$)$_{18}$—CO$_2$H)AQ-Aib-AFIEYLIEGG-NH$_2$ | 37 | 1.57 | 0.429 | 3.66 |
| 65 | Y-Aib-EGTFTSDYSI-αMeL-LDTK((2-[2-(2-Amino-ethoxy)-ethoxy]-acetyl)$_2$-(γGlu)-CO—(CH$_2$)$_{18}$—CO$_2$H)AQ-Aib-AFIEYLIEGG-NH$_2$ | 38 | 1.04 | 0.233 | 4.46 |

TABLE 1-continued

Functional activation of hGLP-1R and hGIPR in the presence of 0.1% Casein.

| Peptide Number | Compound Name | SEQ ID NO | hGIPR CAMP $EC_{50}$ ratio | hGLP1R CAMP $EC_{50}$ ratio | [hGIPR/ hGLP1R] $EC_{50}$ Ratio |
|---|---|---|---|---|---|
| 66 | Y-Aib-EGTFTSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-AFIEYLLEGGPSSGAPPPS-NH$_2$ | 39 | 1.89 | 0.255 | 7.41 |
| 68 | Y-Aib-EGTFTSDY-aMeS-ILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 40 | 1.67 | 0.354 | 4.72 |
| 69 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 41 | 2.73 | 0.85 | 3.21 |
| 73 | Y-Aib-EGTFTSDYSILLDKIAQ-Aib-AFIEYLIK((2-[2-(2-Amino-ethoxy)-ethoxy]-acetyl)$_2$-(γGlu)-CO—(CH$_2$)$_{18}$—CO$_2$H)GG-NH$_2$ | 42 | 0.174 | 0.0225 | 7.73 |
| 80 | Y-(D-Ala)-EGTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 43 | 1.09 | 0.227 | 4.80 |
| 81 | Y-Aib-EGTFTSDY-(D-Ser)-ILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 44 | 0.373 | 0.063 | 5.92 |
| 83 | Y-Aib-EGTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLI-(D-Glu)-GGPSSGAPPPS-NH$_2$ | 45 | 0.804 | 0.166 | 4.84 |
| 84 | Y-Aib-EGTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFI-(D-Glu)-YLIEGGPSSGAPPPS-NH$_2$ | 46 | 1.59 | 0.173 | 9.19 |
| 88 | Y-Pro-EGTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 47 | 0.392 | 0.0918 | 4.27 |
| 89 | Y-Aib-Aad-GTFTSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 48 | 1.57 | 0.175 | 8.97 |
| 95 | Y-Aib-EGT-αMeF-TSDYSILLDKIAQ-Aib-AFIEYLIK((2-[2-(2-Amino-ethoxy)-ethoxy]-acetyl)$_2$-(γGlu)-CO—(CH$_2$)$_{18}$—CO$_2$H)GG-NH$_2$ | 49 | 0.145 | 0.0576 | 2.52 |
| 97 | Y-Aib-EGTFTSDYSI-αMeL-LDKIAQ-Aib-AFIEYLIK((2-[2-(2-Amino-ethoxy)-ethoxy]-acetyl)$_2$-(γGlu)-CO—(CH$_2$)$_{18}$—CO$_2$H)GG-NH$_2$ | 50 | 0.0953 | 0.0268 | 3.56 |
| 98 | Y-Aib-EGT-αMeF-TSDYSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSG-NH$_2$ | 51 | 2.43 | 0.384 | 6.33 |
| 99 | Y-Aib-EGT-αMeF-TSDYSI-αMeL-LDSK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSG-NH$_2$ | 52 | 2.27 | 0.629 | 3.61 |
| 103 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIEYLIEGG-NH$_2$ | 53 | 2.01 | 0.655 | 3.07 |
| 104 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-EFIEYLIEGG-NH$_2$ | 54 | 4.93 | 1.85 | 2.66 |
| 108 | Y-Aib-EGTFTSDYSILLDKK((2-[2-(2-Amino-ethoxy)-ethoxy]-acetyl)-AOC-(γGlu)-CO—(CH$_2$)$_{18}$—CO$_2$H)AQ-Aib-AFIEYLIEGGPSSGAPPPS-NH$_2$ | 55 | 2.19 | 0.218 | 10.05 |
| 109 | Y-Aib-EGTFTSDYSILLDKK(AOC-(2-[2-(2-Amino-ethoxy)-ethoxy]-acetyl)-(γGlu)-CO—(CH$_2$)$_{18}$—CO$_2$H)AQ-Aib-AFIEYLIEGGPSSGAPPPS-NH$_2$ | 56 | 1.83 | 0.182 | 10.05 |

TABLE 1-continued

Functional activation of hGLP-1R and hGIPR in the presence of 0.1% Casein.

| Peptide Number | Compound Name | SEQ ID NO | hGIPR CAMP EC$_{50}$ ratio | hGLP1R CAMP EC$_{50}$ ratio | [hGIPR/hGLP1R] EC$_{50}$ Ratio |
|---|---|---|---|---|---|
| 110 | Y-Aib-EGTFTSDYSILLDKK((2-[2-(2-Amino-ethoxy)-ethoxy]-acetyl)-(γGlu)-(Trx)-CO—(CH$_2$)$_{18}$—CO$_2$H)AQ-Aib-AFIEYLIEGGPSSGAPPPS-NH$_2$ | 57 | 0.929 | 0.358 | 2.59 |
| 111 | Y-Aib-EGTFTSDYSILLDKK((2-[2-(2-Amino-ethoxy)-ethoxy]-acetyl)-(Trx)-(γGlu)-CO—(CH$_2$)$_{18}$—CO$_2$H)AQ-Aib-AFIEYLIEGGPSSGAPPPS-NH$_2$ | 58 | 1.1 | 0.209 | 5.26 |
| 112 | Y-Aib-EGTFTSDYSILLDKK((2-[2-(2-Amino-ethoxy)-ethoxy]-acetyl)-(εK)-(γGlu)-CO—(CH$_2$)$_{18}$—CO$_2$H)AQ-Aib-AFIEYLIEGGPSSGAPPPS-NH$_2$ | 59 | 1.53 | 0.402 | 3.81 |
| 113 | Y-Aib-EGTFTSDYSILLDKK((2-[2-(2-Amino-ethoxy)-ethoxy]-acetyl)$_2$-(εK)-CO—(CH$_2$)$_{18}$—CO$_2$H)AQ-Aib-AFIEYLIEGGPSSGAPPPS-NH$_2$ | 60 | 1.39 | 0.275 | 5.05 |
| 114 | Y-Aib-EGTFTSDYSILLDKK((2-[2-(2-Amino-ethoxy)-ethoxy]-acetyl)-(εK)-(EK)-CO—(CH$_2$)$_{18}$—CO$_2$H)AQ-Aib-AFIEYLIEGGPSSGAPPPS-NH$_2$ | 61 | 1.65 | 0.234 | 7.05 |
| 115 | Y-Aib-EGT-αMeF-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 62 | 1.85 | 0.743 | 2.49 |
| 118 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIEYLIEGGPSSGAPPPS-NH$_2$ | 63 | 3.42 | 1.13 | 3.03 |
| 120 | Y-Aib-cTA-GT-αMeF-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 64 | 1.67 | 0.319 | 5.24 |
| 123 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-EFIEYLIEGGPSSG-NH$_2$ | 65 | 4.04 | 1.58 | 2.56 |
| 125 | Y-Aib-EGT-αMeF-TSDYSI-αMeL-LDKK((2-[2-(2-Amino-ethoxy)-ethoxy]-acetyl)$_2$-(γGlu)$_2$-CO—(CH$_2$)$_{18}$—CO$_2$H)AQ-Aib-AFIEYLIEGGPSSGAPPPS-NH$_2$ | 66 | 3.79 | 1.31 | 2.89 |
| 126 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-AFIEYLIEAGPSSGAPPPS-NH$_2$ | 67 | 2.53 | 0.869 | 2.91 |
| 128 | Y-Aib-EGT-αMeF-TSDHSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 68 | 2.46 | 0.7 | 3.51 |
| 129 | Y-Aib-EGT-αMeF-TSDLSILLDKK((2-[2-(2-Amino-ethoxy)-ethoxy]-acetyl)$_2$-(γGlu)-CO—(CH$_2$)$_{18}$—CO$_2$H)AQ-Aib-AFIEYLIEGGPSSGAPPPS-NH$_2$ | 69 | 1.88 | 0.543 | 3.46 |
| 137 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-Aad-FIEYLIEGGPSSGAPPPS-NH$_2$ | 70 | 4.47 | 1.25 | 3.58 |
| 139 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-TFIEYLIEGGPSSGAPPPS-NH$_2$ | 71 | 3.61 | 1.13 | 3.19 |
| 140 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-DFIEYLIEGGPSSGAPPPS-NH$_2$ | 72 | 3.76 | 1.16 | 3.24 |
| 143 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-Aib-FIEYLIEGGPSSGAPPPS-NH$_2$ | 73 | 2.78 | 0.714 | 3.89 |
| 144 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQH-Aib-FIEYLIEGGPSSGAPPPS-NH$_2$ | 74 | 3.6 | 0.851 | 4.23 |

TABLE 1-continued

Functional activation of hGLP-1R and hGIPR in the presence of 0.1% Casein.

| Peptide Number | Compound Name | SEQ ID NO | hGIPR CAMP $EC_{50}$ ratio | hGLP1R CAMP $EC_{50}$ ratio | [hGIPR/hGLP1R] $EC_{50}$ Ratio |
|---|---|---|---|---|---|
| 147 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-Aad-YLIEGGPSSGAPPPS-NH$_2$ | 75 | 4.14 | 1.13 | 3.66 |
| 148 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIAYLIEGGPSSGAPPPS-NH$_2$ | 76 | 2.7 | 0.859 | 3.14 |
| 149 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIVYLIEGGPSSGAPPPS-NH$_2$ | 77 | 1.82 | 0.484 | 3.76 |
| 150 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFISYLIEGGPSSGAPPPS-NH$_2$ | 78 | 2.64 | 0.79 | 3.34 |
| 151 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIPYLIEGGPSSGAPPPS-NH$_2$ | 79 | 0.262 | 0.0278 | 9.42 |
| 152 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-Aib-YLIEGGPSSGAPPPS-NH$_2$ | 80 | 2.57 | 0.484 | 5.31 |
| 153 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIHYLIEGGPSSGAPPPS-NH$_2$ | 81 | 1.7 | 0.501 | 3.39 |
| 154 | Y-Aib-EGT-αMeF(2F)-TSDHSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIEYLIEGGPSSGAPPPS-NH$_2$ | 82 | 5.9 | 1.23 | 4.80 |
| 155 | Y-Aib-EGT-αMeF(2F)-TSD-cTA-SI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIEYLIEGGPSSGAPPPS-NH$_2$ | 83 | 0.584 | 0.0978 | 5.97 |
| 157 | Y-Aib-EGT-αMeF(2F)-TSD-3Pal-SI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIEYLIEGGPSSGAPPPS-NH$_2$ | 84 | 3.15 | 1.25 | 2.52 |
| 167 | Y-Aib-EGT-αMeF(2F)-TSDHSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-TFI-(D-Glu)-YLIEGGPSSG-NH$_2$ | 85 | 0.291 | 0.0487 | 5.98 |
| 168 | Y-Aib-EGT-αMeF(2F)-TSDHSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-TFI-(D-Glu)-YLIEGGPSSGAPPPS-NH$_2$ | 86 | 0.313 | 0.0323 | 9.69 |
| 169 | Y-Aib-EGT-αMeF(2F)-TSDHSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-TFI-(D-Glu)-YLIEGGPSSGAPPPS-NH$_2$ | 87 | 0.122 | 0.0136 | 8.97 |
| 171 | Y-Aib-EGT-αMeF(2F)-TSDHSI-αMeL-LD-Orn-K((2-[2-(2-Amino-ethoxy)-ethoxy]-acetyl)$_2$-(γGlu)-CO—(CH$_2$)$_{18}$—CO$_2$H)AQ-Aib-TFI-(D-Glu)-YLIEGGPSSGAPPPS-NH$_2$ | 88 | 0.471 | 0.0609 | 7.73 |
| 172 | Y-Aib-EGT-αMeF(2F)-TSDHSI-αMeL-LD-Dab-K((2-[2-(2-Amino-ethoxy)-ethoxy]-acetyl)$_2$-(γGlu)-CO—(CH$_2$)$_{18}$—CO$_2$H)AQ-Aib-TFI-(D-Glu)-YLIEGGPSSGAPPPS-NH$_2$ | 89 | 0.1 | 0.038 | 2.63 |
| 173 | Y-Aib-EGT-αMeF(2F)-TSDHSI-αMeL-LD-Dap-K((2-[2-(2-Amino-ethoxy)-ethoxy]-acetyl)$_2$-(γGlu)-CO—(CH$_2$)$_{18}$—CO$_2$H)AQ-Aib-TFI-(D-Glu)-YLIEGGPSSGAPPPS-NH$_2$ | 90 | 0.179 | 0.0373 | 4.80 |

TABLE 1-continued

Functional activation of hGLP-1R and hGIPR in the presence of 0.1% Casein.

| Peptide Number | Compound Name | SEQ ID NO | hGIPR CAMP $EC_{50}$ ratio | hGLP1R CAMP $EC_{50}$ ratio | [hGIPR/ hGLP1R] $EC_{50}$ Ratio |
|---|---|---|---|---|---|
| 174 | Y-Aib-EGT-αMeF(2F)-TSDHSI-αMeL-LDEK((2-[2-(2-Amino-ethoxy)-ethoxy]-acetyl)$_2$-CO—(CH$_2$)$_{18}$—CO$_2$H)AQ-Aib-TFI-(D-Glu)-YLIEGGPSSGAPPPS-NH$_2$ | 91 | 0.483 | 0.0968 | 4.99 |
| 176 | Y-Aib-EGT-αMeF(2F)-TSDHSI-αMeL-LDEK((2-[2-(2-Amino-ethoxy)-ethoxy]-acetyl)$_2$-(εK)-CO—(CH$_2$)$_{16}$—CO$_2$H)AQ-Aib-TFI-(D-Glu)-YLIEGGPSSGAPPPS-NH$_2$ | 92 | 0.201 | 0.0427 | 4.71 |
| 178 | Y-Aib-EGT-αMeF(2F)-TSDHSI-αMeL-LDEK((2-[2-(2-Amino-ethoxy)-ethoxy]-acetyl)$_2$-(γGlu)-CO—(CH$_2$)$_{14}$—CO$_2$H)AQ-Aib-HFI-(D-Glu)-YLIEGGPSSGAPPPS-NH$_2$ | 93 | 0.0341 | 0.00349 | 9.77 |
| 179 | Y-Aib-EGT-αMeF(2F)-TSDHSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-HFI-(D-Glu)-YLIEGGPSSG-NH$_2$ | 94 | 0.0575 | 0.0169 | 3.40 |
| 180 | Y-Aib-EGT-αMeF(2F)-TSDHSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-HFI-(D-Glu)-YLIEGG-NH$_2$ | 95 | 0.133 | 0.0212 | 6.27 |
| 181 | Y-Aib-EGT-αMeF(2F)-TSD-3Pal-SI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 96 | 4.1 | 0.718 | 5.71 |
| 182 | Y-Aib-EGT-αMeF(2F)-TSD-4Pal-SI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 97 | 4.37 | 0.873 | 5.01 |
| 183 | Y-Aib-EGT-αMeF(2F)-TSDLSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 98 | 3.1 | 0.843 | 3.68 |
| 187 | Y-Aib-EGT-αMeF(2F)-TSDQSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 99 | 4.61 | 0.702 | 6.57 |
| 189 | Y-Aib-EGT-αMeF(2F)-TSD-4Pal-SI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-Aib-YLIEGGPSSGAPPPS-NH$_2$ | 100 | 2.41 | 0.668 | 3.61 |
| 197 | Y-αMePro-EGTFTSDYSILLDEK((2-[2-(2-Amino-ethoxy)-ethoxy]-acetyl)$_2$-(γGlu)-CO—(CH$_2$)$_{16}$—CO$_2$H) AQQAFIEYLIEGGPSSG-NH$_2$ | 101 | 0.855 | 0.189 | 4.52 |
| 202 | Y-Aib-EGT-αMeF(2F)-TSD-4Pal-SI-αMeL-LDKK((2-[2-(2-Amino-ethoxy)-ethoxy]-acetyl)-(γGlu)-(2-[2-(2-Amino-ethoxy)-ethoxy]-acetyl)-CO—(CH$_2$)$_{18}$—CO$_2$H)AQ-Aib-EFI-(D-Glu)-YLIEGGPSSGAPPPS-NH$_2$ | 102 | 4.79 | 0.712 | 6.73 |
| 203 | Y-Aib-EGT-αMeF(2F)-TSD-4Pal-SI-αMeL-LDKK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 103 | 4.95 | 0.671 | 7.38 |
| 204 | Y-Aib-EGT-αMeF(2F)-TSD-4Pal-SI-αMeL-LDEK((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 104 | 4.58 | 0.689 | 6.65 |
| 205 | Y-Aib-EGT-αMeF(2F)-TSD-4Pal-SI-αMeL-LDEK((2-[2-(2-Amino-ethoxy)-ethoxy]-acetyl)$_2$-CO—(CH$_2$)$_{16}$—CO$_2$H)AQ-Aib-EFI-(D-Glu)-YLIEGGPSSGAPPPS-NH$_2$ | 105 | 5.71 | 1.46 | 3.91 |

TABLE 1-continued

Functional activation of hGLP-1R and hGIPR in the presence of 0.1% Casein.

| Peptide Number | Compound Name | SEQ ID NO | hGIPR CAMP $EC_{50}$ ratio | hGLP1R CAMP $EC_{50}$ ratio | [hGIPR/ hGLP1R] $EC_{50}$ Ratio |
|---|---|---|---|---|---|
| 206 | Y-Aib-EGT-αMeF(2F)-TSD-4Pal-SI-αMeL-LDEK((2-[2-(2-Amino-ethoxy)-ethoxy]-acetyl)$_2$CO—(CH$_2$)$_{18}$—CO$_2$H)AQ-Aib-EFI-(D-Glu)-YLIEGGPSSGAPPPS-NH$_2$ | 106 | 4.75 | 1.42 | 3.35 |
| 207 | Y-Aib-EGT-αMeF(2F)-TSD-4Pal-SI-αMeL-LDEK((2-[2-(2-Amino-ethoxy)-ethoxy]-acetyl)$_2$-(εK)-CO—(CH$_2$)$_{18}$—CO$_2$H)AQ-Aib-EFI-(D-Glu)-YLIEGGPSSGAPPPS-NH$_2$ | 107 | 4.76 | 1.23 | 3.87 |
| 208 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{14}$—CO$_2$H)AQ-Aib-EFI-(D-Glu)-YLIEGGPSSGAPPPS-NH$_2$ | 108 | 5.33 | 0.587 | 9.08 |
| 209 | Y-Aib-EGT-αMeF(2F)-TSDYSI-αMeL-LD-Dab-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 109 | 5.73 | 1.12 | 5.12 |
| 210 | Y-Aib-EGT-αMeF(2F)-TSDYSI-αMeL-LD-Dap-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 110 | 5.4 | 1.03 | 5.24 |
| 211 | Y-Aib-EGT-αMeF(2F)-TSDYSI-αMeL-LDKK((2-[2-(2-Amino-ethoxy)-ethoxy]-acetyl)-(γGlu)-(2-[2-(2-Amino-ethoxy)-ethoxy]-acetyl)-CO—(CH$_2$)$_{18}$—CO$_2$H)AQ-Aib-EFI-(D-Glu)-YLIEGGPSSGAPPPS-NH$_2$ | 111 | 4.59 | 1.28 | 3.59 |
| 212 | Y-Aib-EGT-αMeF(2F)-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 112 | 4.17 | 0.771 | 5.41 |
| 213 | Y-Aib-EGT-αMeF-TSDYSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 113 | 3.87 | 0.694 | 5.58 |
| 214 | Y-Aib-EGT-αMeF(2F)-TSDYSI-αMeL-LDEK((2-[2-(2-Amino-ethoxy)-ethoxy]-acetyl)$_2$-CO—(CH$_2$)$_{16}$—CO$_2$H)AQ-Aib-EFI-(D-Glu)-YLIEGGPSSGAPPPS-NH$_2$ | 114 | 6.92 | 1.74 | 3.98 |
| 215 | Y-Aib-EGT-αMeF(2F)-TSDYSI-αMeL-LDEK((2-[2-(2-Amino-ethoxy)-ethoxy]-acetyl)$_2$-CO—(CH$_2$)$_{18}$—CO$_2$H)AQ-Aib-EFI-(D-Glu)-YLIEGGPSSGAPPPS-NH$_2$ | 115 | 3.53 | 0.813 | 4.34 |
| 216 | Y-Aib-EGT-αMeF(2F)-TSDYSI-αMeL-LDEK((2-[2-(2-Amino-ethoxy)-ethoxy]-acetyl)$_2$-(εK)-CO—(CH$_2$)$_{18}$—CO$_2$H)AQ-Aib-EFI-(D-Glu)-YLIEGGPSSGAPPPS-NH$_2$ | 116 | 4.91 | 1.31 | 3.75 |
| 217 | Y-Aib-EGT-αMeF(2F)-TSDYSI-αMeL-LD-Dab-K((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 117 | 3.41 | 1.14 | 2.99 |
| 218 | Y-Aib-EGT-αMeF(2F)-TSDYSI-αMeL-LD-Dap-K((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 118 | 4.43 | 1.02 | 4.34 |
| 219 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSG-NH$_2$ | 119 | 5.86 | 1.03 | 5.69 |

TABLE 1-continued

Functional activation of hGLP-1R and hGIPR in the presence of 0.1% Casein.

| Peptide Number | Compound Name | SEQ ID NO | hGIPR CAMP $EC_{50}$ ratio | hGLP1R CAMP $EC_{50}$ ratio | [hGIPR/ hGLP1R] $EC_{50}$ Ratio |
|---|---|---|---|---|---|
| 220 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGG-NH$_2$ | 120 | 6.3 | 1.36 | 4.63 |
| 221 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 121 | 4.5 | 0.795 | 5.66 |
| 222 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)--αMeY-LIEGGPSSGAPPPS-NH$_2$ | 122 | 5.84 | 1.55 | 3.77 |
| 223 | Y-Aib-EGT-αMeF(2F)-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFIE-αMeY-LIEGGPSSGAPPPS-NH$_2$ | 123 | 2.93 | 0.962 | 3.05 |
| 224 | Y-Aib-EGT-αMeF(2F)-TSDYSI-Aib-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 124 | 3.52 | 1.06 | 3.32 |
| 225 | Y-Aib-EGT-αMeF-TSDYSI-Aib-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 125 | 1.99 | 0.523 | 3.80 |
| 226 | Y-Aib-EGT-αMeF(2F)-TSDYSILLDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 126 | 4.27 | 1.25 | 3.42 |
| 227 | Y-Aib-EGT-αMeF-TSDYSI-αMeL-LDEK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 127 | 4.73 | 1.07 | 4.42 |
| 228 | Y-Aib-EGT-αMeF-TSDYSI-αMeL-LDKK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSG-NH$_2$ | 128 | 3.86 | 1.1 | 3.51 |
| 230 | Y-Aib-EGT-αMeF(2F)-TSDYSI-αMeL-LDHK((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 129 | 3.31 | 0.599 | 5.53 |
| 233 | Y-Aib-EGT-αMeF(2F)-TSD-4Pal-SI-αMeL-LD-Dab-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 130 | 4.95 | 0.535 | 9.25 |
| 236 | Y-Aib-EGT-αMeF(2F)-TSDYSI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-EFI (D-Glu)-αMeY-LIEGGPSSGAPPPS-NH$_2$ | 131 | 6.76 | 1.65 | 4.10 |
| 238 | Y-Aib-EGT-αMeF(2F)-TSDLSI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-αMeY-LIEGGPSSGAPPPS-NH$_2$ | 132 | 7.33 | 1.15 | 6.37 |
| 239 | Y-Aib-EGT-αMeF(2F)-TSD-4Pal-SI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-TFI-(D-Glu)-αMeY-LIEGGPSSGAPPPS-NH$_2$ | 133 | 5.27 | 0.987 | 5.34 |

TABLE 1-continued

Functional activation of hGLP-1R and hGIPR in the presence of 0.1% Casein.

| Peptide Number | Compound Name | SEQ ID NO | hGIPR CAMP EC$_{50}$ ratio | hGLP1R CAMP EC$_{50}$ ratio | [hGIPR/hGLP1R] EC$_{50}$ Ratio |
|---|---|---|---|---|---|
| 241 | Y-Aib-EGT-αMeF(2F)-TSDVSI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-TFI-(D-Glu)-αMeY-LIEGGPSSGAPPPS-NH$_2$ | 134 | 7.12 | 1.89 | 3.77 |
| 242 | Y-Aib-EGT-αMeF(2F)-TSDVSI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-AFI-(D-Glu)-αMeY-LIEGGPSSGAPPPS-NH$_2$ | 135 | 5.58 | 1.96 | 2.85 |
| 243 | Y-Aib-EGT-αMeF(2F)-TSDLSI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-TFI-(D-Glu)-αMeY-LIEGGPSSGAPPPS-NH$_2$ | 136 | 8.69 | 1.22 | 7.12 |
| 244 | Y-Aib-EGT-αMeF(2F)-TSDLSI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-AFI-(D-Glu)-αMeY-LIEGGPSSGAPPPS-NH$_2$ | 137 | 8.27 | 1.29 | 6.41 |
| 246 | Y-Aib-EGT-αMeF(2F)-TSDASI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-AFI-(D-Glu)-αMeY-LIEGGPSSGAPPPS-NH$_2$ | 138 | 6.36 | 2.56 | 2.48 |
| 247 | Y-Aib-EGT-αMeF(2F)-TSDYSI-Aib-LD-Orn-K((2-[2-(2-Amino-ethoxy)-ethoxy]-acetyl)$_2$-(Glu)-CO—(CH$_2$)$_{16}$—CO$_2$H)AQ-Aib-EFI-(D-Glu)-YLIEGGPSSGAPPPS-NH$_2$ | 139 | 2.58 | 0.614 | 4.20 |
| 248 | Y-Aib-EGT-αMeF(2F)-TSDYSILLD-Orn-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 140 | 5.08 | 0.8 | 6.35 |
| 249 | Y-Aib-EGT-αMeF(2F)-TSDYSI-Nle-LD-Orn-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-YLIEGGPSSGAPPPS-NH$_2$ | 141 | 3.84 | 0.778 | 4.94 |
| 250 | Y-Aib-EGT-αMeF(2F)-TSDYSI-Aib-LD-Orn-K((2-[2-(2-Amino-ethoxy)-ethoxy]-acetyl)$_2$-(γGlu)-CO—(CH$_2$)$_{18}$—CO$_2$H)AQ-Aib-EFI-(D-Glu)-YLIEGGPSSGAPPPS-NH$_2$ | 142 | 4.27 | 0.985 | 4.34 |
| 251 | Y-Aib-EGT-αMeF(2F)-TSD-4Pal-SI-αMeL-LD-Orn-K((2-[2-(2-Amino-ethoxy)-ethoxy]-acetyl)$_2$-(εK)-CO—(CH$_2$)$_{18}$—CO$_2$H)AQ-Aib-AFI-(D-Glu)-αMeY-LIEGGPSSGAPPPS-NH$_2$ | 143 | 5.12 | 1.37 | 3.74 |
| 264 | Y-Aib-EGT-αMeF(2F)-TSD-4Pal-SI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-αMeY-LIEGGPSSG-NH$_2$ | 144 | 8.4 | 3.19 | 2.63 |
| 265 | Y-Aib-EGT-αMeF(2F)-TSD-4Pal-SI-αMeL-LD-Orn-K((2-[2-(2-Amino-ethoxy)-ethoxy]-acetyl)$_2$-(γGlu)-CO—(CH$_2$)$_{16}$—CO$_2$H)AQ-Aib-EFI-(D-Glu)-αMeY-LIEGG-NH$_2$ | 145 | 9.77 | 3.27 | 2.99 |

As demonstrated by data in Table 1, the peptides, normalized to baseline and native peptides, stimulate cAMP from human GLP-1R and GIPR in the presence of 0.1% casein with a GIP potency ratio that is about 2.5 to about 10 times the GLP-1 receptor potency.

In an embodiment, is a GIP:GLP-1 coagonist compound wherein the peptide is a potent GIPR/GLP-1R dual agonist that is a partial agonist on the GLP-1R as shown by Cell Membrane Guanosine 5'-(gamma-thio) Triphosphate-[$^{35}$S] (GTPγS) Binding Assay, and a partial agonist on the GLP-1R as shown by the β-arrestin-2 recruitment assay. An embodiment, is a GIP:GLP-1 co-agonist compound, or pharmaceutically acceptable salt thereof, wherein the compound stimulates GLP-1R induced activation of Gα$_s$ in the GLP-1R HEK293 Cell Membrane Guanosine 5'-(gamma-thio) Triphosphate-[$^{35}$S] (GTPγS) Binding Assay. In an embodiment, is a compound showing partial agonism of 75% or less in the GLP-1R HEK293 Cell Membrane Guanosine 5'-(gamma-thio) Triphosphate-[$^{35}$S] (GTPγS) Binding Assay, and 35% or less in the GLP-CHO Cell β-Arrestin. Recruitment Assay.

In an embodiment is a method for treating diabetes comprising administering an effective amount of a compound showing partial agonism of 75% or less in the GLP-1R HEK293 Cell Membrane Guanosine 5'-(gamma-thio) Triphosphate-[$^{35}$S] (GTPγS) Binding Assay, and an effective amount of a compound that is a GIP agonist. In an embodiment, the compound showing partial agonism in the GLP-1R HEK293 Cell Membrane Guanosine 5'-(gamma-thio) Triphosphate-[$^{35}$S] (GTPγS) Binding Assay is co-administered with a compound having GIP agonist activity. In an embodiment, the compound showing partial agonism in the GLP-1R HEK293 Cell Membrane Guanosine 5'-(gamma-thio) Triphosphate-[$^{35}$S] (GTPγS) Binding Assay is administered as an active agent within one week before or after a compound having GIP agonist activity. In an embodiment, a method for treating diabetes comprises administering an effective amount of a compound showing 35% or less in the GLP-CHO Cell β-Arrestin. Recruitment Assay and administering an effective amount of a compound showing partial agonism of 75% or less in the GLP-1R HEK293 Cell Membrane Guanosine 5'-(gamma-thio) Triphosphate-[$^{35}$S] (GTPγS) Binding Assay.

GLP-1R HEK293 Cell Membrane [$^{35}$S]GTPγS Binding Assay

The GLP-1 receptor is a G-protein coupled receptor that increases GTP-bound Gα$_s$ upon ligand induced receptor activation. The potency of peptides to stimulate-GLP-1R induced activation of Gα$_s$ is determined using preparations of purified membranes from HEK293 cells expressing the human GLP-1R. The assay is performed similarly to that as previously described (Bueno et al., J. Biol. Chem., (2016) 291, 10700 and Willard et al., Mol. Pharmacol. (2012) 82, 1066). The test peptides are solubilized in DMSO and diluted in reaction buffer containing 5 µg of membrane in 20 mM HEPES pH 7.4, 50 mM NaCl, 5 mM MgCl$_2$, 40 µg/ml saponin, 0.1% BSA, and 500 pM $^{35}$S-labeled GTPγS for 30 minutes at room temperature. Reactions are terminated by addition of 0.2% Nonidet P-40 detergent containing rabbit anti-Gα$_s$ polyclonal antibody and 0.5 mg of anti-rabbit polyvinyltoluene beads. Mixtures are developed for 30 minutes, centrifuged at 80×g for 10 minutes, and counted for 1 minute/well using a MicroBeta TriLux instrument. Peptide concentration-response curves are fit to a four-parameter logistic model to calculate potency as an EC$_{50}$. Data normalization to % stimulation is performed using DMSO and GLP-1 (7-36) as minimum and maximum controls for the receptor (Campbell et al, Assay Guidance Manual 2017). The potency of a sample peptide to stimulate GIPR induced activation of Gα$_s$ is determined. Assay results identify a peptide that is a partial agonist on the GLP-1R with respect to GLP-1R induced activation of Gα$_s$.

GLP-1R CHO Cell β-Arrestin Recruitment Assay

Activated G-protein coupled receptors can interact with the β-arrestin family of signalling proteins. The potency of peptides for GLP-1R induced arrestin recruitment is determined using the PathHunter Enzyme Fragment Complementation approach substantially as described (von Degenfeld et al., FASEB J., 2007 (14): 3819-26 and Hamdouchi et al., J. Med Chem., 2016 59 (24): 10891-10916). CHO-K1 cells expressing Pro-Link-tagged Human GLP-1R and enzyme-acceptor-tagged β-arrestin-2 may be obtained from DiscoveRx and prepared as assay-ready frozen cells. Test peptides are solubilized in DMSO and serial dilutions are perfomed using the Echo acoustic dispenser (LabCyte). Assay media is the PathHunter Cell Assay Buffer (DiscoveRx) containing 0.1% w/v hydrolyzed Casein (Sigma). 100 nl of peptide is dispensed into 10 µl of assay media in a 384 well plate and then 10 µl of cells in assay media are added to give 5000 cells per well. Plates are incubated for 90 minutes in a 37'C/5% C02 incubator and 10 µl of PathHunter detection reagent is added (DiscoveRx) and plates are incubated at room temperature for 60 minutes. Luminescence signal is measured. Peptide concentration-response curves fit to a four-parameter logistic model to calculate potency as an EC50. Data normalization to % stimulation is performed using DMSO and GLP-1 (7-36) as minimum and maximum controls (Campbell et al, Assay Guidance Manual 2017). The potency of a sample peptide to stimulate GLP-1R induced β-arrestin recruitment is determined. Assay results identify a peptide that is a partial agonist on the GLP-1R with respect to β-arrestin-2 recruitment.

Clinical Study to Determine GIP:GLP-1 Peptide Maintenance Dose

A 6-month (26-week) Phase 2 double-blind clinical study is designed to evaluate the safety, efficacy, and PK/PD of 4 dose levels (1 mg, 5 mg, 10 mg and 15 mg respectively) of a GIP:GLP-1 Peptide administered once weekly by subcutaneous injection compared with dulaglutide 1.5 mg administered once weekly (QW) and placebo QW in patients with T2DM who have inadequate glycemic control with diet and exercise with or without a stable dose of metformin. The GIP:GLP Peptide dose was up-titrated to the maintenance dose using the following weekly dose increments:

| GIP: GLP-1 Peptide dose: | Weekly GIP: GLP-1 Peptide Dose Increments: |
|---|---|
| 1 mg | Week 0-26: 1 mg QW |
| 5 mg | Week 0-26: 5 mg QW |
| 10 mg | Week 0: 5 mg |
|  | Week 1: 5 mg |
|  | Week 2-26: 10 mg |
| 15 mg | Week 0: 5 mg |
|  | Week 1: 5 mg |
|  | Week 2: 10 mg |
|  | Week 3: 10 mg |
|  | Week 4: 10 mg |
|  | Week 5: 10 mg |
|  | Week 6-26: 15 mg |

The study also has a 4-week follow up period. In addition to safety and efficacy for treating T2DM, efficacy endpoints include the effect of the GIP:GLP-1 Peptide on HbA1c, FBG, body weight, lipids, and waist circumference compared with placebo and with dulaglutide 1.5 mg. The study also evaluates the effect of the GIP:GLP-1 Peptide on GI tolerability, hypoglycemia, hypersensitivity reactions, and pancreatic safety, as well as the development of treatment-emergent anti-drug antibodies. Model-based dose response analyses are performed to predict potential for significant HbA1c lowering and weight loss in longer studies.

Statistical Analyses:

Efficacy: The primary efficacy outcome of HbA1c change from baseline to the 26-week endpoint is analyzed using a Bayesian dose-response model. Analyses are performed on the intention to treat population (mITT) analysis set. Supportive analysis of the primary efficacy outcome for the mITT dataset are the model for post-baseline measures (MMRM) with body mass index (BMI) (<30 kg/m$^2$, ≥30 kg/m$^2$), metformin use, treatment, visit, and treatment-by-visit interaction as fixed effects, baseline HbA1c as a covariate, and patient as a random effect.

The mean weight change from baseline at 12 and 26 weeks, along with the mean change from baseline of HbA1c at 12 weeks, is analyzed using similar dose-response models as the primary analyses. The percentages of patients with ≥5% or ≥10% body weight loss, reaching the HbA1c target of ≤6.5% or ≤7.0% at 26 weeks, or requiring rescue therapy are analyzed using logistic regression with fixed effects of treatment and strata, and baseline as a covariate. The changes from baseline in FBG (fasting blood glucose), SMBG (self-monitored blood glucose) levels, waist circumference, and mean percentage change in lipids from baseline to 12 and 26 weeks are analyzed using a similar MMRM to the one used for the primary analyses.

Clinical Study to Determine GIP:GLP-1 Peptide Titration Schedule

This is a 12-week treatment with a 1 week screening (Visit 1) followed by a 1 week lead-in (Visit 2), then 12 weeks of treatment (Visits 3-10, including telephone visits), then followed by 4-week safety follow-up. It is a Phase 2 study designed to examine the efficacy and tolerability of subcutaneously once-weekly administration of a GIP:GLP-1 Peptide compared with placebo in patients with type 2 diabetes who have inadequate glycemic control with diet and exercise alone or with a stable dose of metformin. The study was designed per below and conducted to refine the titration scheme.

| GIP: GLP-1 Peptide Dose: | Weekly GIP: GLP-1 Peptide Dose Increments: |
|---|---|
| Placebo | Week 1-12 |
| Group 1 | Weeks 1-2: 2.5 mg |
| | Weeks 3-4: 5 mg |
| | Weeks 5-8: 10 mg |
| | Weeks 9-12: 15 mg |
| Group 2 | Weeks 1-4: 2.5 mg |
| | Weeks 5-8: 7.5 mg |
| | Weeks 9-12: 15 mg |
| Group 3 | Weeks 1-4: 4 mg |
| | Weeks 5-8: 8 mg |
| | Weeks 9-12: 12 mg |

Amino Acid Sequences
GIP (Human)
SEQ ID NO: 1
YAEGTFISDYSIAMDKIHQQDFVNWLLAQKGKKNDWKHNITQ GLP-1 (7-36) (Human)
SEQ ID NO: 2
HAEGTFTSDVSSYLEGQAAKEFIAWLVKGR-NH$_2$ SEQ ID NO: 3
$R_1X_1\ X_2\ X_3GT\ X_6TSD\ X_{10}\ X_{11}\ X_{12}\ X_{13}\ X_{14}D\ X_{16}X_{17}AX_{19}\ X_{20}\ X_{21}\ X_{22}X_{23}\ X_{24}\ X_{25}\ X_{26}\ X_{27}\ X_{28}\ X_{29}\ X_{30}X_{31}$

SEQ ID NO: 4
$PX_{32}\ X_{33}\ X_{34}$-$R_2$

SEQ ID NO: 5
$PX_{32}\ X_{33}\ X_{34}\ X_{35}X_{36}\ X_{37}\ X_{38}\ X_{39}$-$R_2$

SEQ ID NO: 6
$PX_{32}\ X_{33}\ X_{34}\ X_{35}X_{36}\ X_{37}\ X_{38}\ X_{39}\ X_{40}$-$R_2$

SEQ ID NO: 7
K[(2-[2-(2-Amino-ethoxy)-ethoxy]-acetyl)$_2$-γGlu-CO-(CH$_2$)$_q$-CO$_2$H] $X_{32}\ X_{33}\ X_{34}$-$R_2$ SEQ ID NO: 8
K[(2-[2-(2-Amino-ethoxy)-ethoxy]-acetyl)$_2$-γGlu-CO-(CH$_2$)$_q$-CO$_2$H] $X_{32}\ X_{33}\ X_{34}\ X_{35}X_{36}\ X_{37}\ X_{38}\ X_{39}$-$R_2$ SEQ ID NO: 9
K[(2-[2-(2-Amino-ethoxy)-ethoxy]-acetyl)$_2$-γGlu-CO-(CH$_2$)$_q$-CO$_2$H] $X_{32}\ X_{33}\ X_{34}\ X_{35}X_{36}\ X_{37}\ X_{38}\ X_{39}\ X_{40}$-$R_2$

SEQUENCE LISTING

```
<160> NUMBER OF SEQ ID NOS: 145

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
```

<223> OTHER INFORMATION: AMIDATION

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic construct; Formula I
<220> FEATURE:
<221> NAME/KEY: VARIANT
<222> LOCATION: (1)..(1)
<223> OTHER INFORMATION: Xaa at position 1 is selected from the group
      consisting of Y, H, D-Tyr, F, desH, and desY, or Xaa at position 1
      and Xaa at position 2 combine to form desH-psi[NHCO]-Aib
<220> FEATURE:
<221> NAME/KEY: MOD_RES
<222> LOCATION: (1)..(1)
<223> OTHER INFORMATION: The N-terminus of Xaa at position 1 is modified
      with R1, wherein the modification is selected from the group
      consisting of Ac and absent.
<220> FEATURE:
<221> NAME/KEY: VARIANT
<222> LOCATION: (2)..(2)
<223> OTHER INFORMATION: Xaa at position 2 is selected from the group
      consisting of Aib, alpha-MeP, A, P, and D-Ala, or Xaa at position
      1 combines with Xaa at position 2 to form desH-psi[NHCO]-Aib
<220> FEATURE:
<221> NAME/KEY: VARIANT
<222> LOCATION: (3)..(3)
<223> OTHER INFORMATION: Xaa at position 3 is selected from the group of
      E, N, Aad, and cTA
<220> FEATURE:
<221> NAME/KEY: VARIANT
<222> LOCATION: (6)..(6)
<223> OTHER INFORMATION: Xaa at position 6 is selected from the group
      consisting of F, alpha-MeF, and alpha-MeF(2F)
<220> FEATURE:
<221> NAME/KEY: VARIANT
<222> LOCATION: (10)..(10)
<223> OTHER INFORMATION: Xaa at position 10 is selected from the group
      consisting of A, L, H, 3Pal, 4Pal, V, Y, E, alpha-MeF, alpha-
      MeF(2F), I, alpha-MeY, Q, D-His, D-Tyr, cTA, and K
<220> FEATURE:
<221> NAME/KEY: VARIANT
<222> LOCATION: (10)..(10)
<223> OTHER INFORMATION: when Xaa at position 10 is K, then K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: MISC_FEATURE
<222> LOCATION: (10)..(31)
<223> OTHER INFORMATION: When Xaa is
      K(2-[2-(2-amino-ethoxy)-ethoxy]-acetyl)2-(gamma-Glu)-CO-(CH2)q-
      CO2H at positions 10, 12, 13, 14, 16, 17, 19, 20, 21, 23, 24, 26,
      27, 28, 29, 30 or 31, q is 14, 15, 16, 17, 18, 19 or 20.
<220> FEATURE:
<221> NAME/KEY: VARIANT
<222> LOCATION: (11)..(11)
<223> OTHER INFORMATION: Xaa at position 11 is selected from the group
      consisting of S, alpha-MeS, or D-Ser
<220> FEATURE:
<221> NAME/KEY: VARIANT
<222> LOCATION: (12)..(12)
<223> OTHER INFORMATION: Xaa at position 12 is selected from the group
      consisting of I, S, D-Ile, and K
<220> FEATURE:
<221> NAME/KEY: MOD_RES
<222> LOCATION: (12)..(12)
<223> OTHER INFORMATION: when Xaa at position 12 is K, then K is

```
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (13)..(13)
<223> OTHER INFORMATION: Xaa at position 13 is selected from the group
        consisting of Nle, Aib, L, alpha-MeL, and K
<220> FEATURE:
<221> NAME/KEY: MOD_RES
<222> LOCATION: (13)..(13)
<223> OTHER INFORMATION: when Xaa at position 13 is K, then K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (14)..(14)
<223> OTHER INFORMATION: Xaa at position 14 is selected from the group
        consisting of L and K, wherein K is conjugated to a C16-C22 fatty
        acid wherein said fatty acid is optionally conjugated to said K
        via a linker
<220> FEATURE:
<221> NAME/KEY: VARIANT
<222> LOCATION: (16)..(16)
<223> OTHER INFORMATION: Xaa at position 16 is selected from the group
        consisting of E, Orn, Dab, Dap, S, T, H, Aib, alpha-MeK, R, and K
<220> FEATURE:
<221> NAME/KEY: MOD_RES
<222> LOCATION: (16)..(16)
<223> OTHER INFORMATION: when Xaa at position 16 is K, then K is
        optionally chemically modified by conjugation of the epsilon-amino
        group of the K side chain with (2-[2-(2-amino-ethoxy)-ethoxy]-
        acetyl)2-(gamma-Glu)-CO-(CH2)q-CO2H
<220> FEATURE:
<221> NAME/KEY: VARIANT
<222> LOCATION: (17)..(17)
<223> OTHER INFORMATION: Xaa at position 17 is selected from the group
        consisting of K, Q, I, and an amino acid conjugated to a C16-C22
        fatty acid wherein said fatty acid is optionally conjugated to
        said amino acid via a linker
<220> FEATURE:
<221> NAME/KEY: VARIANT
<222> LOCATION: (19)..(19)
<223> OTHER INFORMATION: Xaa at position 19 is selected from the group
        consisting of Q, A, and K
<220> FEATURE:
<221> NAME/KEY: MOD_RES
<222> LOCATION: (19)..(19)
<223> OTHER INFORMATION: when Xaa at position 19 is K, then K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (20)..(20)
<223> OTHER INFORMATION: Xaa at position 20 is selected from the group
        consisting of Aib, Q, H, R, K, and alpha-MeK
<220> FEATURE:
<221> NAME/KEY: MOD_RES
<222> LOCATION: (20)..(20)
<223> OTHER INFORMATION: when Xaa at position 20 is K, then K  is
        optionally chemically modified by conjugation of the epsilon-amino
        group of the K side chain with (2-[2-(2-amino-ethoxy)-ethoxy]-
        acetyl)2-(gamma-Glu)-CO-(CH2)q-CO2H
<220> FEATURE:
<221> NAME/KEY: VARIANT
<222> LOCATION: (21)..(21)
<223> OTHER INFORMATION: Xaa at position 21 is selected from the group
        consisting of H, Aad, D, Aib, T, A, E, I, and K
<220> FEATURE:
<221> NAME/KEY: MOD_RES
<222> LOCATION: (21)..(21)
<223> OTHER INFORMATION: when Xaa at position 21 is K, then K is
        chemically modified by conjugation of the epsilon-amino group of
        the K side chain with K(2-[2-(2-amino-ethoxy)-ethoxy]-acetyl)2-
        (gamma-Glu)-CO-(CH2)q-CO2H
<220> FEATURE:
<221> NAME/KEY: VARIANT
```

-continued

```
<222> LOCATION: (22)..(22)
<223> OTHER INFORMATION: Xaa at position 22 is selected from the group
      consisting of F and alpha-MeF
<220> FEATURE:
<221> NAME/KEY: VARIANT
<222> LOCATION: (23)..(23)
<223> OTHER INFORMATION: Xaa at position 23 is selected from the group
      consisting of I, L, A, G, F, H, E, V, and K
<220> FEATURE:
<221> NAME/KEY: MOD_RES
<222> LOCATION: (23)..(23)
<223> OTHER INFORMATION: when Xaa at position 23 is K, then K is
      chemically modified by conjugation of the epsilon-amino group of
      the K side chain with K(2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (24)..(24)
<223> OTHER INFORMATION: Xaa at position 24 is selected from the group
      consisting of S, Aad, D-Glu, E, Aib, H, V, A, Q, D, P, and K
<220> FEATURE:
<221> NAME/KEY: MOD_RES
<222> LOCATION: (24)..(24)
<223> OTHER INFORMATION: when Xaa at position 24 is K, then K is
      chemically modified by conjugation of the epsilon-amino group of
      the K side chain with K(2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (25)..(25)
<223> OTHER INFORMATION: Xaa at position 25 is selected from the group
      consisting of Y or alpha-MeY
<220> FEATURE:
<221> NAME/KEY: VARIANT
<222> LOCATION: (26)..(26)
<223> OTHER INFORMATION: Xaa at position 26 is selected from the group
      consisting of L, alpha-MeL, and K
<220> FEATURE:
<221> NAME/KEY: MOD_RES
<222> LOCATION: (26)..(26)
<223> OTHER INFORMATION: when Xaa at position 26 is K, then K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (27)..(27)
<223> OTHER INFORMATION: Xaa at position 27 is selected from the group
      consisting of L, I, and K
<220> FEATURE:
<221> NAME/KEY: MOD_RES
<222> LOCATION: (27)..(27)
<223> OTHER INFORMATION: when Xaa at position 27 is K, then K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (28)..(28)
<223> OTHER INFORMATION: Xaa at position 28 is selected from the group
      consisting of E, A, S, D-Glu, and K
<220> FEATURE:
<221> NAME/KEY: MOD_RES
<222> LOCATION: (28)..(28)
<223> OTHER INFORMATION: when Xaa at position 28 is K, then K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (29)..(29)
<223> OTHER INFORMATION: Xaa at position 29 is selected from the group
      consisting of Aib, G, A, and K
<220> FEATURE:
<221> NAME/KEY: MOD_RES
<222> LOCATION: (29)..(29)
<223> OTHER INFORMATION: when Xaa at position 29 is K, then K is
      chemically modified by conjugation of the epsilon-amino group of
      the K side chain with (2-[2-(2-amino-ethoxy)-ethoxy]-acetyl)2-
```

```
        (gamma-Glu)-CO-(CH2)q-CO2H
<220> FEATURE:
<221> NAME/KEY: VARIANT
<222> LOCATION: (30)..(30)
<223> OTHER INFORMATION: Xaa at position 30 is selected from the group
      consisting of C, G, G-R2, and K, wherein R2 is a modification of
      the C-terminal group, wherein the modification is NH2 or absent,
      wherein if X30 is G-R2, then X31 is absent.
<220> FEATURE:
<221> NAME/KEY: MOD_RES
<222> LOCATION: (30)..(30)
<223> OTHER INFORMATION: when Xaa at position 30 is K, then K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (31)..(31)
<223> OTHER INFORMATION: Xaa at position 31 is absent or is selected
      from the group consisting of SEQ ID NO:4, SEQ ID NO:5, SEQ ID:6,
      SEQ ID NO:7, SEQ ID NO:8, and SEQ ID NO:9
<220> FEATURE:
<221> NAME/KEY: MISC_FEATURE
<222> LOCATION: (31)..(31)
<223> OTHER INFORMATION: wherein no more than one of X10, X12, X13, X14,
      X16, X17, X19, X20, X21, X23, X24, X26, X27, X28, X29, X30, X31,
      X32, X33, X34, X35, X36, X37, X38, X39, and X40 may be a
      substituent that contains a fatty acid
<220> FEATURE:
<221> NAME/KEY: MISC_FEATURE
<222> LOCATION: (31)..(31)
<223> OTHER INFORMATION: wherein no more than one of X30, X34, X39, and
      X40 may be C
<220> FEATURE:
<221> NAME/KEY: MISC_FEATURE
<222> LOCATION: (31)..(31)
<223> OTHER INFORMATION: wherein if one of X30, X34, X39, and X40 is C,
      then none of X10, X12, X13, X14, X16, X17, X19, X20, X21, X23,
      X24, X26, X27, X28, X29, X30, X31, X32, X33, X34, X35, X36, X37,
      X38, X39, and X40 is a substituent that contains a fatty acid
<220> FEATURE:
<221> NAME/KEY: MOD_RES
<222> LOCATION: (31)..(31)
<223> OTHER INFORMATION: Xaa at position 31 is modified with R2, wherein
      the modification is NH2 to form a C-terminal amide or absent

<400> SEQUENCE: 3

Xaa Xaa Xaa Gly Thr Xaa Thr Ser Asp Xaa Xaa Xaa Xaa Xaa Asp Xaa
1               5                   10                  15
Xaa Ala Xaa Xaa Xaa Xaa Xaa Xaa Xaa Xaa Xaa Xaa Xaa Xaa
            20                  25                  30

<210> SEQ ID NO 4
<211> LENGTH: 4
<212> TYPE: PRT
<213> ORGANISM: Artificial Sequence
<220> FEATURE:
<223> OTHER INFORMATION: Synthetic construct; SEQ ID NO:4 is PX32X33X34
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: MISC_FEATURE
<222> LOCATION: (2)..(4)
<223> OTHER INFORMATION: wherein q is selected from the group consisting
      of 14, 15, 16, 17, 18, 19, and 20.
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with (2-[2-(2-amino-ethoxy)-ethoxy]-acetyl)2-
```

```
        (gamma-Glu)-CO-(CH2)q-CO2H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: MOD_RES
<222> LOCATION: (4)..(4)
<223> OTHER INFORMATION: The C-terminal group of Xaa at position 4 is
      modified with R2, wherein the modification is NH2 to form a
      C-terminal amide or absent

<400> SEQUENCE: 4

Pro Xaa Xaa Xaa
1

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct; SEQ ID NO:5 is
      PX32X33X34X35X36X37X38X39
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: MISC_FEATURE
<222> LOCATION: (2)..(9)
<223> OTHER INFORMATION: wherein q is selected from the group consisting
      of 14, 15, 16, 17, 18, 19, and 20.
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (6)..(6)
<223> OTHER INFORMATION: Xaa at position 6 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (7)..(7)
<223> OTHER INFORMATION: Xaa at position 7 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (8)..(8)
<223> OTHER INFORMATION: Xaa at position 8 is P or K, wherein K is
``` chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (9)..(9)
<223> OTHER INFORMATION: Xaa at position 9 is C, S or K, wherein K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: MOD_RES
<222> LOCATION: (9)..(9)
<223> OTHER INFORMATION: The C-terminal group of Xaa at position 9 is
        modified with R2, wherein the modification is NH2 to from a
        C-terminal amide or absent

<400> SEQUENCE: 5

Pro Xaa Xaa Xaa Xaa Xaa Xaa Xaa Xaa
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct; SEQ ID NO:6 is
        PX32X33X34X35X36X37X38X39X40
<220> FEATURE:
<221> NAME/KEY: VARIANT
<222> LOCATION: (2)..(2)
<223> OTHER INFORMATION: Xaa at position 2 is S or K, wherein K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: MISC_FEATURE
<222> LOCATION: (2)..(10)
<223> OTHER INFORMATION: wherein q is selected from the group consisting
        of 14, 15, 16, 17, 18, 19, and 20.
<220> FEATURE:
<221> NAME/KEY: VARIANT
<222> LOCATION: (3)..(3)
<223> OTHER INFORMATION: Xaa at position 3 is S or K, wherein K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (4)..(4)
<223> OTHER INFORMATION: Xaa at position 4 is G, C or K, wherein K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (6)..(6)
<223> OTHER INFORMATION: Xaa at position 6 is P or K, wherein K is
        chemically modified by conjugation of the epsilon-amino group of
        the K side chain with (2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (7)..(7)
<223> OTHER INFORMATION: Xaa at position 7 is P or K, wherein K is
        chemically modified by conjugation of the epsilon-amino group of
        the K side chain with K(2-[2-(2-amino-ethoxy)-ethoxy]-acetyl)2-
        (gamma-Glu)-CO-(CH2)q-CO2H
<220> FEATURE:
<221> NAME/KEY: VARIANT
<222> LOCATION: (8)..(8)
<223> OTHER INFORMATION: Xaa at position 8 is P or K, wherein K is
      chemically modified by conjugation of the epsilon-amino group of
      the K side chain with K(2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (9)..(9)
<223> OTHER INFORMATION: Xaa at position 9 is C, S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (10)..(10)
<223> OTHER INFORMATION: Xaa at position 10 is C or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: MOD_RES
<222> LOCATION: (10)..(10)
<223> OTHER INFORMATION: The C-terminal group of Xaa at position 10 is
      modified with R2, wherein the modification is NH2 to form a
      C-terminal amide or absent

<400> SEQUENCE: 6

Pro Xaa Xaa Xaa Xaa Xaa Xaa Xaa Xaa Xaa
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct; SEQ ID NO:7 is
      K[(2-[2-(2-amino-ethoxy)-ethoxy]-acetyl)2-(gamma-Glu)-CO-(CH2)q-
      CO2H]X32X33X34
<220> FEATURE:
<221> NAME/KEY: MOD_RES
<222> LOCATION: (1)..(1)
<223> OTHER INFORMATION: K is chemically modified by conjugation of the
      epsilon-amino group of the K side chain with (2-[2-(2-amino-
      ethoxy)-ethoxy]-acetyl)2-(gamma-Glu)-CO-(CH2)q-CO2H
<220> FEATURE:
<221> NAME/KEY: MISC_FEATURE
<222> LOCATION: (1)..(1)
<223> OTHER INFORMATION: wherein q is selected from the group consisting
      of 14, 15, 16, 17, 18, 19, and 20
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: MOD_RES
<222> LOCATION: (4)..(4)
<223> OTHER INFORMATION: The C-terminal group of Xaa at position 4 is
      modified with R2, wherein the modification is NH2 to form a
      C-terminal amide or absent

```
<400> SEQUENCE: 7

Lys Xaa Xaa Xaa
1

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct; SEQ ID NO:8 is
      K[(2-[2-(2-amino-ethoxy)-ethoxy]-acetyl)2-(gamma-Glu)-CO-(CH2)q-
      CO2H]X32X33X34X35X36X37X38X39
<220> FEATURE:
<221> NAME/KEY: MOD_RES
<222> LOCATION: (1)..(1)
<223> OTHER INFORMATION: K is chemically modified by conjugation of the
      epsilon-amino group of the K side chain with (2-[2-(2-amino-
      ethoxy)-ethoxy]-acetyl)2-(gamma-Glu)-CO-(CH2)q-CO2H
<220> FEATURE:
<221> NAME/KEY: MISC_FEATURE
<222> LOCATION: (1)..(1)
<223> OTHER INFORMATION: wherein q is selected from the group consisting
      of 14, 15, 16, 17, 18, 19, and 20
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (6)..(6)
<223> OTHER INFORMATION: Xaa at position 6 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (7)..(7)
<223> OTHER INFORMATION: Xaa at position 7 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (8)..(8)
<223> OTHER INFORMATION: Xaa at position 8 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (9)..(9)
<223> OTHER INFORMATION: Xaa at position 9 is C, S or K, wherein K is
      chemically modified by conjugation of the epsilon-amino group of
```

```
      the K side chain with (2-[2-(2-amino-ethoxy)-ethoxy]-acetyl)2-
      (gamma-Glu)-CO-(CH2)q-CO2
<220> FEATURE:
<221> NAME/KEY: MOD_RES
<222> LOCATION: (9)..(9)
<223> OTHER INFORMATION: The C-terminal group of Xaa at position 9 is
      modified with R2, wherein the modification is NH2 to form a
      C-terminal amide or absent

<400> SEQUENCE: 8

Lys Xaa Xaa Xaa Xaa Xaa Xaa Xaa Xaa
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct; SEQ ID NO:9 is
      K[(2-[2-(2-amino-ethoxy)-ethoxy]-acetyl)2-(gamma-Glu)-CO-(CH2)q-
      CO2H]X32X33X34X35X36X37X38X39X40
<220> FEATURE:
<221> NAME/KEY: MOD_RES
<222> LOCATION: (1)..(1)
<223> OTHER INFORMATION: K is chemically modified by conjugation of the
      epsilon-amino group of the K side chain with (2-[2-(2-amino-
      ethoxy)-ethoxy]-acetyl)2-(gamma-Glu)-CO-(CH2)q-CO2H
<220> FEATURE:
<221> NAME/KEY: MISC_FEATURE
<222> LOCATION: (1)..(1)
<223> OTHER INFORMATION: wherein q is selected from the group consisting
      of 14, 15, 16, 17, 18, 19, and 20
<220> FEATURE:
<221> NAME/KEY: VARIANT
<222> LOCATION: (2)..(2)
<223> OTHER INFORMATION: Xaa at position 2 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (3)..(3)
<223> OTHER INFORMATION: Xaa at position 3 is S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (4)..(4)
<223> OTHER INFORMATION: Xaa at position 4 is G, C or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (5)..(5)
<223> OTHER INFORMATION: Xaa at position 5 is A or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (6)..(6)
<223> OTHER INFORMATION: Xaa at position 6 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (7)..(7)
<223> OTHER INFORMATION: Xaa at position 7 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (8)..(8)
```

```
<223> OTHER INFORMATION: Xaa at position 8 is P or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: VARIANT
<222> LOCATION: (9)..(9)
<223> OTHER INFORMATION: Xaa at position 9 is C, S or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME
<222> LOCATION: (10)..(10)
<223> OTHER INFORMATION: Xaa at position 10 is C or K, wherein K is
      chemically modified by conjugation of the epsilon-amino group of
      the K side chain with (2-[2-(2-amino-ethoxy)-ethoxy]-acetyl)2-
      (gamma-Glu)-CO-(CH2)q-CO2H
<220> FEATURE:
<221> NAME/KEY: MOD_RES
<222> LOCATION: (10)..(10)
<223> OTHER INFORMATION: The C-terminal group of Xaa at position 10 is
      modified with R2, wherein the modification is NH2 to form a
      C-terminal amide or absent

<400> SEQUENCE: 9

Lys Xaa Xaa Xaa Xaa Xaa Xaa Xaa Xaa Xaa
1               5                   10

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: The Serine at position 39 is amidated

<400> SEQUENCE: 10

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Ser
            35
```

```
<210> SEQ ID NO 11
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: The Serine at position 39 is amidated

<400> SEQUENCE: 11

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
```

```
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (39)..(39)
<223> OTHER INFORMATION: The Serine at position 39 is amidated

<400> SEQUENCE: 12

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-MeY
<220> FEATURE:
<221> NAME/KEY: MOD_RES
<222> LOCATION: (39)..(39)
```

```
<223> OTHER INFORMATION: The Serine at position 39 is amidated

<400> SEQUENCE: 13

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 14

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 15
```

```
Tyr Xaa Glu Gly Thr Phe Thr Ser Asp Tyr Ser Ile Leu Leu Asp Ser
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
            35

<210> SEQ ID NO 16
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 16

Tyr Xaa Glu Gly Thr Phe Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
            35

<210> SEQ ID NO 17
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
```

```
<221> NAME/KEY: MOD_RES
<222> LOCATION: (39)..(39)
<223> OTHER INFORMATION: Ser at position 39 is amidated

<400> SEQUENCE: 17

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is alpha-methyl-Lys
<220> FEATURE:
<221> NAME/KEY: MISC_FEATURE
<222> LOCATION: (29)..(29)
<223> OTHER INFORMATION: Xaa at position 29 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 18

Tyr Xaa Glu Gly Thr Phe Thr Ser Asp Tyr Ser Ile Xaa Leu Asp Glu
1               5                   10                  15

Lys Ala Gln Xaa Ala Phe Ile Glu Tyr Leu Leu Glu Xaa Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (12)..(12)
<223> OTHER INFORMATION: Lys at position 12 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
```

```
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 19

Tyr Xaa Glu Gly Thr Phe Thr Ser Asp Tyr Ser Lys Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 20
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (13)..(13)
<223> OTHER INFORMATION: Lys at position 13 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 20

Tyr Xaa Glu Gly Thr Phe Thr Ser Asp Tyr Ser Ile Lys Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 21
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (16)..(16)
<223> OTHER INFORMATION: Lys at position 16 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
```

```
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 21

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (19)..(19)
<223> OTHER INFORMATION: Lys at position 19 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 22

Tyr Xaa Glu Gly Thr Phe Thr Ser Asp Tyr Ser Ile Leu Leu Asp Lys
1               5                   10                  15

Ile Ala Lys Xaa Ala Phe Ile Glu Tyr Leu Ile Glu Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (21)..(21)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
```

```
<222> LOCATION: (39)..(39)
<223> OTHER INFORMATION: Ser at position 39 is amidated

<400> SEQUENCE: 23

Tyr Xaa Glu Gly Thr Phe Thr Ser Asp Tyr Ser Ile Leu Leu Asp Lys
1               5                   10                  15

Ile Ala Gln Xaa Lys Phe Ile Glu Tyr Leu Ile Glu Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (23)..(23)
<223> OTHER INFORMATION: Lys at position 23 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is amidated

<400> SEQUENCE: 24

Tyr Xaa Glu Gly Thr Phe Thr Ser Asp Tyr Ser Ile Leu Leu Asp Lys
1               5                   10                  15

Ile Ala Gln Xaa Ala Phe Lys Glu Tyr Leu Ile Glu Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (24)..(24)
<223> OTHER INFORMATION: Lys at position 24 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is amidated
```

-continued

```
<400> SEQUENCE: 25

Tyr Xaa Glu Gly Thr Phe Thr Ser Asp Tyr Ser Ile Leu Leu Asp Lys
1               5                   10                  15

Ile Ala Gln Xaa Ala Phe Ile Lys Tyr Leu Ile Glu Gly Gly Pro Ser
                20                  25                  30

Ser Gly Ala Pro Pro Pro Ser
            35

<210> SEQ ID NO 26
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is amidated

<400> SEQUENCE: 26

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Lys Gly Gly Pro Ser
                20                  25                  30

Ser Gly Ala Pro Pro Pro Ser
            35

<210> SEQ ID NO 27
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (32)..(32)
<223> OTHER INFORMATION: Lys at position 32 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is amidated

<400> SEQUENCE: 27

Tyr Xaa Glu Gly Thr Phe Thr Ser Asp Tyr Ser Ile Leu Leu Asp Lys
```

```
                1               5                  10                 15
Ile Ala Gln Xaa Ala Phe Ile Glu Tyr Leu Ile Glu Gly Gly Pro Lys
                20                 25                 30

Ser Gly Ala Pro Pro Pro Ser
                35
```

<210> SEQ ID NO 28
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (37)..(37)
<223> OTHER INFORMATION: Lys at position 37 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is amidated

<400> SEQUENCE: 28

```
Tyr Xaa Glu Gly Thr Phe Thr Ser Asp Tyr Ser Ile Leu Leu Asp Lys
1               5                  10                 15

Ile Ala Gln Xaa Ala Phe Ile Glu Tyr Leu Ile Glu Gly Gly Pro Ser
                20                 25                 30

Ser Gly Ala Pro Lys Pro Ser
                35
```

<210> SEQ ID NO 29
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (38)..(38)
<223> OTHER INFORMATION: Lys at position 38 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Ser at position 39 is amidated

<400> SEQUENCE: 29

```
Tyr Xaa Glu Gly Thr Phe Thr Ser Asp Tyr Ser Ile Leu Leu Asp Lys
1               5                  10                 15

Ile Ala Gln Xaa Ala Phe Ile Glu Tyr Leu Ile Glu Gly Gly Pro Ser
```

```
                    20                  25                  30

Ser Gly Ala Pro Pro Lys Ser
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Lys at position 39 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (39)..(39)
<223> OTHER INFORMATION: Lys at position 39 is amidated

<400> SEQUENCE: 30

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Glu Gly Gly Pro Ser
            20                  25                  30

Ser Gly Ala Pro Pro Pro Lys
        35

<210> SEQ ID NO 31
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 31

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly
```

```
<210> SEQ ID NO 32
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 32

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly
            20                  25                  30

<210> SEQ ID NO 33
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 33

Tyr Xaa Glu Gly Thr Phe Thr Ser Asp Tyr Ser Ile Xaa Leu Asp Ser
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35
```

```
<210> SEQ ID NO 34
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 34

Tyr Xaa Glu Gly Thr Phe Thr Ser Asp Tyr Ser Ile Xaa Leu Asp Xaa
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 35
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 35

Tyr Xaa Glu Gly Thr Phe Thr Ser Asp Tyr Ser Ile Xaa Leu Asp Lys
```

```
                1               5                  10                 15
Lys Ala Gln Xaa Ala Phe Ile Glu Tyr Leu Ile Glu Gly Gly
                20                 25                 30
```

<210> SEQ ID NO 36
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 36

```
Tyr Xaa Glu Gly Thr Phe Thr Ser Asp Tyr Ser Ile Xaa Leu Asp Glu
1               5                  10                 15
Lys Ala Gln Xaa Ala Phe Ile Glu Tyr Leu Ile Glu Gly Gly
                20                 25                 30
```

<210> SEQ ID NO 37
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 37

```
Tyr Xaa Glu Gly Thr Phe Thr Ser Asp Tyr Ser Ile Xaa Leu Asp Ser
1               5                  10                 15
```

```
Lys Ala Gln Xaa Ala Phe Ile Glu Tyr Leu Ile Glu Gly Gly
            20                  25                  30
```

<210> SEQ ID NO 38
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 38

```
Tyr Xaa Glu Gly Thr Phe Thr Ser Asp Tyr Ser Ile Xaa Leu Asp Thr
1               5                   10                  15
Lys Ala Gln Xaa Ala Phe Ile Glu Tyr Leu Ile Glu Gly Gly
            20                  25                  30
```

<210> SEQ ID NO 39
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 39

```
Tyr Xaa Glu Gly Thr Phe Thr Ser Asp Tyr Ser Ile Xaa Leu Asp Glu
1               5                   10                  15
```

Lys Ala Gln Xaa Ala Phe Ile Glu Tyr Leu Leu Glu Gly Gly Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (11)..(11)
<223> OTHER INFORMATION: Xaa at position 11 is alpha-methyl-Ser
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 40

Tyr Xaa Glu Gly Thr Phe Thr Ser Asp Tyr Xaa Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:

```
<221> NAME/KEY: MOD_RES
<222> LOCATION: (39)..(39)
<223> OTHER INFORMATION: Ser at position 39 is amidated

<400> SEQUENCE: 41

Tyr Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 42
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (30)..(30)
<223> OTHER INFORMATION: Gly at position 30 is amidated

<400> SEQUENCE: 42

Tyr Xaa Glu Gly Thr Phe Thr Ser Asp Tyr Ser Ile Leu Leu Asp Lys
1               5                   10                  15

Ile Ala Gln Xaa Ala Phe Ile Glu Tyr Leu Ile Lys Gly Gly
            20                  25                  30

<210> SEQ ID NO 43
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is D-Ala
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 43
```

```
Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35
```

```
<210> SEQ ID NO 44
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (11)..(11)
<223> OTHER INFORMATION: Xaa at position 11 is D-Ser
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 44

Tyr Xaa Glu Gly Thr Phe Thr Ser Asp Tyr Xaa Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35
```

```
<210> SEQ ID NO 45
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (28)..(28)
<223> OTHER INFORMATION: Xaa at position 28 is D-Glu
<220> FEATURE:
<221> NAME/KEY: MOD_RES
```

```
<222> LOCATION: (39)..(39)
<223> OTHER INFORMATION: Ser at position 39 is amidated

<400> SEQUENCE: 45

Tyr Xaa Glu Gly Thr Phe Thr Ser Asp Tyr Ser Ile Leu Leu Asp Lys
 1               5                  10                  15

Lys Ala Gln Xaa Ala Phe Ile Glu Tyr Leu Ile Xaa Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 46

Tyr Xaa Glu Gly Thr Phe Thr Ser Asp Tyr Ser Ile Leu Leu Asp Lys
 1               5                  10                  15

Lys Ala Gln Xaa Ala Phe Ile Xaa Tyr Leu Ile Glu Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated
```

<400> SEQUENCE: 47

Tyr Pro Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 48
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (3)..(3)
<223> OTHER INFORMATION: Xaa at position 3 is Aad
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 48

Tyr Xaa Xaa Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
            35

<210> SEQ ID NO 49
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H

```
<220> FEATURE:
<221> NAME/KEY: MOD_RES
<222> LOCATION: (30)..(30)
<223> OTHER INFORMATION: Gly at position 30 is amidated

<400> SEQUENCE: 49

Tyr Xaa Glu Gly Thr Xaa Thr Ser Asp Tyr Ser Ile Leu Leu Asp Lys
 1               5                  10                  15

Ile Ala Gln Xaa Ala Phe Ile Glu Tyr Leu Ile Lys Gly Gly
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (28)..(28)
<223> OTHER INFORMATION: Lys at position 28 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MOD_RES
<222> LOCATION: (30)..(30)
<223> OTHER INFORMATION: Gly at position 30 is amidated

<400> SEQUENCE: 50

Tyr Xaa Glu Gly Thr Phe Thr Ser Asp Tyr Ser Ile Xaa Leu Asp Lys
 1               5                  10                  15

Ile Ala Gln Xaa Ala Phe Ile Glu Tyr Leu Ile Lys Gly Gly
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 13 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
```

```
<221> NAME/KEY: MOD_RES
<222> LOCATION: (30)..(30)
<223> OTHER INFORMATION: Gly at position 30 is amidated

<400> SEQUENCE: 51

Tyr Xaa Glu Gly Thr Xaa Thr Ser Asp Tyr Ser Ile Leu Leu Asp Lys
1               5                   10                  15

Lys Ala Gln Xaa Ala Phe Ile Glu Tyr Leu Ile Glu Gly Gly
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 52

Tyr Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Gly Gly
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
```

```
            (2-[2-(2-amino-ethoxy)-ethoxy]-acetyl)2-(gamma-Glu)-CO-(CH2)18-
            CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 53

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
            conjugation of the epsilon-amino group of the Lys side chain with
            (2-[2-(2-amino-ethoxy)-ethoxy]-acetyl)2-(gamma-Glu)-CO-(CH2)16-
            CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (30)..(30)
<223> OTHER INFORMATION: Gly at position 30 is amidated

<400> SEQUENCE: 54

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly
            20                  25                  30

<210> SEQ ID NO 55
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
            conjugation of the epsilon-amino group of the Lys side chain with
            (2-[2-(2-amino-ethoxy)-ethoxy]-acetyl)-AOC-(gamma-Glu)-CO-(CH2)18-
```

```
        CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 55

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      AOC-(2-[2-(2-amino-ethoxy)-ethoxy]-acetyl)-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 56

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 57
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(gamma-Glu)-(Trx)-CO-
      (CH2)18-CO2H
<220> FEATURE:
<221> NAME/KEY: MISC_FEATURE
```

```
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 57

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(Trx)-(gamma-Glu)-CO-
      (CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 58

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 59
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(epsilon-Lys)-(gamma-Glu)-
      CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
```

```
<221> NAME/KEY: MOD_RES
<222> LOCATION: (39)..(39)
<223> OTHER INFORMATION: Ser at position 39 is amidated

<400> SEQUENCE: 59

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 60
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 60

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 61
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)-(epsilon-Lys)-(epsilon-
      Lys)-CO-(CH2)18-CO2H
<220> FEATURE:
<221> NAME/KEY: MISC_FEATURE
<222> LOCATION: (20)..(20)
<223> OTHER INFORMATION: Xaa at position 2 is Aib
<220> FEATURE:
<221> NAME/KEY: MOD_RES
<222> LOCATION: (39)..(39)
<223> OTHER INFORMATION: Ser at position 39 is amidated
```

<400> SEQUENCE: 61

Tyr Xaa Glu Gly Thr Phe Thr Ser Asp Tyr Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 62
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 62

Tyr Xaa Glu Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES

```
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 63

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Tyr Leu Ile Glu Gly Gly Pro Ser
                20                  25                  30

Ser Gly Ala Pro Pro Pro Ser
            35

<210> SEQ ID NO 64
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (3)..(3)
<223> OTHER INFORMATION: Xaa at position 3 is cTA
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 64

Tyr Xaa Xaa Gly Thr Xaa Thr Ser Asp Tyr Ser Ile Xaa Leu Asp Glu
1               5                   10                  15

Lys Ala Gln Xaa Ala Phe Ile Glu Tyr Leu Ile Glu Gly Gly Pro Ser
                20                  25                  30

Ser Gly Ala Pro Pro Pro Ser
            35

<210> SEQ ID NO 65
<211> LENGTH: 34
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (34)..(34)
<223> OTHER INFORMATION: Gly at position 34 is amidated

<400> SEQUENCE: 65

Tyr Xaa Glu Gly Thr Xaa Thr Ser Asp Tyr Ser Ile Xaa Leu Asp Lys
1               5                   10                  15

Lys Ala Gln Xaa Glu Phe Ile Glu Tyr Leu Ile Glu Gly Gly Pro Ser
            20                  25                  30

Ser Gly

<210> SEQ ID NO 66
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)2-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 66

Tyr Xaa Glu Gly Thr Xaa Thr Ser Asp Tyr Ser Ile Xaa Leu Asp Lys
```

```
1               5                   10                  15
Lys Ala Gln Xaa Ala Phe Ile Glu Tyr Leu Ile Glu Gly Gly Pro Ser
            20                  25                  30

Ser Gly Ala Pro Pro Pro Ser
            35
```

<210> SEQ ID NO 67
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 67

```
Tyr Xaa Glu Gly Thr Xaa Thr Ser Asp Tyr Ser Ile Xaa Leu Asp Lys
1               5                   10                  15

Lys Ala Gln Xaa Ala Phe Ile Glu Tyr Leu Ile Glu Ala Gly Pro Ser
            20                  25                  30

Ser Gly Ala Pro Pro Pro Ser
            35
```

<210> SEQ ID NO 68
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)

```
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 68

Tyr Xaa Glu Gly Thr Xaa Thr Ser Asp His Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 69

Tyr Xaa Glu Gly Thr Xaa Thr Ser Asp Leu Ser Ile Leu Leu Asp Lys
1               5                   10                  15

Lys Ala Gln Xaa Ala Phe Ile Glu Tyr Leu Ile Glu Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
```

<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (21)..(21)
<223> OTHER INFORMATION: Xaa at position 21 is Aad
<220> FEATURE:
<221> NAME/KEY: MOD_RES
<222> LOCATION: (39)..(39)
<223> OTHER INFORMATION: Ser at position 39 is amidated

<400> SEQUENCE: 70

Tyr Xaa Glu Gly Thr Xaa Thr Ser Asp Tyr Ser Ile Xaa Leu Asp Lys
1               5                   10                  15

Lys Ala Gln Xaa Xaa Phe Ile Glu Tyr Leu Ile Glu Gly Gly Pro Ser
            20                  25                  30

Ser Gly Ala Pro Pro Pro Ser
            35

<210> SEQ ID NO 71
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 71

Tyr Xaa Glu Gly Thr Xaa Thr Ser Asp Tyr Ser Ile Xaa Leu Asp Lys
1               5                   10                  15

Lys Ala Gln Xaa Thr Phe Ile Glu Tyr Leu Ile Glu Gly Gly Pro Ser
            20                  25                  30

Ser Gly Ala Pro Pro Pro Ser
            35

<210> SEQ ID NO 72
<211> LENGTH: 39

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 72

Tyr Xaa Glu Gly Thr Xaa Thr Ser Asp Tyr Ser Ile Xaa Leu Asp Lys
1               5                   10                  15

Lys Ala Gln Xaa Asp Phe Ile Glu Tyr Leu Ile Glu Gly Gly Pro Ser
            20                  25                  30

Ser Gly Ala Pro Pro Pro Ser
        35

<210> SEQ ID NO 73
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (21)..(21)
<223> OTHER INFORMATION: Xaa at position 21 is Aib
<220> FEATURE:
<221> NAME/KEY: MOD_RES
```

<222> LOCATION: (39)..(39)
<223> OTHER INFORMATION: Ser at position 39 is amidated

<400> SEQUENCE: 73

Tyr Xaa Glu Gly Thr Xaa Thr Ser Asp Tyr Ser Ile Xaa Leu Asp Lys
1               5                   10                  15

Lys Ala Gln Xaa Xaa Phe Ile Glu Tyr Leu Ile Glu Gly Gly Pro Ser
            20                  25                  30

Ser Gly Ala Pro Pro Pro Ser
        35

<210> SEQ ID NO 74
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (21)..(21)
<223> OTHER INFORMATION: Xaa at position 21 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 74

Tyr Xaa Glu Gly Thr Xaa Thr Ser Asp Tyr Ser Ile Xaa Leu Asp Lys
1               5                   10                  15

Lys Ala Gln His Xaa Phe Ile Glu Tyr Leu Ile Glu Gly Gly Pro Ser
            20                  25                  30

Ser Gly Ala Pro Pro Pro Ser
        35

<210> SEQ ID NO 75
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu

```
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is Aad
<220> FEATURE:
<221> NAME/KEY: MOD_RES
<222> LOCATION: (39)..(39)
<223> OTHER INFORMATION: Ser at position 39 is amidated

<400> SEQUENCE: 75

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
            35

<210> SEQ ID NO 76
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 76

Tyr Xaa Glu Gly Thr Xaa Thr Ser Asp Tyr Ser Ile Xaa Leu Asp Glu
1               5                   10                  15

Lys Ala Gln Xaa Glu Phe Ile Ala Tyr Leu Ile Glu Gly Gly Pro Ser
                20                  25                  30

Ser Gly Ala Pro Pro Pro Ser
            35

<210> SEQ ID NO 77
```

```
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 77

Tyr Xaa Glu Gly Thr Xaa Thr Ser Asp Tyr Ser Ile Xaa Leu Asp Glu
1               5                   10                  15

Lys Ala Gln Xaa Glu Phe Ile Val Tyr Leu Ile Glu Gly Gly Pro Ser
            20                  25                  30

Ser Gly Ala Pro Pro Pro Ser
        35

<210> SEQ ID NO 78
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated
```

-continued

<400> SEQUENCE: 78

Tyr Xaa Glu Gly Thr Xaa Thr Ser Asp Tyr Ser Ile Xaa Leu Asp Glu
1               5                   10                  15

Lys Ala Gln Xaa Glu Phe Ile Ser Tyr Leu Ile Glu Gly Gly Pro Ser
            20                  25                  30

Ser Gly Ala Pro Pro Pro Ser
        35

<210> SEQ ID NO 79
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 79

Tyr Xaa Glu Gly Thr Xaa Thr Ser Asp Tyr Ser Ile Xaa Leu Asp Glu
1               5                   10                  15

Lys Ala Gln Xaa Glu Phe Ile Pro Tyr Leu Ile Glu Gly Gly Pro Ser
            20                  25                  30

Ser Gly Ala Pro Pro Pro Ser
        35

<210> SEQ ID NO 80
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)

<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)18-
CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 80

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
        35

<210> SEQ ID NO 81
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)18-
CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 81

Tyr Xaa Glu Gly Thr Xaa Thr Ser Asp Tyr Ser Ile Xaa Leu Asp Glu
1               5                   10                  15

Lys Ala Gln Xaa Glu Phe Ile His Tyr Leu Ile Glu Gly Gly Pro Ser
                20                  25                  30

Ser Gly Ala Pro Pro Pro Ser
        35

<210> SEQ ID NO 82
<211> LENGTH: 39
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 82

Tyr Xaa Glu Gly Thr Xaa Thr Ser Asp His Ser Ile Xaa Leu Asp Glu
1               5                   10                  15

Lys Ala Gln Xaa Glu Phe Ile Glu Tyr Leu Ile Glu Gly Gly Pro Ser
            20                  25                  30

Ser Gly Ala Pro Pro Pro Ser
        35

<210> SEQ ID NO 83
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is cTA
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated
```

```
<400> SEQUENCE: 83

Tyr Xaa Glu Gly Thr Xaa Thr Ser Asp Xaa Ser Ile Xaa Leu Asp Glu
1               5                   10                  15

Lys Ala Gln Xaa Glu Phe Ile Glu Tyr Leu Ile Glu Gly Gly Pro Ser
                20                  25                  30

Ser Gly Ala Pro Pro Ser
            35

<210> SEQ ID NO 84
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 3Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MOD_RES
<222> LOCATION: (39)..(39)
<223> OTHER INFORMATION: Ser at position 39 is amidated

<400> SEQUENCE: 84

Tyr Xaa Glu Gly Thr Xaa Thr Ser Asp Xaa Ser Ile Xaa Leu Asp Glu
1               5                   10                  15

Lys Ala Gln Xaa Glu Phe Ile Glu Tyr Leu Ile Glu Gly Gly Pro Ser
                20                  25                  30

Ser Gly Ala Pro Pro Ser
            35

<210> SEQ ID NO 85
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
```

```
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 85

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly

<210> SEQ ID NO 86
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 86

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30
```

Ser Gly Ala Pro Pro Pro Ser
        35

<210> SEQ ID NO 87
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 87

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 88
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)

<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 88

Tyr Xaa Glu Gly Thr Xaa Thr Ser Asp His Ser Ile Xaa Leu Asp Xaa
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 89
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is a Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 89

Tyr Xaa Glu Gly Thr Xaa Thr Ser Asp His Ser Ile Xaa Leu Asp Xaa
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 90
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 90

Tyr Xaa Glu Gly Thr Xaa Thr Ser Asp His Ser Ile Xaa Leu Asp Xaa
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 91
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)

<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 91

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 92
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 92

Tyr Xaa Glu Gly Thr Xaa Thr Ser Asp His Ser Ile Xaa Leu Asp Glu
1               5                   10                  15

Lys Ala Gln Xaa Thr Phe Ile Xaa Tyr Leu Ile Glu Gly Gly Pro Ser
            20                  25                  30

Ser Gly Ala Pro Pro Pro Ser
        35

<210> SEQ ID NO 93

```
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)14-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 93

Tyr Xaa Glu Gly Thr Xaa Thr Ser Asp His Ser Ile Xaa Leu Asp Glu
1               5                   10                  15

Lys Ala Gln Xaa His Phe Ile Xaa Tyr Leu Ile Glu Gly Gly Pro Ser
                20                  25                  30

Ser Gly Ala Pro Pro Ser
        35

<210> SEQ ID NO 94
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
```

```
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 94

Tyr Xaa Glu Gly Thr Xaa Thr Ser Asp His Ser Ile Xaa Leu Asp Glu
1               5                   10                  15

Lys Ala Gln Xaa His Phe Ile Xaa Tyr Leu Ile Glu Gly Gly Pro Ser
            20                  25                  30

Ser Gly

<210> SEQ ID NO 95
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (30)..(30)
<223> OTHER INFORMATION: Gly at position 30 is amidated

<400> SEQUENCE: 95

Tyr Xaa Glu Gly Thr Xaa Thr Ser Asp His Ser Ile Xaa Leu Asp Glu
1               5                   10                  15

Lys Ala Gln Xaa His Phe Ile Xaa Tyr Leu Ile Glu Gly Gly
            20                  25                  30

<210> SEQ ID NO 96
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
```

```
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 3Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 96

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 97
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
```

```
<221> NAME/KEY: MOD_RES
<222> LOCATION: (39)..(39)
<223> OTHER INFORMATION: Ser at position 39 is amidated

<400> SEQUENCE: 97

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 98
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 98

Tyr Xaa Glu Gly Thr Xaa Thr Ser Asp Leu Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 99
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
```

```
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 99

Tyr Xaa Glu Gly Thr Xaa Thr Ser Asp Gln Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 100
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is Aib
<220> FEATURE:
<221> NAME/KEY: MOD_RES
<222> LOCATION: (39)..(39)
<223> OTHER INFORMATION: Ser at position 39 is amidated
```

<400> SEQUENCE: 100

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
            35

<210> SEQ ID NO 101
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is alpha-methyl-Pro
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MOD_RES
<222> LOCATION: (34)..(34)
<223> OTHER INFORMATION: Gly at position 34 is amidated

<400> SEQUENCE: 101

Tyr Xaa Glu Gly Thr Phe Thr Ser Asp Tyr Ser Ile Leu Leu Asp Glu
1               5                   10                  15

Lys Ala Gln Gln Ala Phe Ile Glu Tyr Leu Ile Glu Gly Gly Pro Ser
                20                  25                  30

Ser Gly

<210> SEQ ID NO 102
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-(2-[2-(2-Amino-
      ethoxy)-ethoxy]-acetyl)-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:

```
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 102

Tyr Xaa Glu Gly Thr Xaa Thr Ser Asp Xaa Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 103
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 103

Tyr Xaa Glu Gly Thr Xaa Thr Ser Asp Xaa Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 104
<211> LENGTH: 39
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 104

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
                20                  25                  30

Ser Gly Ala Pro Pro Pro Ser
        35

<210> SEQ ID NO 105
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)16-CO2H
<220> FEATURE:
<221> NAME/KEY: MISC_FEATURE
```

```
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 105

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 106
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 106

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 107
<211> LENGTH: 39
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 107

Tyr Xaa Glu Gly Thr Xaa Thr Ser Asp Xaa Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 108
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)14-
      CO2H
<220> FEATURE:
<221> NAME/KEY: MISC_FEATURE
<222> LOCATION: (20)..(20)
```

```
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 108

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 109
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 109

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 110
<211> LENGTH: 39
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 110

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 111
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-Amino-ethoxy)-ethoxy]-acetyl)-(gamma-Glu)-(2-[2-(2-Amino-
      ethoxy)-ethoxy]-acetyl)-CO-(CH2)18-CO2H
<220> FEATURE:
<221> NAME/KEY: MISC_FEATURE
<222> LOCATION: (20)..(20)
```

<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 111

Tyr Xaa Glu Gly Thr Xaa Thr Ser Asp Tyr Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 112
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 112

Tyr Xaa Glu Gly Thr Xaa Thr Ser Asp Tyr Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 113
<211> LENGTH: 39
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 113

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 114
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)16-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated
```

<400> SEQUENCE: 114

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 115
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-CO-(CH2)18-CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 115

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 116
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)

<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 116

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 117
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 117

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20              25                  30

Ser Gly Ala Pro Pro Pro Ser
        35

<210> SEQ ID NO 118
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Dap
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 118

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20              25                  30

Ser Gly Ala Pro Pro Pro Ser
        35

<210> SEQ ID NO 119
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)

```
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 119

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly

<210> SEQ ID NO 120
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (30)..(30)
<223> OTHER INFORMATION: Gly at position 30 is amidated

<400> SEQUENCE: 120

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly
            20                  25                  30
```

-continued

```
<210> SEQ ID NO 121
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 121

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 122
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
```

```
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 122

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Xaa Leu Ile Glu Gly Gly Pro Ser
            20                  25                  30

Ser Gly Ala Pro Pro Pro Ser
            35

<210> SEQ ID NO 123
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 123

Tyr Xaa Glu Gly Thr Xaa Thr Ser Asp Tyr Ser Ile Xaa Leu Asp Glu
1               5                   10                  15

Lys Ala Gln Xaa Glu Phe Ile Glu Xaa Leu Ile Glu Gly Gly Pro Ser
            20                  25                  30

Ser Gly Ala Pro Pro Pro Ser
            35

<210> SEQ ID NO 124
<211> LENGTH: 39
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 124

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 125
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
```

<220> FEATURE:
<221> NAME/KEY: MOD_RES
<222> LOCATION: (39)..(39)
<223> OTHER INFORMATION: Ser at position 39 is amidated

<400> SEQUENCE: 125

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 126
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 126

Tyr Xaa Glu Gly Thr Xaa Thr Ser Asp Tyr Ser Ile Leu Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 127
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE

```
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 127

Tyr Xaa Glu Gly Thr Xaa Thr Ser Asp Tyr Ser Ile Xaa Leu Asp Glu
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 128
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (34)..(34)
<223> OTHER INFORMATION: Gly at position 34 is amidated

<400> SEQUENCE: 128

Tyr Xaa Glu Gly Thr Xaa Thr Ser Asp Tyr Ser Ile Xaa Leu Asp Lys
1               5                   10                  15

Lys Ala Gln Xaa Glu Phe Ile Xaa Tyr Leu Ile Glu Gly Gly Pro Ser
            20                  25                  30
```

Ser Gly

<210> SEQ ID NO 129
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MOD_RES
<222> LOCATION: (17)..(17)
<223> OTHER INFORMATION: Lys at position 17 is chemically modified by
    conjugation of the epsilon-amino group of the Lys side chain with
    (2-[2-(2-amino-ethoxy)-ethoxy]-acetyl)2-(gamma-Glu)-CO-(CH2)18-
    CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 129

Tyr Xaa Glu Gly Thr Xaa Thr Ser Asp Tyr Ser Ile Xaa Leu Asp His
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 130
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)

<223> OTHER INFORMATION: Xaa at position 16 is Dab
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 130

Tyr Xaa Glu Gly Thr Xaa Thr Ser Asp Xaa Ser Ile Xaa Leu Asp Xaa
 1               5                  10                  15

Lys Ala Gln Xaa Glu Phe Ile Xaa Tyr Leu Ile Glu Gly Gly Pro Ser
                20                  25                  30

Ser Gly Ala Pro Pro Pro Ser
             35

<210> SEQ ID NO 131
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 131

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Xaa Leu Ile Glu Gly Gly Pro Ser
                20                  25                  30

Ser Gly Ala Pro Pro Pro Ser
            35

<210> SEQ ID NO 132
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 132

Tyr Xaa Glu Gly Thr Xaa Thr Ser Asp Leu Ser Ile Xaa Leu Asp Xaa
1               5                   10                  15

Lys Ala Gln Xaa Glu Phe Ile Xaa Xaa Leu Ile Glu Gly Gly Pro Ser
                20                  25                  30

Ser Gly Ala Pro Pro Pro Ser
            35

<210> SEQ ID NO 133
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)

```
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 133

Tyr Xaa Glu Gly Thr Xaa Thr Ser Asp Xaa Ser Ile Xaa Leu Asp Xaa
1               5                  10                  15

Lys Ala Gln Xaa Thr Phe Ile Xaa Xaa Leu Ile Glu Gly Gly Pro Ser
            20                  25                  30

Ser Gly Ala Pro Pro Ser
        35

<210> SEQ ID NO 134
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
``` conjugation of the epsilon-amino group of the Lys side chain with
(2-[2-(2-amino-ethoxy)-ethoxy]-acetyl)2-(gamma-Glu)-CO-(CH2)16-
CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 134

Tyr Xaa Glu Gly Thr Xaa Thr Ser Asp Val Ser Ile Xaa Leu Asp Xaa
1               5                   10                  15

Lys Ala Gln Xaa Thr Phe Ile Xaa Xaa Leu Ile Glu Gly Gly Pro Ser
            20                  25                  30

Ser Gly Ala Pro Pro Pro Ser
        35

<210> SEQ ID NO 135
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
conjugation of the epsilon-amino group of the Lys side chain with
(2-[2-(2-amino-ethoxy)-ethoxy]-acetyl)2-(gamma-Glu)-CO-(CH2)16-
CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 135

```
Tyr Xaa Glu Gly Thr Xaa Thr Ser Asp Val Ser Ile Xaa Leu Asp Xaa
1               5                   10                  15

Lys Ala Gln Xaa Ala Phe Ile Xaa Xaa Leu Ile Glu Gly Gly Pro Ser
                20                  25                  30

Ser Gly Ala Pro Pro Pro Ser
                35
```

<210> SEQ ID NO 136
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 136

```
Tyr Xaa Glu Gly Thr Xaa Thr Ser Asp Leu Ser Ile Xaa Leu Asp Xaa
1               5                   10                  15

Lys Ala Gln Xaa Thr Phe Ile Xaa Xaa Leu Ile Glu Gly Gly Pro Ser
                20                  25                  30

Ser Gly Ala Pro Pro Pro Ser
                35
```

<210> SEQ ID NO 137
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib

```
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 137

Tyr Xaa Glu Gly Thr Xaa Thr Ser Asp Leu Ser Ile Xaa Leu Asp Xaa
1               5                   10                  15

Lys Ala Gln Xaa Ala Phe Ile Xaa Xaa Leu Ile Glu Gly Gly Pro Ser
                20                  25                  30

Ser Gly Ala Pro Pro Pro Ser
            35

<210> SEQ ID NO 138
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
```

```
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 138

Tyr Xaa Glu Gly Thr Xaa Thr Ser Asp Ala Ser Ile Xaa Leu Asp Xaa
1               5                   10                  15

Lys Ala Gln Xaa Ala Phe Ile Xaa Xaa Leu Ile Glu Gly Gly Pro Ser
            20                  25                  30

Ser Gly Ala Pro Pro Pro Ser
        35

<210> SEQ ID NO 139
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 139

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35
```

<210> SEQ ID NO 140
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 140

Tyr Xaa Glu Gly Thr Xaa Thr Ser Asp Tyr Ser Ile Leu Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
        35

<210> SEQ ID NO 141
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Nle
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with

```
        (2-[2-(2-amino-ethoxy)-ethoxy]-acetyl)2-(gamma-Glu)-CO-(CH2)16-
        CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 141

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35

<210> SEQ ID NO 142
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (13)..(13)
<223> OTHER INFORMATION: Xaa at position 13 is Aib
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
        conjugation of the epsilon-amino group of the Lys side chain with
        (2-[2-(2-amino-ethoxy)-ethoxy]-acetyl)2-(gamma-Glu)-CO-(CH2)18-
        CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MOD_RES
<222> LOCATION: (39)..(39)
<223> OTHER INFORMATION: Ser at position 39 is amidated

<400> SEQUENCE: 142

Tyr Xaa Glu Gly Thr Xaa Thr Ser Asp Tyr Ser Ile Xaa Leu Asp Xaa
1               5                   10                  15

Lys Ala Gln Xaa Glu Phe Ile Xaa Tyr Leu Ile Glu Gly Gly Pro Ser
            20                  25                  30

Ser Gly Ala Pro Pro Pro Ser
            35
```

```
<210> SEQ ID NO 143
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(epsilon-Lys)-CO-(CH2)18-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (39)..(39)
<223> OTHER INFORMATION: Ser at position 39 is amidated

<400> SEQUENCE: 143

Tyr Xaa Glu Gly Thr Xaa Thr Ser Asp Xaa Ser Ile Xaa Leu Asp Xaa
1               5                   10                  15

Lys Ala Gln Xaa Ala Phe Ile Xaa Xaa Leu Ile Glu Gly Gly Pro Ser
            20                  25                  30

Ser Gly Ala Pro Pro Pro Ser
        35

<210> SEQ ID NO 144
<211> LENGTH: 34
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
```

```
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (34)..(34)
<223> OTHER INFORMATION: Gly at position 34 is amidated

<400> SEQUENCE: 144

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Xaa Leu Ile Glu Gly Gly Pro Ser
            20                  25                  30

Ser Gly

<210> SEQ ID NO 145
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-methyl-Phe(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-methyl-Leu
<220> FEATURE:
<221> NAME/KEY: MISC_FEATURE
<222> LOCATION: (16)..(16)
<223> OTHER INFORMATION: Xaa at position 13 is Orn
<220> FEATURE:
<221> NAME/KEY: MOD_RES
<222> LOCATION: (17)..(17)
<223> OTHER INFORMATION: Lys at position 17 is chemically modified by
      conjugation of the epsilon-amino group of the Lys side chain with
      (2-[2-(2-amino-ethoxy)-ethoxy]-acetyl)2-(gamma-Glu)-CO-(CH2)16-
      CO2H
```

```
<220> FEATURE:
<221> NAME/KEY: MISC_FEATURE
<222> LOCATION: (20)..(20)
<223> OTHER INFORMATION: Xaa at position 20 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-methyl-Tyr
<220> FEATURE:
<221> NAME/KEY: MOD_RES
<222> LOCATION: (30)..(30)
<223> OTHER INFORMATION: Gly at position 30 is amidated

<400> SEQUENCE: 145

Tyr Xaa Glu Gly Thr Xaa Thr Ser Asp Xaa Ser Ile Xaa Leu Asp Xaa
1               5                   10                  15

Lys Ala Gln Xaa Glu Phe Ile Xaa Xaa Leu Ile Glu Gly Gly
            20                  25                  30
```

We claim:

1. A method of treating type 2 diabetes in a patient in need thereof, comprising:
   a) administering to said patient a first dose of a GIP:GLP-1 Peptide, or a pharmaceutically acceptable salt thereof, having a GIP:GLP-1 receptor agonist potency ratio that is greater than or equal to the GIP:GLP-1 receptor agonist potency ratio of a GIP:GLP-1 Peptide having SEQ ID NO: 62 and less than the GIP:GLP-1 receptor agonist potency ratio of a GIP:GLP-1 Peptide having SEQ ID NO:55, wherein the GIP:GLP-1 agonist potency ratio is measured after a 60 minute incubation using a casein cAMP assay normalized against GIP and GLP-1; and thereafter
   b) administering to said patient a second dose of the GIP:GLP-1 Peptide, or pharmaceutically acceptable salt thereof, for a minimum of about two weeks; and thereafter
   c) administering to said patient a third dose of the GIP:GLP-1 Peptide, or pharmaceutically acceptable salt thereof, for a minimum of about two weeks; and thereafter
   d) administering to said patient a fourth dose of the GIP:GLP-1 Peptide, or pharmaceutically acceptable salt thereof;

wherein the first dose is about 25% of the fourth dose, the second dose is about 50% of the fourth dose and the third dose is about 75% of the fourth dose.

2. The method of claim 1, wherein the doses are each administered for about four weeks before the administration of the next higher dose begins.

* * * * *